United States Patent
Kobayashi et al.

(10) Patent No.: US 9,511,933 B2
(45) Date of Patent: Dec. 6, 2016

(54) STORAGE APPARATUS

(71) Applicant: SANYO ELECTRIC CO., LTD., Moriguchi-shi, Osaka (JP)

(72) Inventors: Masahiko Kobayashi, Oizuma-machi (JP); Mikio Houjou, Higashiosaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 699 days.

(21) Appl. No.: 13/896,928

(22) Filed: May 17, 2013

(65) Prior Publication Data
US 2013/0251483 A1   Sep. 26, 2013

Related U.S. Application Data

(63) Continuation of application No. PCT/JP2012/073074, filed on Sep. 10, 2012.

(30) Foreign Application Priority Data

Sep. 22, 2011 (JP) .................. 2011-207709
Sep. 29, 2011 (JP) .................. 2011-214951

(51) Int. Cl.
  *B65G 1/04* (2006.01)
  *B65G 1/06* (2006.01)
  *C12M 3/00* (2006.01)
(52) U.S. Cl.
  CPC .............. *B65G 1/065* (2013.01); *C12M 23/48* (2013.01); *B65G 1/04* (2013.01)
(58) Field of Classification Search
  CPC .............................. B65G 1/065; B65G 1/0435
  See application file for complete search history.

(56) References Cited

U.S. PATENT DOCUMENTS

| 4,328,422 A * | 5/1982 | Loomer ................ B65G 1/065 250/202 |
| 5,915,909 A * | 6/1999 | Smith .................. B65G 1/0435 187/360 |
| 2009/0196720 A1* | 8/2009 | Kostmann ............ B65G 1/0435 414/331.01 |

FOREIGN PATENT DOCUMENTS

| JP | 3-67806 A | 3/1991 |
| JP | 3601178 B2 | 10/2004 |
| JP | 2006-101781 A | 4/2006 |
| JP | 2006-282332 A | 10/2006 |
| JP | 4501017 B2 | 4/2010 |
| WO | 2008/108092 A1 | 9/2008 |
| WO | 2012/114635 A1 | 8/2012 |

* cited by examiner

*Primary Examiner* — Jonathan Snelting
(74) *Attorney, Agent, or Firm* — Cantor Colburn LLP

(57) ABSTRACT

A storage apparatus includes: a storage member provided with a pair of first rail members, extending along a horizontal direction, on both side faces thereof; a storage rack; a carrying mechanism to carry the storage member placed thereon in the horizontal direction to a storage location of the storage rack; and a pair of walls, provided so as to be opposed to the side faces of the storage member, respectively, having a pair of second rail members, extending in the horizontal direction, provided on side faces thereof opposed to the pair of first rail members, respectively, in a state where the storage member is stored in the storage rack, the storage member being guided to the storage rack with the pair of first rail members being supported by the pair of second rail members, when the carrying mechanism is moved in the horizontal direction toward the storage rack.

6 Claims, 38 Drawing Sheets

STORAGE APPARATUS

CROSS-REFERENCE TO RELATED APPLICATIONS

This is a continuation application of International Patent Application No. PCT/JP2012/073074 filed Sep. 10, 2012, which claims the benefit of priority to Japanese Patent Application Nos. 2011-207709 and 2011-214951, filed Sep. 22, 2011 and Sep. 29, 2011, respectively. The full contents of the International Patent Application are incorporated herein by reference.

BACKGROUND OF THE INVENTION

1. Field of the Invention

The present invention relates to a storage apparatus.

2. Description of the Related Art

Development of a culture apparatus has been proceeding, which appropriately controls for example, e.g., temperature, humidity, and efficiently cultivates a culture such as a cell.

In the culture apparatus, a plurality of containers each containing a culture are stored in a storage rack. At the start and the end of culturing and when checking on a culture, the containers are taken out from the storage rack, are stored in the storage rack, and are moved, using a carrier device configured to move in the culture apparatus.

At such times, a culture in the containers is easily affected by shaking, and in addition, if the culture liquid spills from the container, the inside of the culture apparatus is contaminated. Therefore, the carrier device carries and stores the containers in such a manner that shaking and inclination do not occur.

Various techniques have been developed to prevent the shaking and misalignment that occurs when such items are stored in the storage rack (see, e.g., Japanese Patent publication No. 3601178).

Today, research and development are actively conducted using cells in various fields such as the medical care, agriculture, and drug discovery.

In order to enable more efficient handling of a greater number of cultures, such a culture apparatus is required that stores containers each containing a culture in a rack referred to as a "stacker" in a multi-story manner, and that is capable of storing the containers into the storage rack, taking out them from the storage rack, and moving them, by the stacker as a unit.

In this case, the carrier device in the culture apparatus is required to have the ability to handle the containers one by one, and in addition, the ability to handle the stacker, which is loaded with the containers, and all.

However, if the carrier device is manufactured to be robust so that shaking and vibration do not occur even when the stacker fully loaded with the containers is carried and stored in the storage rack, the carrier device increase in size. Thus, when storing each of the containers into the stacker using the carrier device, it is necessary to increase intervals among the containers in the stacker so as to prevent interference between other containers stored in the stacker and the carrier device. Therefore, the storage efficiency of the containers in the stacker is degraded.

Similarly, it is also required to be capable of carrying the containers into the culture apparatus, carrying and storing the containers into the storage rack in the culture apparatus, and carrying the containers out from the culture apparatus, by the stacker as a unit.

SUMMARY OF THE INVENTION

A storage apparatus according to an aspect of the present invention, includes: a storage member configured to store a plurality of containers including liquid, the storage member provided with a pair of first rail members on both side faces thereof, the pair of first rail members extending along a horizontal direction; a storage rack configured to store the storage member; a carrying mechanism configured to carry the storage member placed thereon in the horizontal direction to a storage location of the storage rack so that the storage member will be stored in the storage rack; and a pair of walls, provided so as to be opposed to the side faces of the storage member, respectively, having a pair of second rail members provided on side faces thereof opposed to the pair of first rail members, respectively, in a state where the storage member is stored in the storage rack, the pair of second rail members extending in the horizontal direction, the storage member being guided to the storage rack with the pair of first rail members being supported by the pair of second rail members, when the carrying mechanism is moved in the horizontal direction toward the storage rack.

Other features of the present invention will become apparent from descriptions of this specification and of the accompanying drawings.

BRIEF DESCRIPTION OF THE DRAWINGS

For more thorough understanding of the present invention and advantages thereof, the following description should be read in conjunction with the accompanying drawings, in which:

FIG. 28 is a flowchart illustrating an example of a process executed when a target object is carried in;

DETAILED DESCRIPTION OF THE INVENTION

At least the following details will become apparent from descriptions of this specification and of the accompanying drawings.

First Embodiment

Outline of Incubator 10

Figure 1:
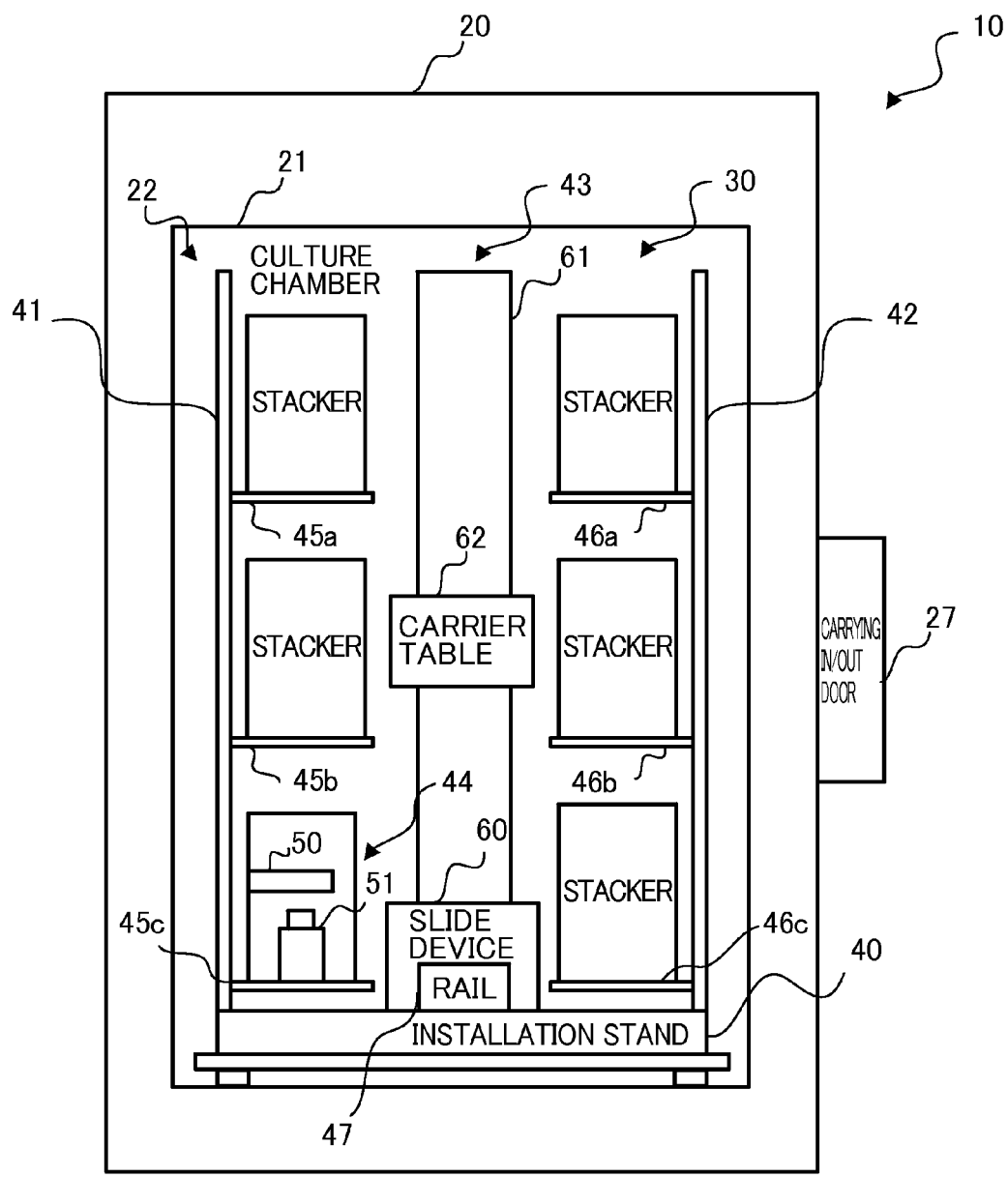
FIG. 1 is a front view of an incubator 10 according to an embodiment of the present invention.
Figure 2:
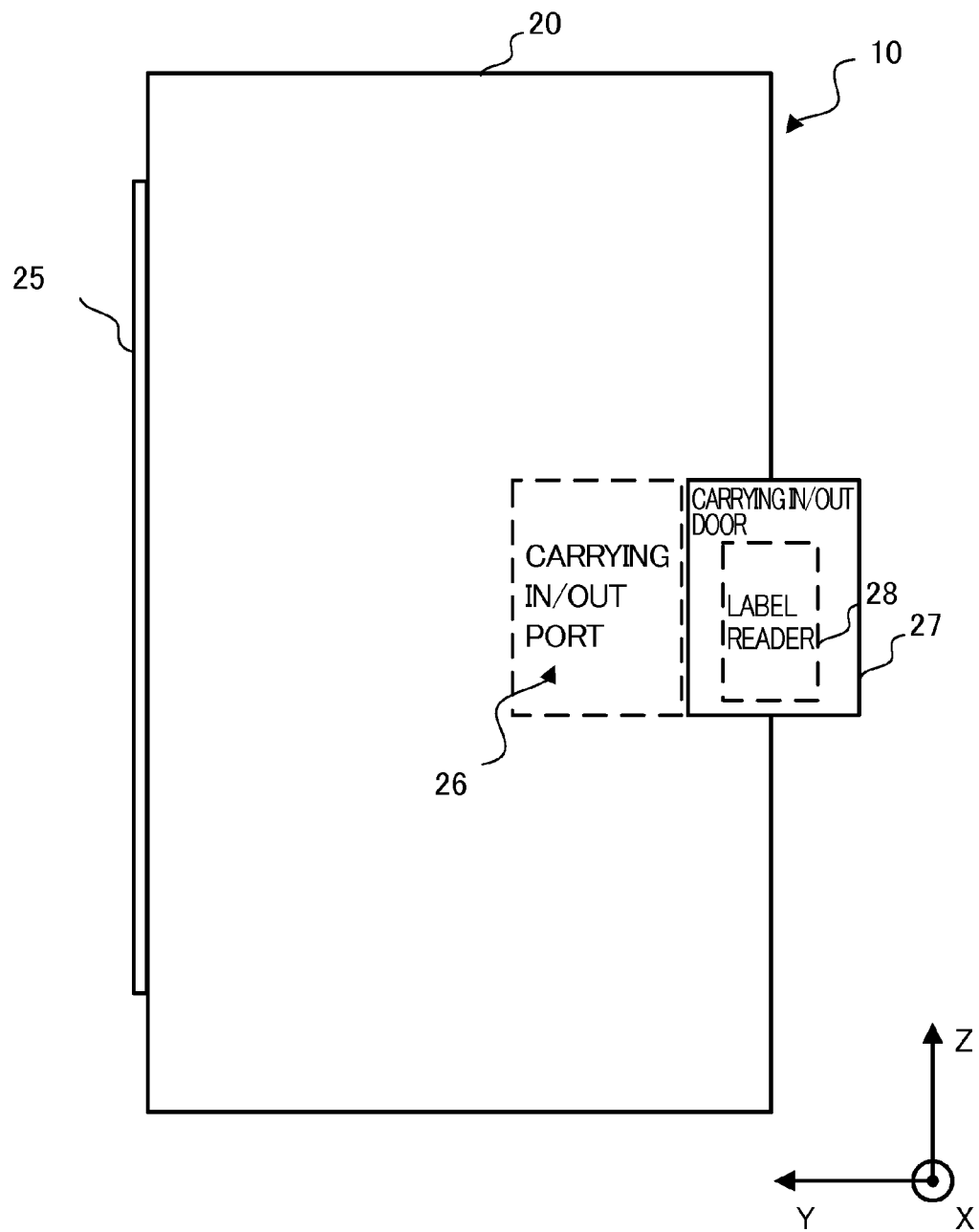
FIG. 2 is a side view of an incubator 10 viewed from a +X direction.
Figure 3:
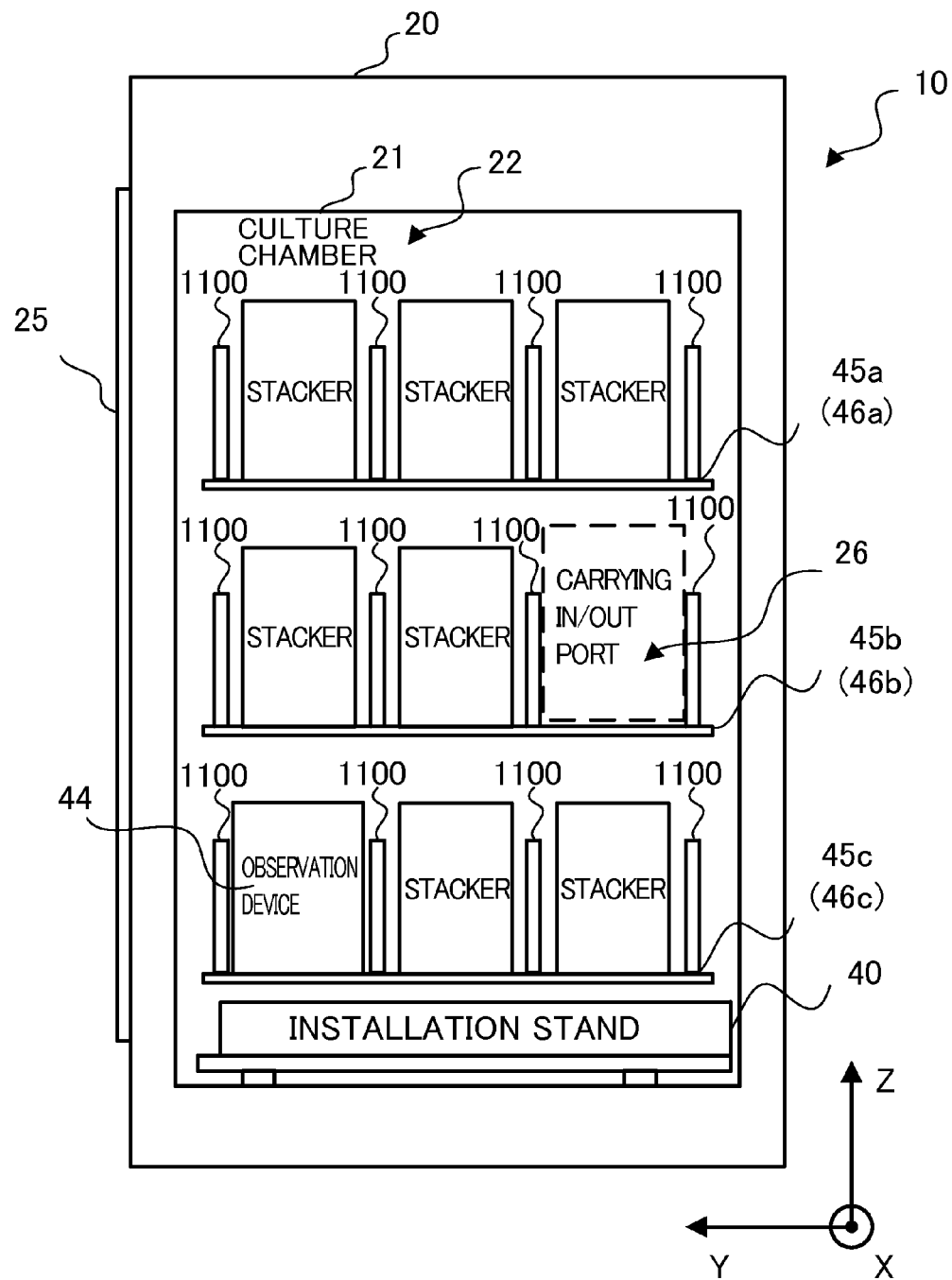
FIG. 3 is a perspective side view for describing an internal structure of an incubator 10.

A description will be given of a first embodiment in the case where a storage apparatus according to an embodiment of the present invention is applied to an incubator 10, with reference to FIGS. 1 to 3. FIG. 1 is a front view of the incubator 10 with a door on the front face thereof (on a +Y side) opened. FIG. 2 is a side view of the incubator 10 when viewed from a +X direction. FIG. 3 is a perspective side view describing the interior structure of the incubator 10. In an embodiment of the present invention, some components constituting the incubator 10 are appropriately omitted from the drawings to ease understanding of the structure of the incubator 10. Further, it is assumed that an X-axis direction is the left-right direction with respect to the incubator 10, a Y-axis direction is the front-back direction with respect to the incubator 10, and a Z-axis direction is the up-down direction with respect to the incubator 10.

The wording "horizontal direction" and "horizontal" may be used in the following description, and the "horizontal direction" and "horizontal" are respectively assumed to be a direction and to be in a direction of substantially 90 degrees with respect to the vertical direction, such as a direction of an angle in a range of 90±2 degrees, for example, more preferably, 90±0.5 degrees with respect thereto.

Similarly, the wording "vertical direction" and "vertical" may be used in the following description, and the "vertical direction" and "vertical" are respectively assumed to be a direction and to be in a direction of substantially 0 degree with respect to the vertical direction, such as a direction of an angle in a range of 0±2 degrees, for example, preferably, 0±0.5 degrees with respect thereto.

Further, the wording "right angle" may be used in the following description, and "right angle" is assumed such that an angle formed by two directions forming the right angle is substantially 90 degrees, such as an angle in a range of 90±2 degrees, for example, more preferably, 90±0.5 degrees.

Similarly, the wording "parallel" may be used in the following description, and "parallel" is assumed such that an angle of two directions in parallel to each other is about 0 degree, such as an angle in a range of 0±2 degrees, for example, more preferably, 0±0.5 degrees.

The incubator (storage apparatus) 10 is a device for use in cultivating a culture such as a cell (specimen) and a microorganism, and includes an outer case 20 and an inner case 21.

The outer case 20 is a so-called housing of the incubator 10 and is formed into a substantially rectangular parallelepiped shape with an opening portion in the front. On the inner side of the outer case 20, the inner case 21 having a shape with an opening portion in the front thereof similarly to the outer case 20 is provided so as to be covered by the outer case 20. Also provided at the front of the outer case 20 is a front door 25 to open or close the opening of the inner case 21. The internal space created in the inner case 21 when the front door 25 is closed is served as a culture chamber 22.

As depicted in FIG. 2, a carrying in/out port 26 penetrating from the outside into the culture chamber 22 is provided on the right wall of the incubator 10. The carrying in/out port 26 is an opening portion for carrying a container storing a culture and a stacker therethrough into the culture chamber 22, and also carrying them out from the culture chamber 22. On the right side face of the outer case 20 and in the vicinity of the carrying in/out port 26, a carrying in/out door 27 is attached so as to open or close the carrying in/out port 26. The carrying in/out door 27 is provided with a label reader 28 configured to read a label such as an electronic tag or a bar code attached to a culture container, when the culture container is brought into or taken out from the culture chamber 22.

As depicted in FIG. 1, the inner case 21 is provided with an incubator unit 30 to store therein a stacker and other components, and the incubator unit 30 includes a installation stand 40, storage racks 41 and 42, a carrier device 43, and an observation device 44.

Figure 4:
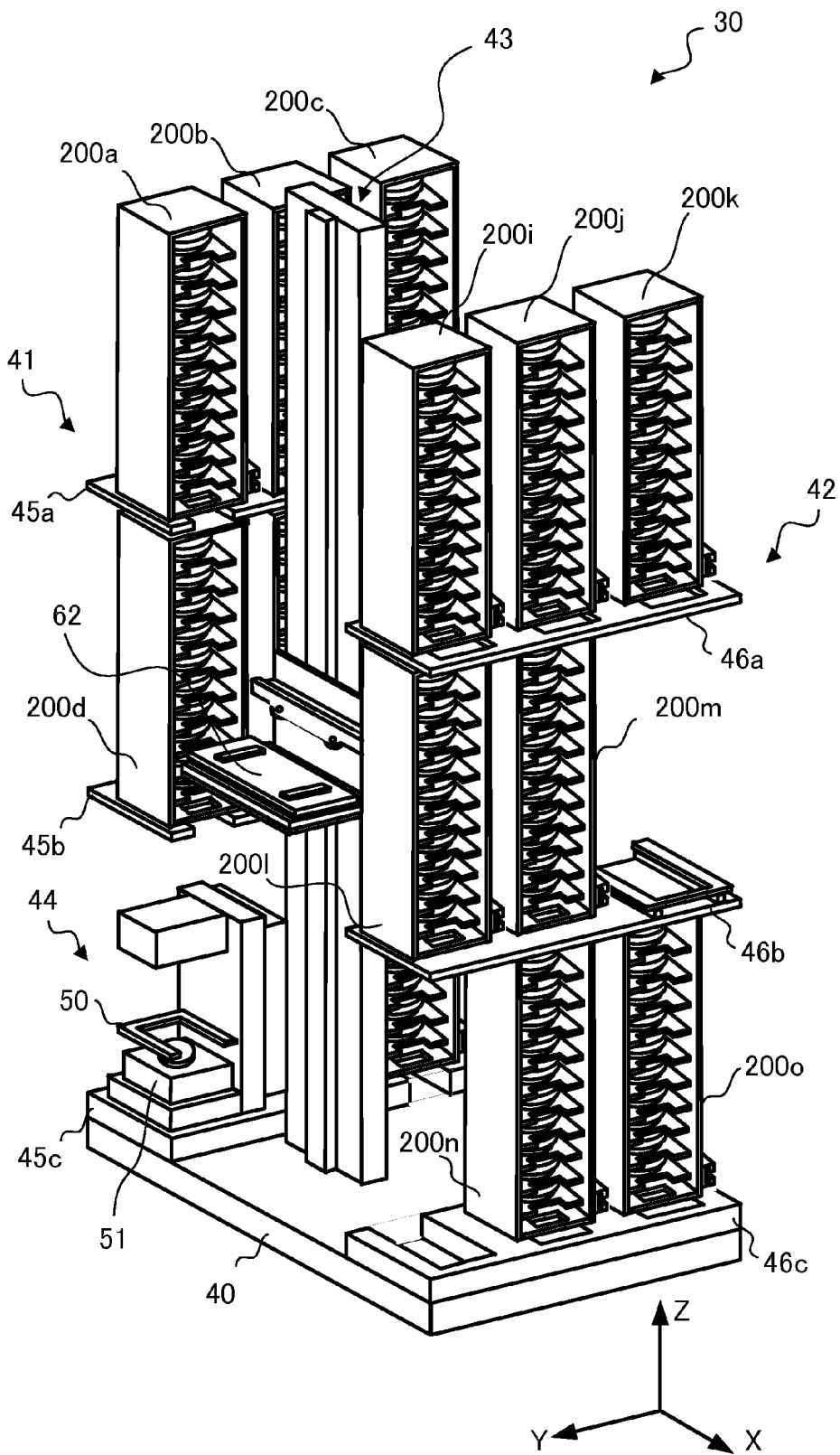
FIG. 4 is a perspective view of an incubator unit 30.

FIG. 4 is a perspective view of the incubator unit 30. The installation stand 40 placed on the inner bottom face of the inner case 21 has installed the storage rack 41 including shelves 45a to 45c, the storage rack 42 including shelves 46a to 46c, and the carrier device 43. In FIG. 4, some of the components constituting the incubator unit 30 are appropriately omitted from FIG. 4 to ease understanding of the relationship among the components of the incubator unit 30.

Although the details will be described later, as depicted in FIG. 3, the storage racks 41 and 42 are provided with storing units 1100 on both sides of the location at which the stacker is set.

==Structure of Container 100 and Tray 110==

Figure 5:
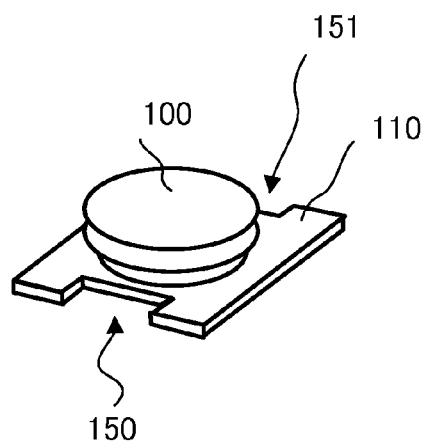
FIG. 5 is a diagram illustrating an example of a container 100 and a tray 110.

FIG. 5 illustrates an example of the container 100 for storing a culture (including liquid such as culture solution), and a tray 110 for placing thereon the container 100. The tray 110 is provided with a hole for holding the container 100 and recesses 150 and 151. Although the details will be described later, the recesses 150 and 151 are used for positioning the tray 110 and restraining the horizontal movement of the tray 110 when the tray 110 is placed on, for example, a carrier table 62 of the carrier device 43 as depicted in FIG. 4.

==Structure of Stacker 200==

Figure 6:
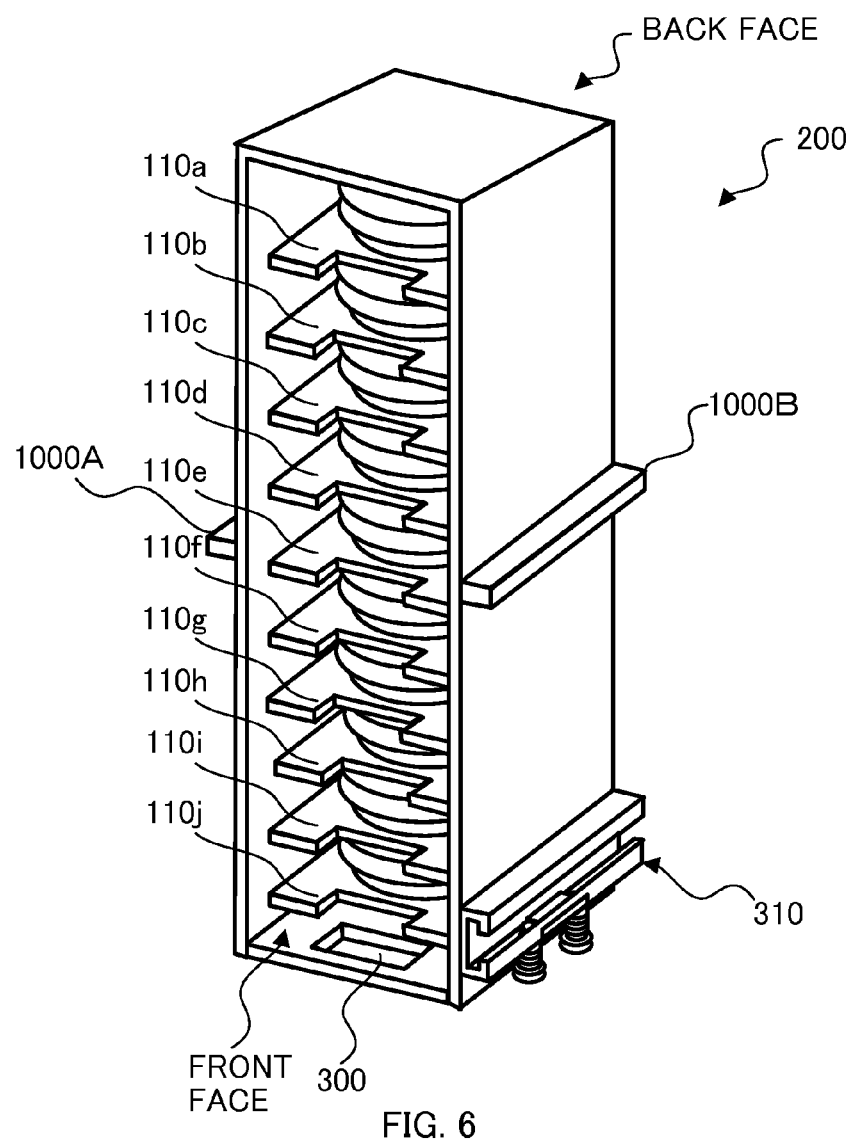
FIG. 6 is a diagram illustrating an example of a stacker 200.

FIG. 6 illustrates an example of a stacker 200 (storage member). The stacker 200 is a case formed into a substantially rectangular parallelepiped shape having opening portions at the front and the back. And, the stacker 200 stores, for example, ten trays 110a to 110j in the vertical direction. Two apertures are arranged at the bottom of the stacker 200 (though only the aperture 300 is depicted). These apertures are used for positioning the stacker 200 and retraining the horizontal movement of the stacker 200 when the stacker 200 is placed on the carrier table 62. A guide receiving mechanism 310 and a pair of stacker guides (first rail members A) 1000 (1000A and 1000B) are attached to the side faces of the stacker 200. The stacker guides 1000A and 1000B are respectively attached to the side faces of the stacker 200 in a horizontally extending manner.

Figure 7:
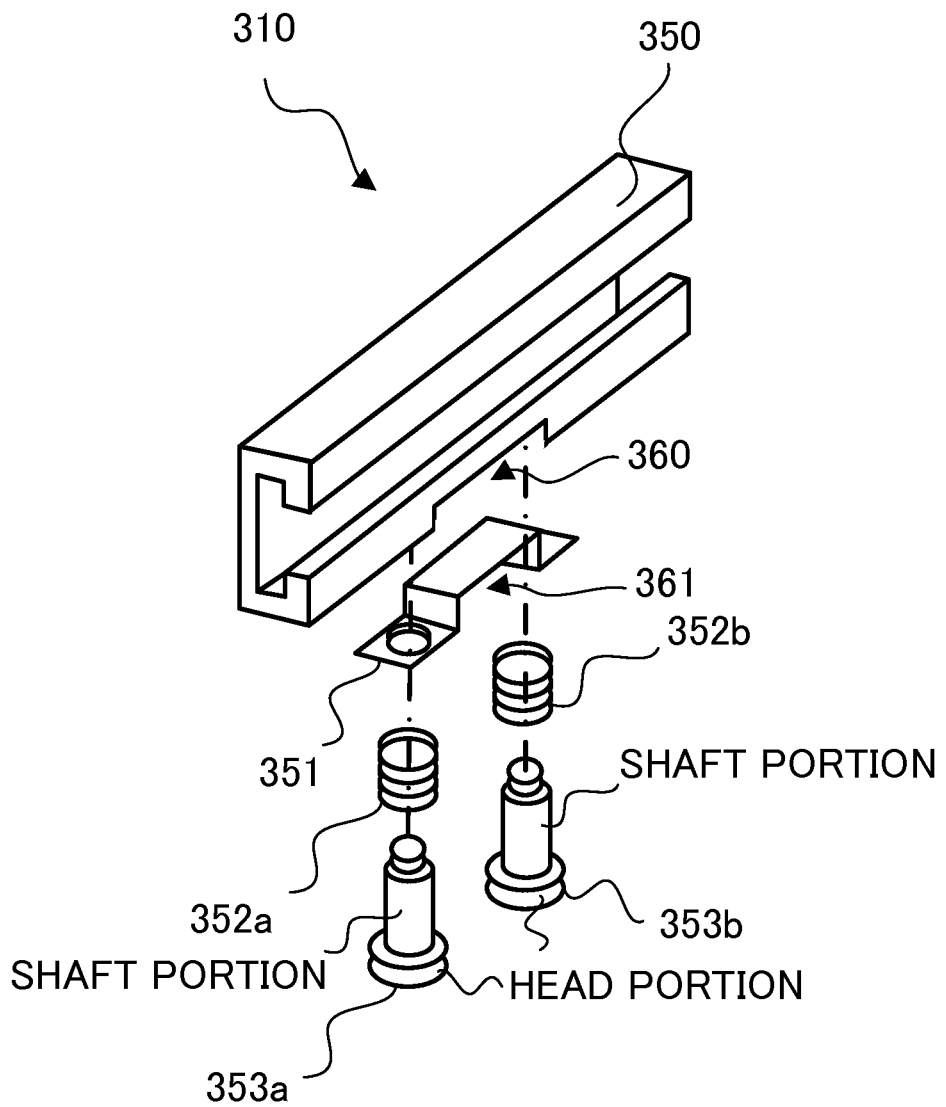
FIG. 7 is an exploded perspective view of a guide receiving mechanism 310.
Figure 8A:
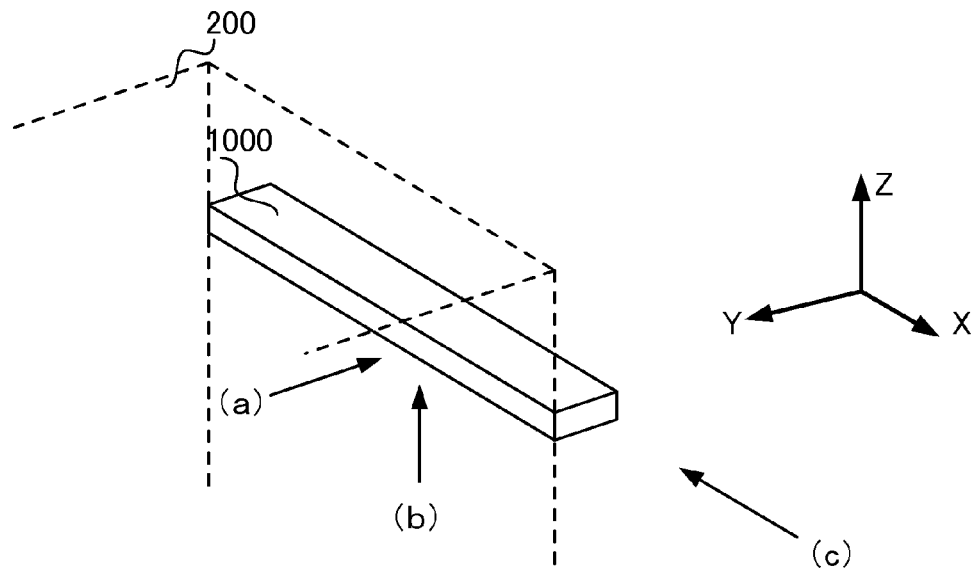
FIG. 8A is a diagram illustrating an example of a stacker guide 1000.
Figure 8B:
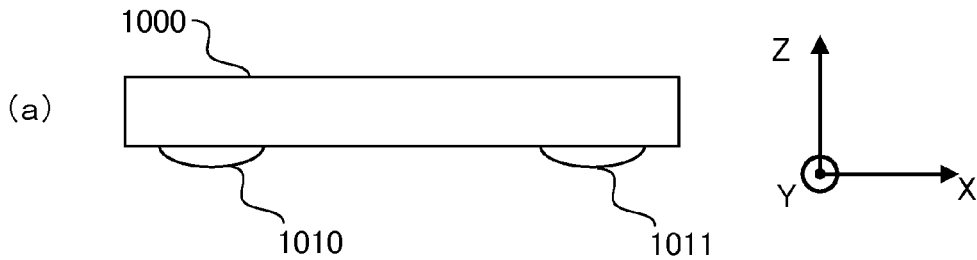
FIG. 8B is a diagram illustrating a stacker guide 1000 viewed from an (a) direction.
Figure 8C:
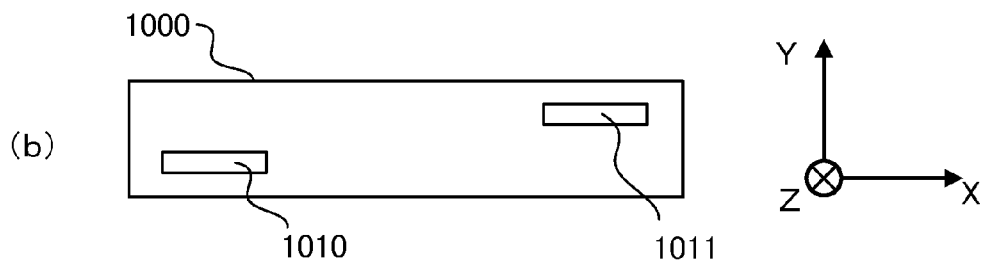
FIG. 8C is a diagram illustrating a stacker guide 1000 viewed from a (b) direction.
Figure 8D:
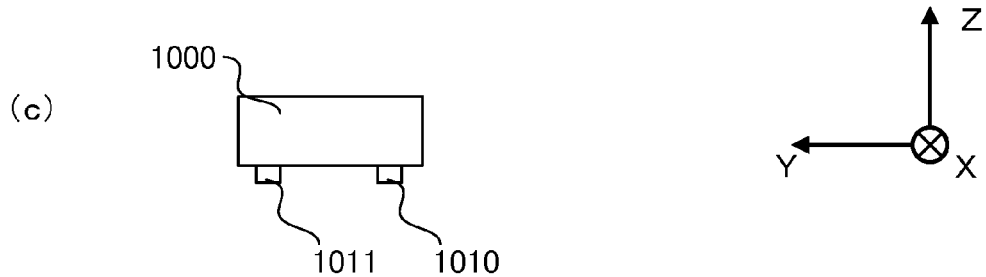
FIG. 8D is a diagram illustrating a stacker guide 1000 viewed from a (c) direction.

The guide receiving mechanism 310 is a member to give an elastic force to the stacker 200 so that the stacker 200 placed on the carrier table 62 is pressed onto the carrier table 62. FIG. 7 is an exploded perspective view of the guide receiving mechanism 310. The guide receiving mechanism 310 includes a guide rail 350, a convex member 351, springs 352a and 352b, and bolts 353a and 353b.

The guide rail 350 is a rail to guide a guide mechanism attached to the carrier table 62 that will be described later. An aperture 360 is arranged in the vicinity of the center on the lower part of the guide rail 350.

The convex member 351 is, for example, a plate formed into a convex shape. A convex portion 361 of the convex member 351 is inserted into the aperture 360 of the guide rail 350 from the bottom side. The convex member 351 is attached to the guide rail 350 using the bolt 353a whose shaft portion is inserted into the spring 352a and the bolt 353b whose shaft portion is inserted into the spring 352b. As a result, when the convex portion 361 of the convex member 351 is pushed from above, the springs 352a and 352b are compressed. Then, a downward force is applied to the guide rail 350 by the elastic forces of the compressed springs 352a and 352b, which results in application of the downward force to the stacker 200 to which the guide rail 350 is attached. Therefore, for example, in the case where the stacker 200 is placed on the carrier table 62, when the convex member 351 is pushed from above and the springs 352a and 352b are compressed, the stacker 200 is pushed onto the carrier table 62.

The stacker guides 1000 are respectively formed on both sides of the stacker 200. When the stacker 200 is stored in the storage rack 41 or 42 from the carrier table 62, the stacker guides 1000 are held and guided by the storing unit guides formed on the storing units 1100 provided on the storage racks 41 and 42.

The stacker guides 1000 are formed at a height substantially equal to a height at which the stacker 200 has the gravity center, thereby being able to effectively restrain swings and vibrations of the stacker 200 when the stacker 200 is stored into the storage rack 41 or 42.

As depicted in FIGS. 8A to 8D, the stacker guide 1000 is formed with, for example, two stacker guide convex portions (first and second convex portions) 1010 and 1011 on the face thereof in contact with the storing unit guide. The stacker guide convex portions 1010 and 1011 are formed at the positions spaced apart from each other in the direction, (X-axis direction) in which the stacker 200 is moved when the stacker 200 is stored into either of the storage racks 41 and 42, and are also spaced apart from each other in the horizontal direction (Y-axis direction) vertical to the direction of such movement.

The stacker guide convex portions 1010 and 1011 are respectively fitted with two grooves or apertures (first and second fitting portions) that are formed on the storing unit guides of the storing units 1100 in a state where the stacker 200 is stored in the storage location of the storage rack 41 or 42 by the carrier table 62. As a result, the stacker 200 is fixed at the predetermined position in the storage rack 41 or 42.

The stacker guide convex portions 1010 and 1011 are formed in a semicircle or a semi-ellipse shape drawn along the movement direction of the stacker 200 when the stacker 200 is stored into the storage rack 41 or 42. As such, shaping the stacker guide convex portions 1010 and 1011 into a round shape enables restraint of the impact generated when the stacker guide convex portions 1010 and 1011 are fitted with the grooves formed in the storing unit guide.

==Structure of Storing Unit 1100==

Figure 9:
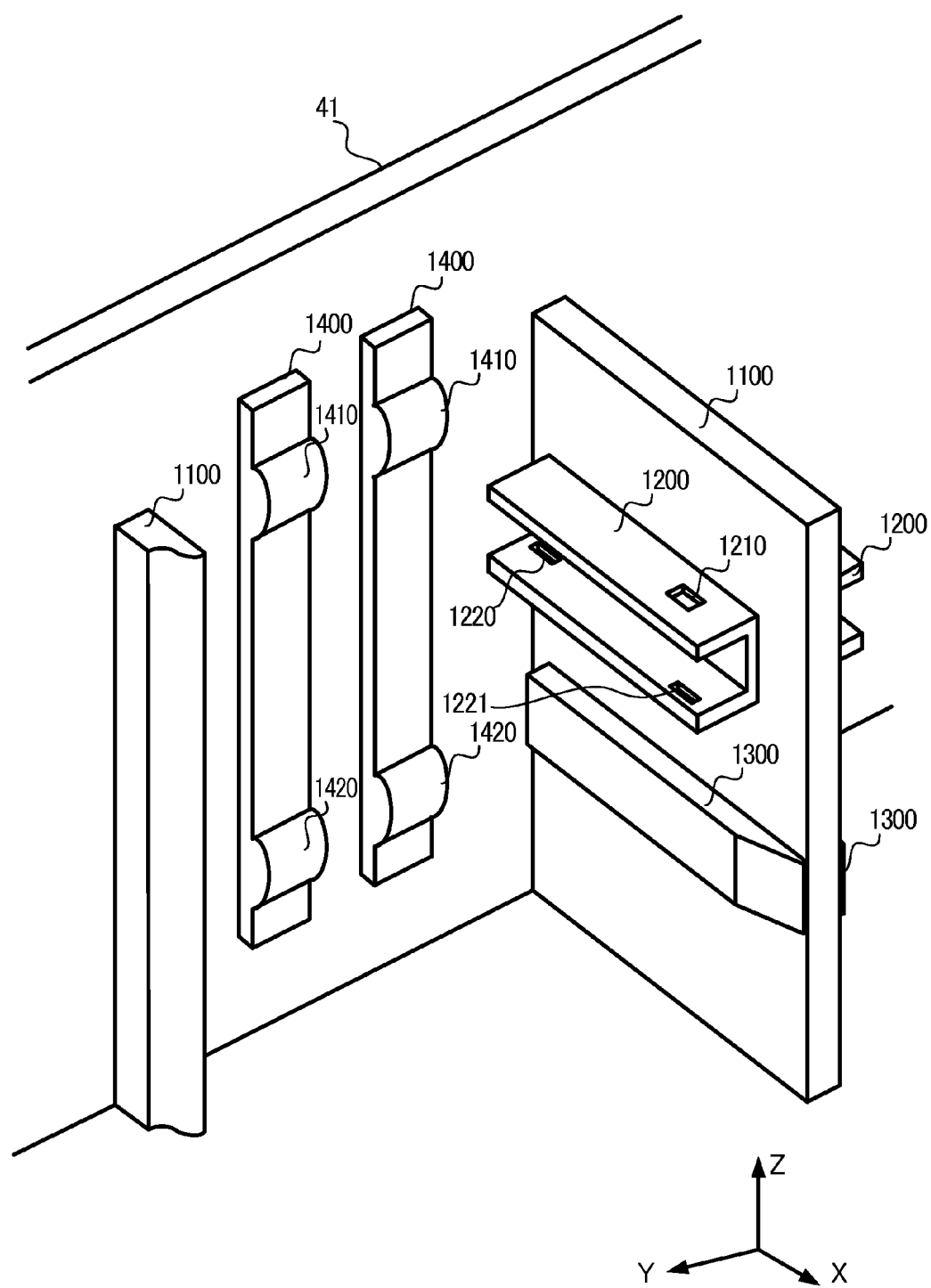
FIG. 9 is a diagram illustrating an example of a storing unit 1100.

On the other hand, the storing units 1100 provided on the storage racks 41 and 42 will be described with reference to FIG. 9. Although FIG. 9 depicts the storing units 1100 provided on the storage rack 41, the storing units 1100 provided on the storage rack 42 are similar thereto.

In the storage racks 41 and 42, the storing units 1100 are the walls provided on both sides of the location at which the stacker 200 is stored, and each include a storing unit guide (second rail member B) 1200 and a leading guide 1300.

The storing units 1100 are arranged on the storage racks 41 and 42 at intervals substantially equal to the width of the stacker 200. Thereby, a compartment is formed to store the stacker 200 between the two storing units 1100 adjacent to each other. That is, the pair of storing units 1100 is provided so as to be respectively opposed to the side faces of the stacker 200 in a state where the stacker 200 is stored in the storage rack 41 or 42. Each of the pair of storing units 1100 includes the storing unit guide 1200, extending along the horizontal direction, on the side opposed to the stacker guide 1000 in a state where the stacker 200 is stored in the storage rack 41 or 42.

The storing unit guide 1200 is formed on the storing unit 1100 on each of the sides sandwiching the compartment whereto the stacker 200 is stored, and is a rail supporting the stacker guide 1000 attached on each of the sides of the stacker 200. The storing unit guide 1200 extends in the storage direction of the stacker 200 on the wall face of the storing unit 1100. Therefore, when the carrier table 62 having the stacker 200 placed thereon is moved toward the storage rack 41 or 42, the pair of storing unit guides 1200 supports the pair of stacker guides 1000, respectively, and the stacker 200 is guided to the storage rack 41 or 42.

The storing unit guide 1200 according to an embodiment of the present invention is structured such that two parallel rails, extending in the storage direction of the stacker 200 in the up and down direction, are arranged on the wall face of the storing unit 1100. More specifically, the storing unit guide 1200 has a U-shape, for example, so as to be equipped with the two rails integrated into one piece.

Out of the two parallel rails constituting the storing unit guide 1200, the lower rail (hereinafter, referred to as "support rail") supports the stacker guide 1000 when the stacker 200 is stored in the storage rack 41 or 42.

Out of the two parallel rails constituting the storing unit guide 1200, the upper rail (hereinafter, referred to as "guide rail") guides the stacker guide 1000 so as to prevent the stacker guide 1000 from being derailed from the support rail. The guide rail is provided in the storing unit guide 1200, thereby being able to effectively restrain swings and vibrations generated when the stacker 200 is stored into the storage rack 41 or 42.

The support rail of the storing unit guide 1200 is provided with the grooves (first and second fitting portions) 1220 and 1221 on the face in contact with the stacker guide 1000. The grooves 1220 and 1221 may be apertures such as holes.

The grooves 1220 and 1221 are formed at positions at which the grooves 1220 and 1221 are respectively opposed to the stacker guide convex portions 1010 and 1011 formed on the stacker guide 1000 when the stacker 200 has been completely stored in the storage rack 41 or 42.

When the stacker 200 has been completely stored in the storage rack 41 or 42, the stacker guide convex portions 1010 and 1011 are respectively fitted with the grooves 1220 and 1221, thereby, fixing the stacker 200 at the predetermined position in the storage rack 41 or 42.

The guide rail of the storing unit guide 1200 is provided with a roller attachment portion 1210.

The roller attachment portion 1210 is an aperture for attaching a roller, which will be described later, to the storing unit guide 1200. The roller attached to the storing unit guide 1200 is rotatable and acts so as to elastically bias the stacker guide 1000 toward the support rail when the stacker 200 is stored into the storage rack 41 or 42. Thus, occurrence of inclination and impact is prevented in the stacker 200 when the stacker guide convex portions 1010 and 1011 are fitted with the grooves 1220 and 1221, thereby being able to prevent breakage and falling of the container 100 loaded on the stacker 200 and a spill of the culture solution.

The leading guide 1300 is a board for guiding the stacker 200 so that the stacker guide 1000 does not collide with the storing unit guide 1200 when the stacker 200 is moved from the carrier table 62 to the storage rack 41 or 42. The leading guide 1300 is in a flat plate shape, and is formed such that the closer to the end side thereof on which the stacker 200 is stored in and taken out from the storage rack 41 or 42, the thinner the board thickness becomes. When the stacker 200 is stored in the storage rack 41 or 42, the leading guide 1300 guides the stacker 200, thereby being able to prevent collision associated with misalignment between the stacker guide 1000 and the storing unit guide 1200 and generation of vibration and impact in the stacker 200.

As depicted in FIG. 9, the storage rack 41 (storage rack 42 is similar thereto) is provided with a vertical sliding unit 1400. The vertical sliding unit 1400 is a board having a rectangular parallelepiped shape, and is formed such that first and second protruding portions 1410 and 1420 are arranged in line in a longitudinal direction. In an example depicted in FIG. 9, the two vertical sliding units 1400 are provided, with their longitudinal direction set along the vertical direction, on the wall face of the storage rack 41 that is a rear front face in the compartment sandwiched by the two storing units 1100 adjacent each other.

The vertical sliding units 1400 are formed such that the first and the second protruding portions 1410 and 1420 are in contact with the front face of the stacker 200 facing toward the storage direction of the stacker 200 when the stacker guide convex portions 1010 and 1011 are fitted with the grooves 1220 and 1221. Therefore, in the case where the stacker 200 is moved from the carrier table 62 to the storage rack 41 or 42, when the stacker guide convex portions 1010 and 1011 are fitted with the grooves 1220 and 1221, the vertical sliding units 1400 act so as to restrain such movement of the stacker 200 as to incline toward the movement direction (X-axis direction). Thus, generation of inclination and impact in the stacker 200 can be prevented when the stacker guide convex portions 1010 and 1011 are fitted with the grooves 1220 and 1221, thereby being able to prevent breakage and falling of the container 100 loaded on the stacker 200 and a spill of the culture liquid.

The storage rack 41 depicted in FIGS. 1 and 4 is a rack to store the observation device 44 and a plurality of stackers 200, and is attached to the installation stand 40 such that the storage rack 41 is arranged closer to the left side wall face of the inner case 21. The storage rack 41 is attached with the three shelves 45a to 45c in the vertical direction (Z-axis direction). Further, as described above, each of the shelves 45a to 45c is provided with the storing units 1100 on the both sides of the location where the stacker 200 is to be placed.

Figure 10:
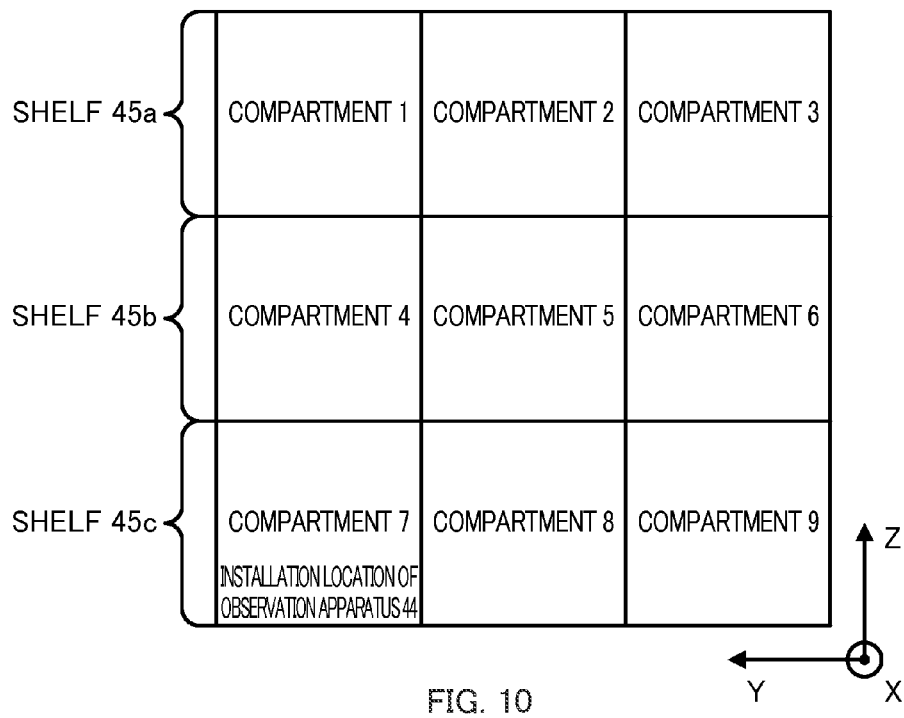
FIG. 10 is a diagram illustrating compartments of a storage space of a storage rack 41.

In an embodiment of the present invention, as depicted in FIG. 10, the storage space of the storage rack 41 is partitioned into nine compartments constituted by compartments 1 to 9. Each of the compartments has a capacity enough to store the stacker 200 or the observation device 44. The storage space of the shelf 45a is allocated to three compartments of compartments 1 to 3. The storage space of the shelf 45b is allocated to three compartments of compartments 4 to 6. The storage space of the shelf 45c is allocated to three compartments of compartments 7 to 9. The compartment 7 on the front door 25 side of the shelf 45c is a compartment in which the observation device 44 is installed. When a culture is observed, the tray 110 having container 100, containing the culture to be observed, placed thereon is set in the observation device 44. Thus, no stacker 200 is set in the compartment 7. Consequently, out of the storing spaces of the storage rack 41, the compartments 1 to 6, 8, and 9 are capable of having the stackers 200 set therein.

Then, the storing units 1100 are set on the sides of the compartments 1 to 6, 8, and 9 each capable of having the stacker 200 set therein.

On the other hand, the storage rack 42 is a rack to store a plurality of stackers 200 similarly to the storage rack 41, and is attached to the installation stand 40 such that the storage rack 42 is arranged closer to the right side wall face of the inner case 21. The storage rack 42 is also attached with the three shelves 46a to 46c in the vertical direction. Each of the shelves 46a to 46c is provided with the storing units 1100 on the both sides of the location where the stacker 200 is to be placed. The shelves 45a to 45c are attached at the heights equal to those at which the shelves 46a to 46c are attached.

Figure 11:
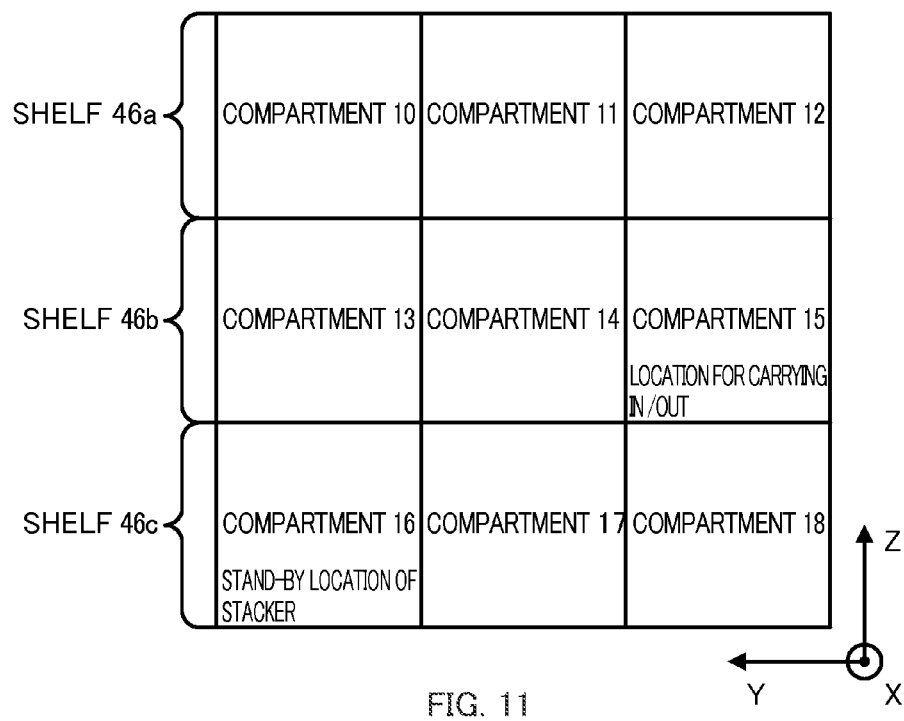
FIG. 11 is a diagram illustrating compartments of a storage space of a storage rack 42.

As depicted in FIG. 11, the storage space of the storage rack 42 is partitioned into nine compartments constituted by compartments 10 to 18, similarly to the storage rack 41. The storage space of the shelf 46a is allocated to three compartments 10 to 12. The storage space of the shelf 46b is allocated to three compartments 13 to 15. The storage space of the shelf 46c is allocated to three compartments 16 to 18. The compartment 15, which is opposed to the carrying in/out port 26 for carrying the stackers 200 into or out from the incubator 10 and is closest to the carrying in/out port 26, is the compartment for the stacker 200 to be temporarily set therein when the stacker 200 is carried into or out. The compartment 16, which is opposed to the compartment 7 having the observation device 44 set therein, is the compartment for the stacker 200 having the container 100, containing a culture, stored therein, to temporarily stand by when a culture is observed using the observation device 44. The stand-by compartment for the stacker 200 to be observed is set to be the compartment 16 opposed to the compartment 7, thereby, for example, being able to reduce the distance for the carrier device 43 to carry, to the observation device 44, the container 100 stored in the stacker 200 in the compartment 16.

In the storage rack 42, the compartments 10 to 18 are capable of having the stackers 200 set therein. The storing units 1100 are set on the sides of the compartments 10 to 18 each capable of having the stacker 200 set therein.

In an embodiment of the present invention, the storage racks 41 and 42 each are provided with three shelves in a three-story structure. However, the rack structure is not limited thereto, and may be a one-story structure, for example. In this case, the installation stand 40 may also act as a shelf.

The carrier device 43 depicted in FIG. 1 is a device configured to carry the tray 110 and the stacker 200. Although the details of the carrier device 43 will be described later, the carrier device 43 is attached so as to be movable on a rail 47 that is attached to the installation stand 40 on the surface thereof along the Y-axis direction. The rail 47 is attached at a position between the storage racks 41 and 42.

The observation device 44 is an apparatus for observing a culture stored in the container 100, and includes an observation stand 50 and a camera 51.

The container 100 carried by the carrier device 43 is placed on the observation stand 50. The observation stand 50 is provided with motors to move the observation stand 50 in each of the X-axis, the Y-axis, and the Z-axis directions so that shooting of the container 100 by the camera 51 can be facilitated. The camera 51 is configured to shoot a culture of the container 100 to acquire a picture or an image.

<<Details of Carrier Device 43>>

Figure 12:
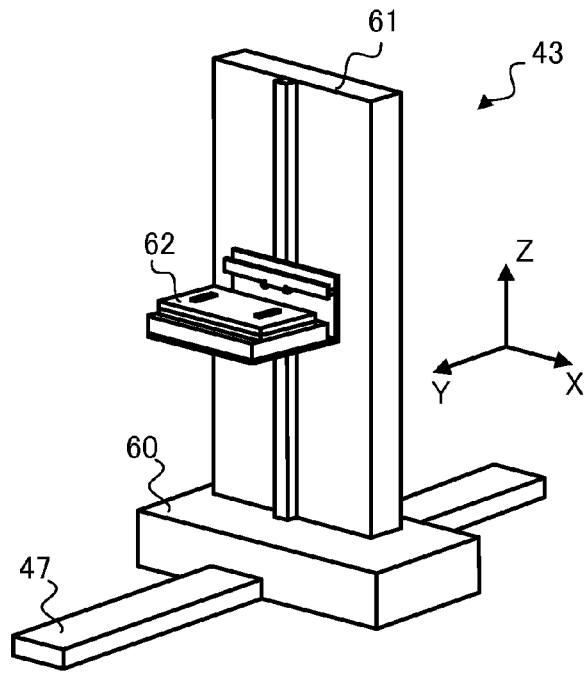
FIG. 12 is a perspective view of a carrier device 43.

The details of the carrier device 43 will be described. As depicted in FIG. 12, the carrier device 43 includes a slide device 60, a rail member 61, and the carrier table 62. FIG. 12 is a perspective view of the carrier device 43.

The slide device 60 is attached to the rail 47 along the Y-axis direction in a movable manner. A motor (for Y-axis) provided inside the slide device 60 rotates, thereby moving (sliding) the slide device 60 on the rail 47. Further, the rail member 61 is attached to the slide device 60 along the vertical direction (Z-axis direction). The carrier table 62 is attached to the rail member 61 so as to be movable along the Z-axis direction. A motor (for Z-axis) provided inside the slide device 60 rotates, thereby moving (sliding) the carrier table 62 in the Z-axis direction. Thus, the slide device 60 and the carrier table 62 function as a carrying mechanism.

Figure 13:
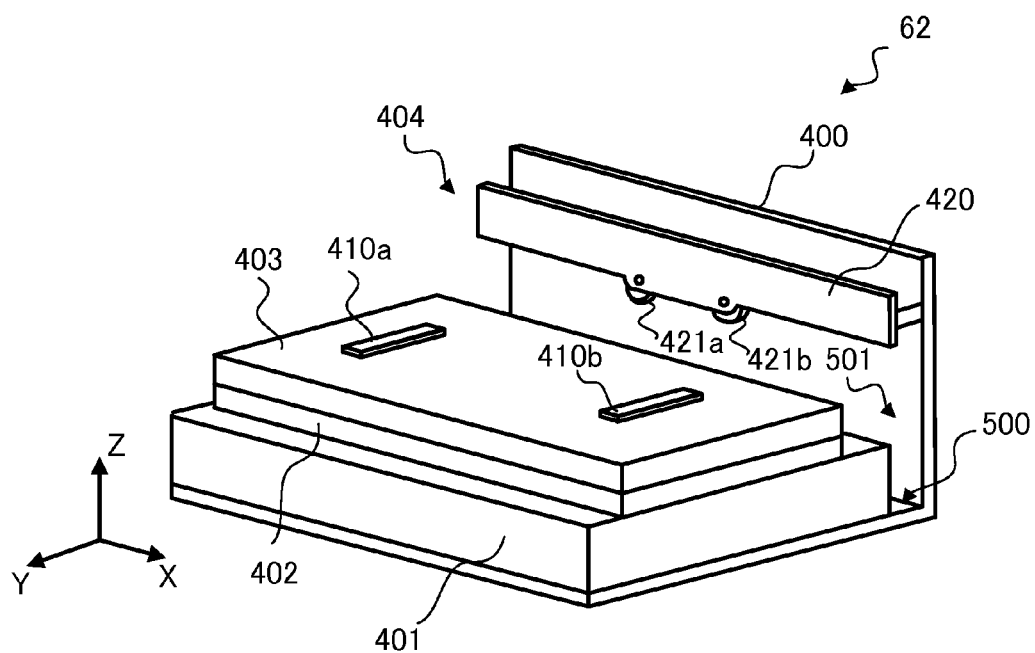
FIG. 13 is a perspective view of a carrier table 62.
Figure 14:
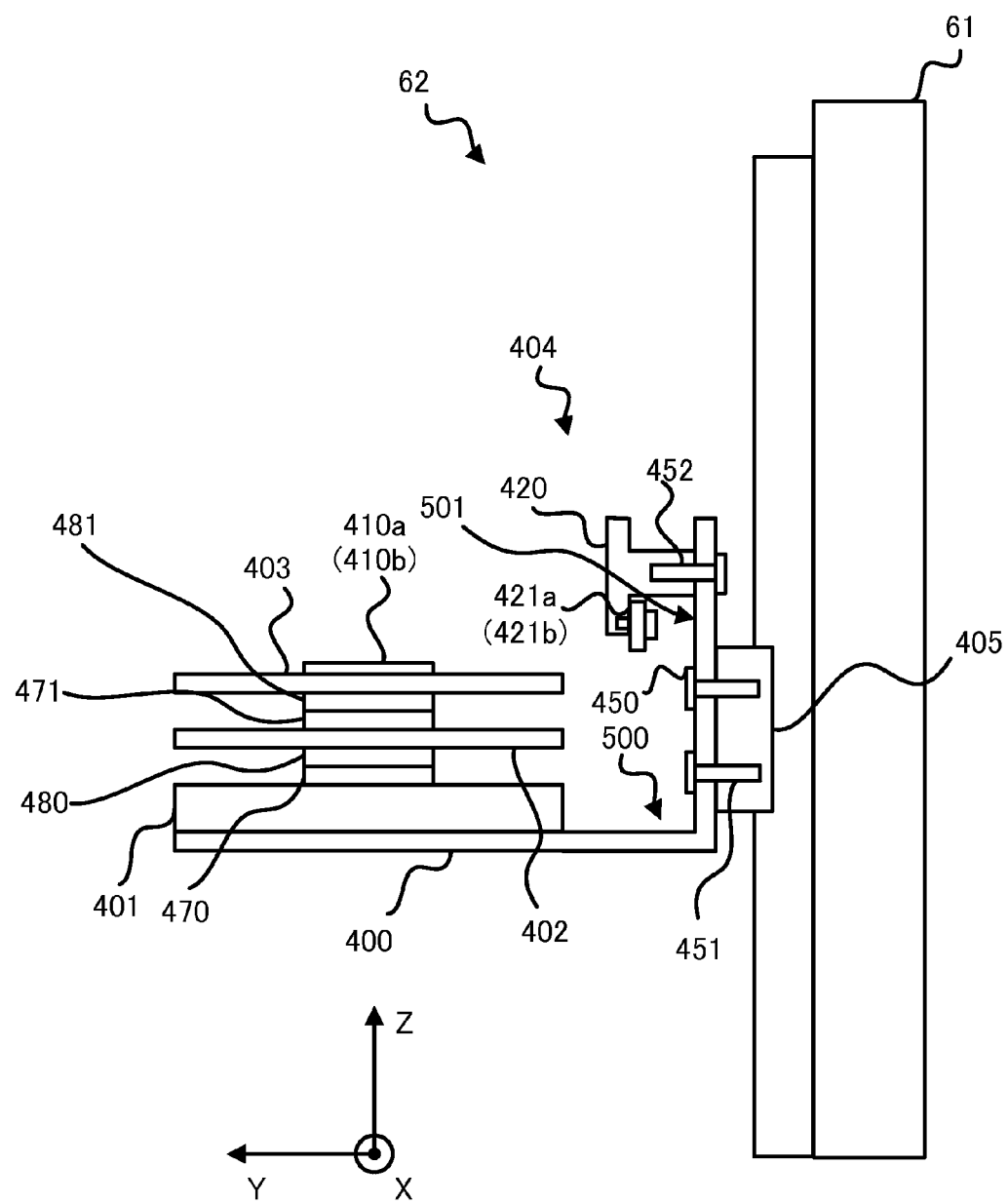
FIG. 14 is a perspective side view of a carrier table 62 viewed from a +X-axis direction.

FIG. 13 is a perspective view of the carrier table 62. FIG. 14 is a perspective side view of the carrier table 62 when viewed from the +X-axis direction. In FIG. 13, some components are not depicted for convenience' sake. Further, although for example, e.g., slide plates 402 and 403 are depicted to be in close contact with each other, a space is provided between the boards in practice so that each of the boards can slide.

The carrier table 62 includes a base plate 400, a stand 401, the slide plates 402 and 403, a guide mechanism 404, and a slider 405. The base plate 400 and the stand 401 correspond to a base.

The base plate 400 is a plate formed in an L-shape, and is attached to the slider 405 with bolts 450 and 451 such that a face 500 of the base plate 400 will be horizontal. The slider 405 is attached to the rail member 61 in a manner movable in the Z-axis direction. The motor (for Z-axis) provided inside the slide device 60 rotates, to move (slide) the slider 405 in the Z-axis direction. The stand 401 is set on the face 500 of the base plate 400, and a rail 470 along the X-axis direction is attached to the stand 401 on its surface.

A slider 480 attached to the bottom face of the slide plate 402 is attached thereto in a manner movable in the ±X directions on the rail 470 of the stand 401. Therefore, a motor (for X-axis) provided inside the carrier table 62 rotates to move (slide) the slide plate 402 on the stand 401 in the ±X directions. A rail 471 along the X-axis direction is attached to the slide plate 402 on its surface.

The tray 110 or the stacker 200 is selectively placed on the slide plate 403 (pedestal). A slider 481 attached to the slide plate 403 on the bottom face thereof is attached so as to be movable on the rail 471 in the ±X directions. Therefore, the motor (for X-axis) provided inside the carrier table 62 rotates, to move (slide) the slide plate 403 on the slide plate 402 in the ±X directions. Therefore, for example, the slide plates 402 and 403 function as a slide mechanism.

When the tray 110 is placed on the slide plate 403, the slide plates 402 and 403 are moved in the X-axis direction, thereby being able to store the tray 110 in the stacker 200 stored in the storage rack 41 or 42. When the stacker 200 is placed on the slide plate 403, the slide plates 402 and 403 are moved in the X-axis direction, thereby being able to store the stacker 200 in the storage rack 41 or 42.

Figure 15:
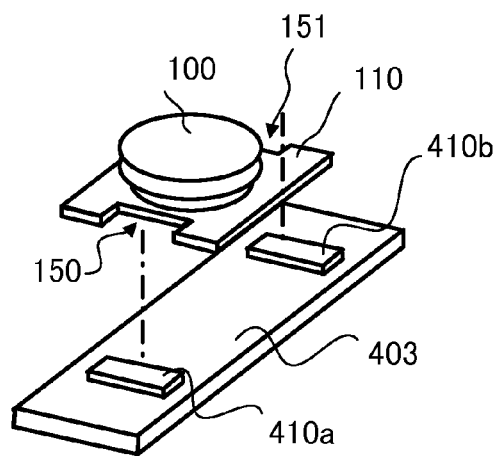
FIG. 15 is a diagram illustrating a relationship between a tray 110 and a slide plate 403.
Figure 16:
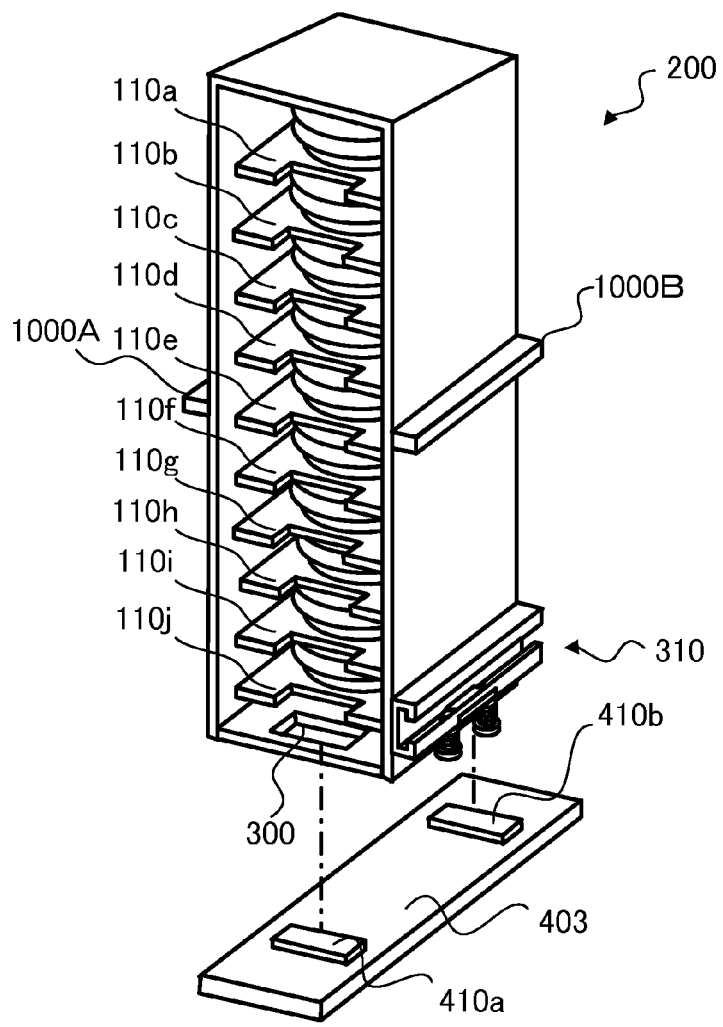
FIG. 16 is a diagram illustrating a relationship between a stacker 200 and a slide plate 403.

Convex portions 410a and 410b are formed on the surface of the slide plate 403. When the tray 110 is placed on the slide plate 403, as depicted in FIG. 15, the convex portions 410a and 410b are respectively fitted with the recesses 150 and 151 of the tray 110. Whereas, when the stacker 200 is placed on the slide plate 403, as depicted in FIG. 16, the convex portion 410a is fitted with the aperture 300 on the bottom face of the stacker 200 and the convex portion 410b is fitted with the aperture not shown on the bottom face of the stacker 200. As a result, when the tray 110 or the stacker 200 is placed on the slide plate 403, the horizontal movement of the tray 110 or the stacker 200 is restricted. As such, the slide plate 403 has such a shape that positions the tray 110 or the stacker 200 and that restricts the horizontal movement thereof.

The guide mechanism 404 depicted in FIGS. 13 and 14 is structured such that the guide receiving mechanism 310 on the stacker 200 side is guided by a guide member 420 when the slide plate 403 having the stacker 200 placed thereon is moved from the storage rack 41 or 42 to the stand 401. The guide mechanism 404 includes the guide member 420 and guide rollers 421a and 421b.

The guide rollers 421a and 421b are attached in the vicinity of the center of the guide member 420. The guide member 420 is attached to a face 501 of the base plate 400 with a bolt 452 such that the guide member 420 and the guide rollers 421a and 421b are guided by the guide receiving mechanism 310 on the stacker 200 side when the slide plate 403 having the stacker 200 placed thereon is slid. The guide member 420 is attached at a position at which the guide rollers 421a and 421b roll along the guide receiving mechanism 310 when the slide plate 403 is slid.

==Operations of Guide Receiving Mechanism 310 and Guide Mechanism 404==

Figure 17:
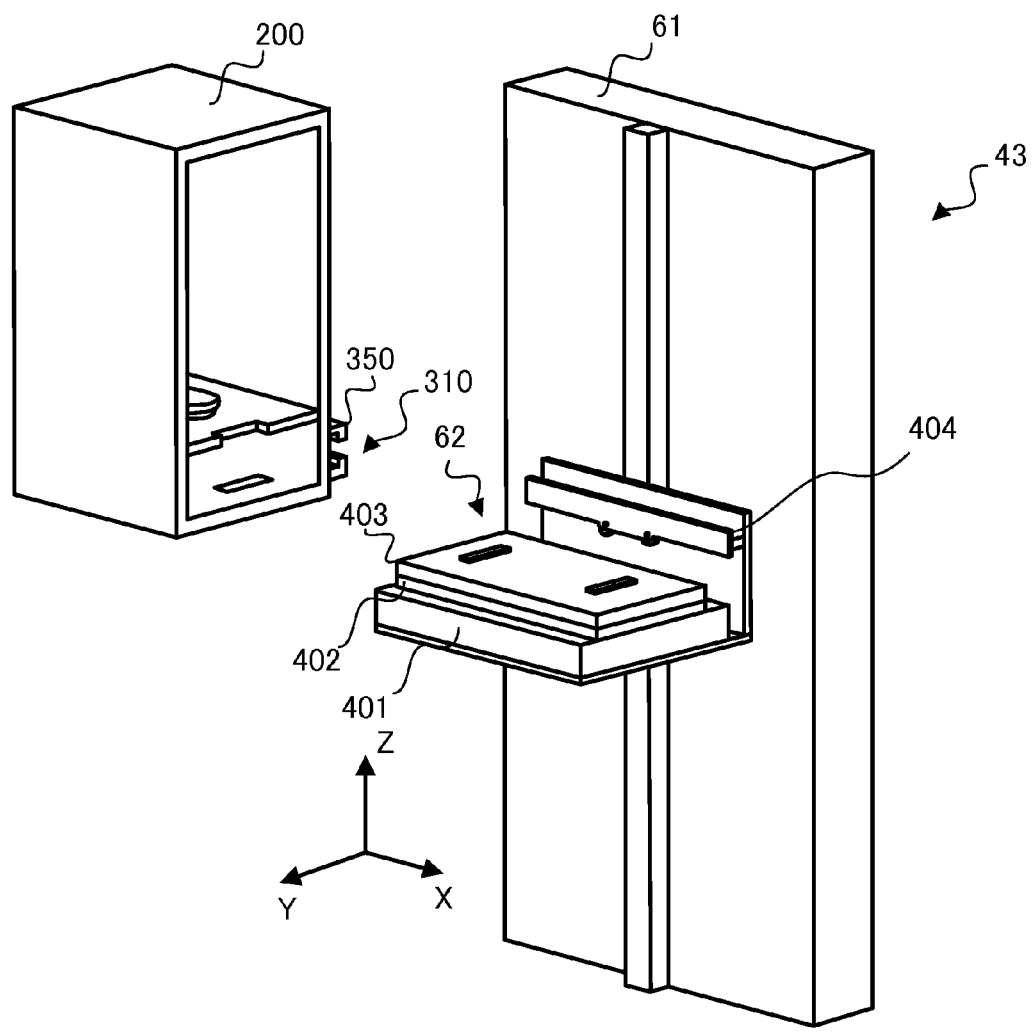
FIG. 17 is a perspective view of a stacker 200 before being placed on a carrier table 62.

Operations of the guide receiving mechanism 310 on the stacker 200 side and the guide mechanism 404 on the carrier table 62 side will be described with reference to FIGS. 17 and 18A to 18C. FIG. 17 is a perspective view illustrating a state before the stacker 200 is placed on the carrier table 62.

Figure 18A:
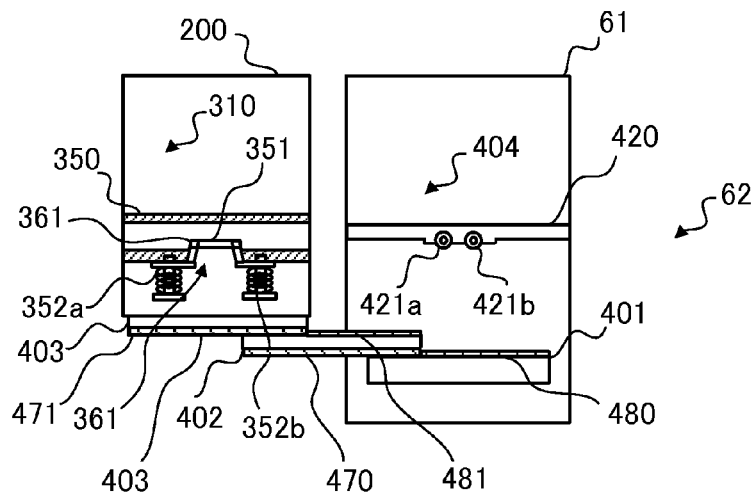
FIG. 18A is a schematic diagram for describing an operation of a guide receiving mechanism 310 and a guide mechanism 404.
Figure 18B:
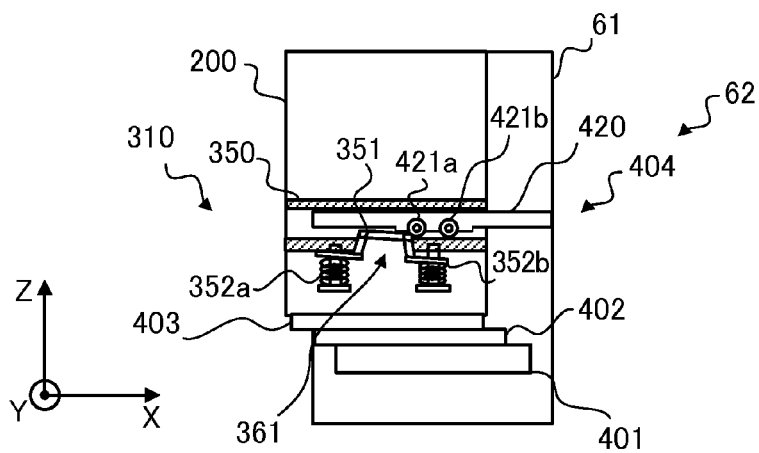
FIG. 18B is a schematic diagram for describing an operation of a guide receiving mechanism 310 and a guide mechanism 404.
Figure 18C:
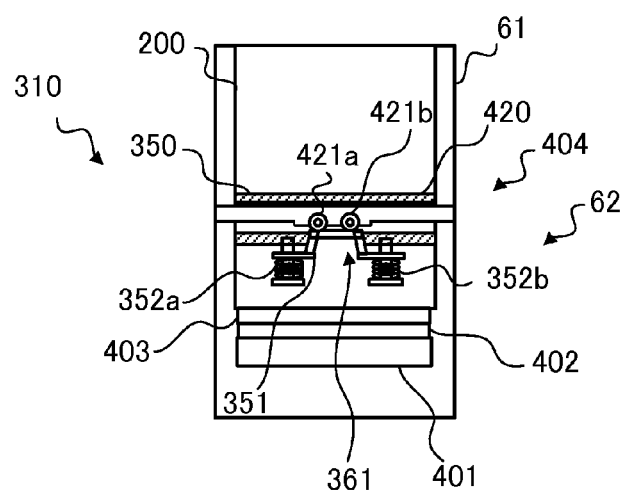
FIG. 18C is a schematic diagram for describing an operation of a guide receiving mechanism 310 and a guide mechanism 404.

FIGS. 18A to 18C are schematic diagrams describing operations of the guide receiving mechanism 310 and the guide mechanism 404. In FIGS. 17 and 18A to 18C, some components are not depicted, for convenience' sake.

In the state depicted in FIG. 17, the carrier device 43 moves the slide plates 402 and 403 in the horizontal direction so that the stored stacker 200 is placed on the slide plate 403 of the carrier table 62. Specifically, the slide plates 402 and 403 are slid in the −X direction from the state where the slide plates 402 and 403 are not slid at all, or in other words, the state depicted in FIG. 17 where the slide plates 402 and 403 are completely stored (hereinafter, the position of the slide plates in this state will be referred to as "predetermined position A").

As depicted in FIG. 18A, when the stacker 200 is placed on the slide plate 403, the carrier device 43 slides the slide plates 402 and 403 in the +X direction so that the guide member 420 is guided along the guide rail 350. Specifically, the slider 480 on the bottom face of the slide plate 402 slides on the rail 470 that is attached to the stand 401. The slider 481 on the bottom face of the slide plate 403 slides on the rail 471 that is attached to the slide plate 402. Hereinafter, a description will be made with for example, e.g., the slider 48 being omitted, for convenience' sake.

As depicted in FIG. 18B, when the slide plates 402 and 403 are slid in the +X direction, the guide member 420 enters the guide rail 350, and the guide roller 421a rolls along the guide rail 350, rolls on the convex portion 361 of the convex member 351, and then starts to push the convex member 351 downward. As a result, the convex member 351 is lowered and the spring 352b is gradually compressed.

Thereafter, as depicted in FIG. 18C, when the slide plates 402 and 403 further slide in the +X direction and have been stored, the guide roller 421b also rolls to roll on the convex portion 361, and pushes the convex member 351. As a result, the springs 352a and 352b both are compressed, and such elastic forces cause the guide rail 350 to receive the downward forces through the bolts 353a and 353b. Thereby, the stacker 200 is pushed onto the slide plate 403.

In an embodiment of the present invention, it is assumed, for example, that the guide receiving mechanism 310 and the guide mechanism 404 are designed such that both of the guide rollers 421a and 421b roll on the convex portion 361 and push the convex member 351 in a state where the slide plates 402 and 403 is stored at the predetermined position A. Therefore, when the slide plate 403 is moved to the predetermined position A, the stacker 200 is securely pushed onto the slide plate 403.

==Operations of Stacker Guide 1000 and Storing Unit Guide 1200==

Figure 19:
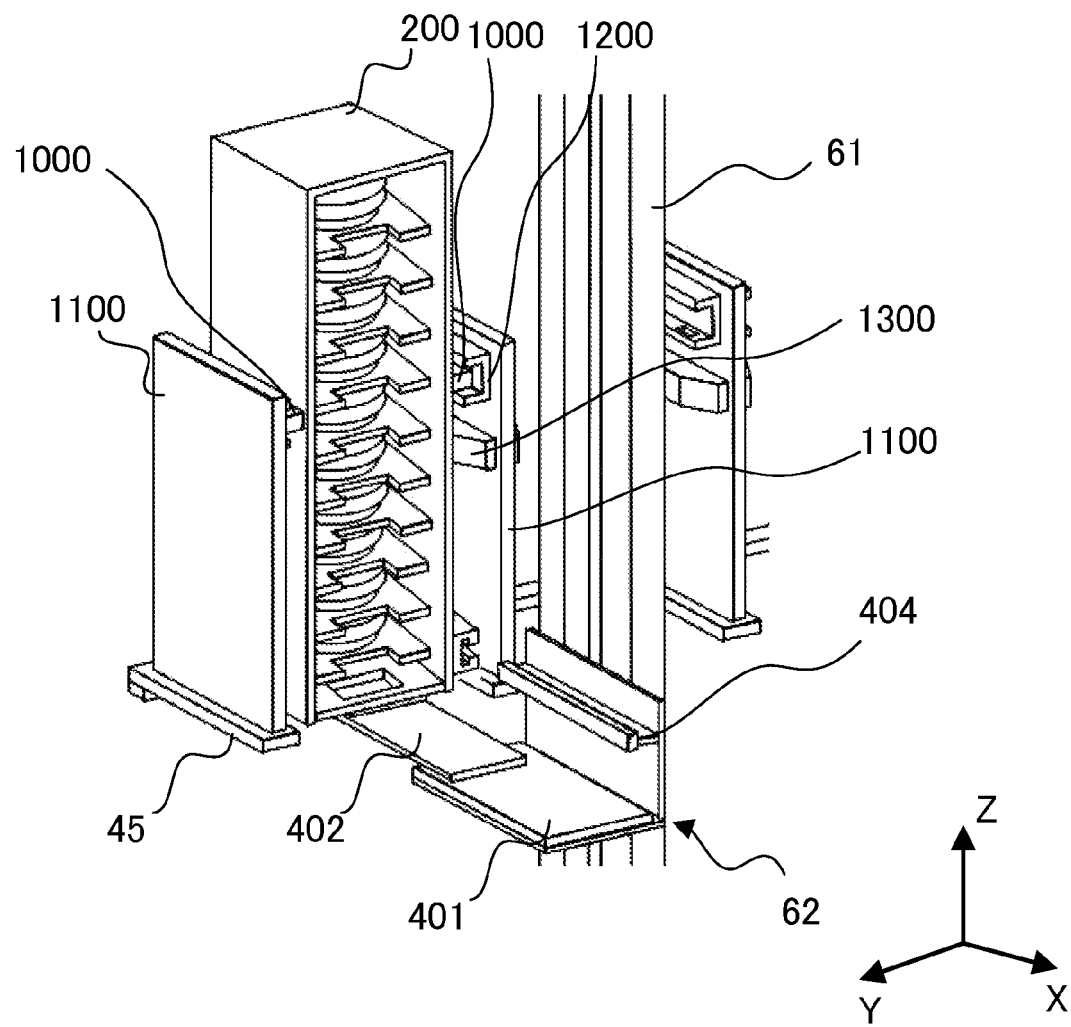
FIG. 19 is a diagram illustrating a state where a stacker 200 is stored in a storage rack 41.
Figure 20A:
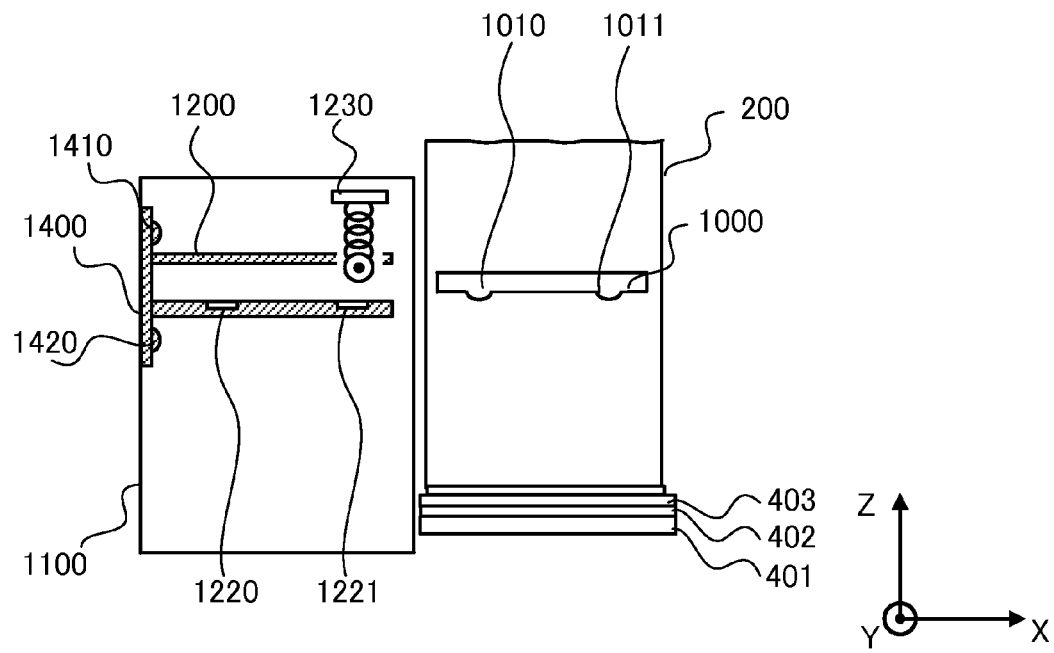
FIG. 20A is a schematic diagram for describing an operation of a stacker guide 1000 and a storing unit guide 1200.
Figure 20B:
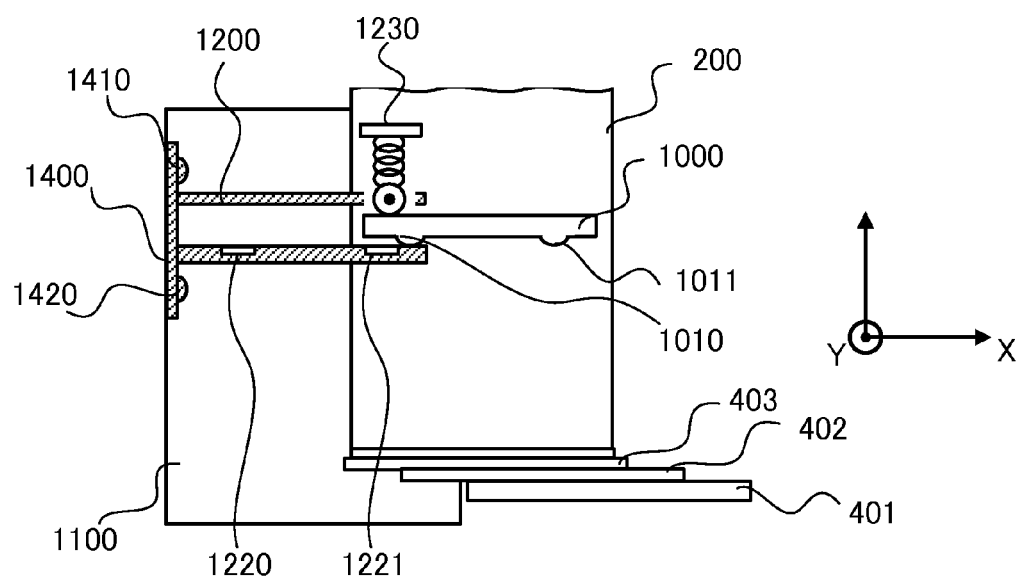
FIG. 20B is a schematic diagram for describing an operation of a stacker guide 1000 and a storing unit guide 1200.
Figure 20C:
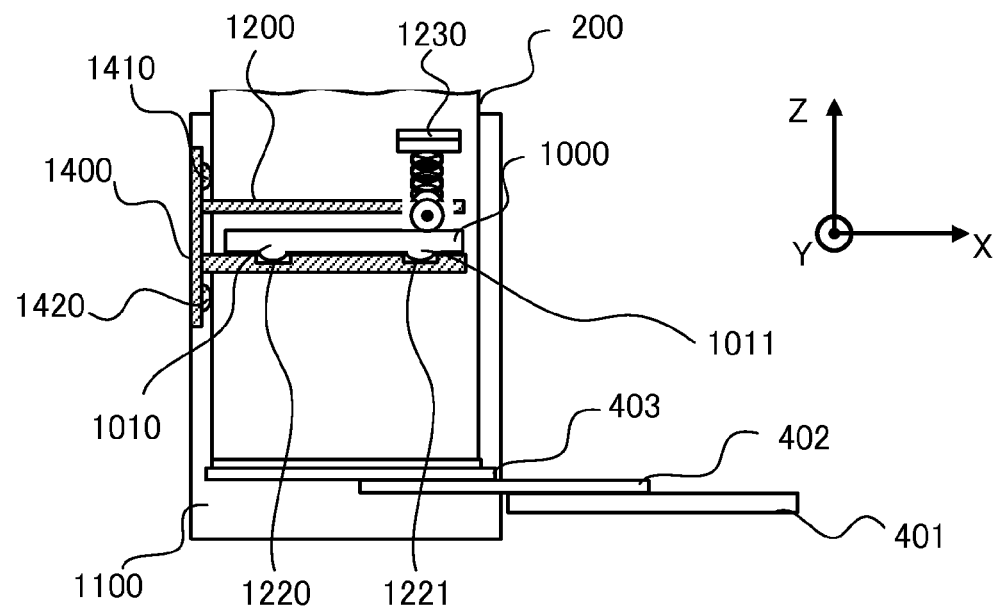
FIG. 20C is a schematic diagram explanatory an operation of a stacker guide 1000 and a storing unit guide 1200.

Operations to be executed when the stacker 200 is stored in the storage rack 41 or 42 will be described with reference to FIGS. 19 and 20A to 20C. FIG. 19 is a perspective view illustrating a state where the stacker 200 is stored in the storage rack 41. FIGS. 20A to 20C are schematic diagrams describing the operations of the stacker guide 1000 and the storing unit guide 1200. In FIGS. 19 and 20A to 20C, some components are not depicted, for convenience' sake.

As depicted in FIG. 19, the slide plates 402 and 403 are slid in the X-axis direction in a state where the stacker 200 is placed on the carrier table 62, thereby moving the stacker 200 to the location sandwiched by the two storing units 1100 adjacent to each other.

At this time, the stacker guide 1000 is moved in the horizontal direction being guided by the storing unit guide 1200, thereby storing the stacker 200 at the predetermined location sandwiched by the two storing units 1100 adjacent to each other in the storage rack 41 or 42.

The storing unit 1100 is provided with the leading guide 1300 to prevent collision of the stacker guide 1000 with the storing unit guide 1200. The stacker 200 is moved to the storage rack 41 being guided by the leading guide 1300 to an appropriate position at which the stacker guide 1000 is correctly fitted with the storing unit guide 1200.

When the stacker 200 is moved from a position depicted in FIG. 20A to that depicted in FIG. 20B, the stacker guide 1000 goes into the space formed by the support rail and the guide rail that constitute the storing unit guide 1200, and is moved forward sliding on the inner face of the storing unit guide 1200.

At this time, the stacker guide convex portion 1010 positioned in front in the direction of the forward movement of the stacker 200 passes over the groove 1221. However, as described above, the stacker guide convex portion 1010 and the groove 1221 are formed with their positions displaced from each other in the direction (Y-axis direction) vertical to the forward movement direction (X-axis direction) of the stacker 200, and thus they are never fitted with each other.

A roller 1230 is attached to the roller attachment portion 1210 of the storing unit guide 1200. When the stacker guide 1000 slides in the storing unit guide 1100, the stacker guide 1000 is pushed downward by the elastic force generated by a spring included in the roller 1230. Thereby, swings and vibrations caused when the stacker 200 is moved can be restrained.

The slide plates 402 and 403 of the carrier table 62 are bent downward to a greater degree as the slide plates 402 and 403 are brought away from the stand 401 due to the weight of the stacker 200 on the slide plate 403 and the weights of the slide plates 402 and 403 themselves. Therefore, a force causing swings and a forward inclination in the direction of the forward movement (–X-axis direction) is exerted on the stacker 200. However, the storing unit guide (support rail) 1200 supports the stacker guide 1000, and thus the stacker 200 is not affected by the bending of the slide plates 402 and 403. Therefore, inclination and swings of the stacker 200 are able to be restrained.

When the stacker 200 is moved from the position depicted in FIG. 20B to that depicted in FIG. 20C, the stacker guide convex portions 1010 and 1011 are respectively fitted with the grooves 1220 and 1221. Thereby, the stacker 200 is fixed at the predetermined position in the storage rack 41.

At the timing at which the stacker guide convex portions 1010 and 1011 are respectively fitted with the grooves 1220 and 1221, a force causing the stacker 200 to fall downward by the depth of the grooves 1220 and 1221 is exerted on the stacker 200. At this time, a force causing the stacker 200 to be inclined forward in the direction (the –X-axis direction in FIG. 20) of the forward movement thereof is exerted on the stacker 200, due to the bending occurring in the slide plates 402 and 403.

On the other hand, at this time, the front face of the stacker 200 directed toward the storage direction of the stacker 200 is in contact with the first and the second protruding portions 1410 and 1420 of the vertical sliding unit 1400. Therefore, the stacker 200 is not inclined in practice, and the stacker guide convex portions 1010 and 1011 are respectively fitted with the grooves 1220 and 1221.

Further, as described above, the stacker guide convex portions 1010 and 1011 are smoothly formed in a shape having a curve along the movement direction of the stacker 200, and are smoothly fitted with the grooves 1220 and 1221, respectively, thereby being able to prevent an impact caused when the stacker guide convex portions 1010 and 1011 are respectively fitted with the grooves 1220 and 1221.

<Another Exemplary Structure of Stacker Guide>

Figure 21:
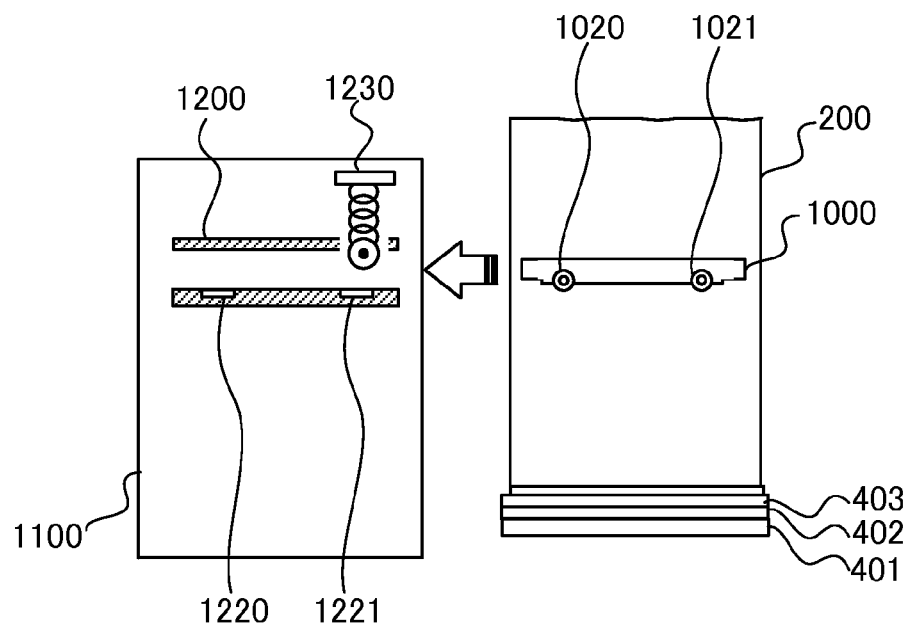
FIG. 21 is a schematic diagram for describing an operation of a stacker guide 1000 and a storing unit guide 1200.

As depicted in FIG. 21, the stacker guide convex portions 1010 and 1011 formed on the stacker guide 1000 may be structured as stacker guide rollers 1020 and 1021.

The stacker guide rollers 1020 and 1021 each are a rotating body configured to rotate on a rotation shaft. The rotation shaft is attached to the stacker guide 1000 in such a manner as to penetrate the stacker guide 1000.

As such, use of the stacker guide rollers 1020 and 1021 enables reduction in the frictional resistance that is generated when the stacker guide 1000 slides along the inside of the storing unit guide 1200, thereby being able to move the stacker 200 more smoothly.

<Another Exemplary Structure of Storing Unit Guide>

Another exemplary structure is also conceivable for the storing unit guide 1200. For example, as depicted in FIGS. 22A to 22C and 23A to 23C, a stopper 1240 may be disposed at the end on the side of the insertion and withdrawal of the stacker guide 1000 in the lower outer face of the storing unit guide 1200 (at the bottom of the support rail), as well as the rear end (the end on the –X side in FIGS. 22 and 23) of the storing unit guide 1200 may be blocked.

The stopper 1240 is, for example, an elastic board having a substantially rectangular shape or a substantially flat-plate-bar shape and made of a metal, a resin or a rubber, and is formed with a protruding portion in the board thickness direction on one end side in the longitudinal direction of the stopper 1240. The stopper 1240 is mounted on the storing unit guide 1200 on the lower outer face thereof with the protruding portion directed upward as well as positioned at the end of the storing unit guide 1200 on the side of the insertion and withdrawal of the stacker guide 1000. Further, the tip of the protruding portion slightly protrudes from the inner face of the storing unit guide 1200.

Figure 22A:
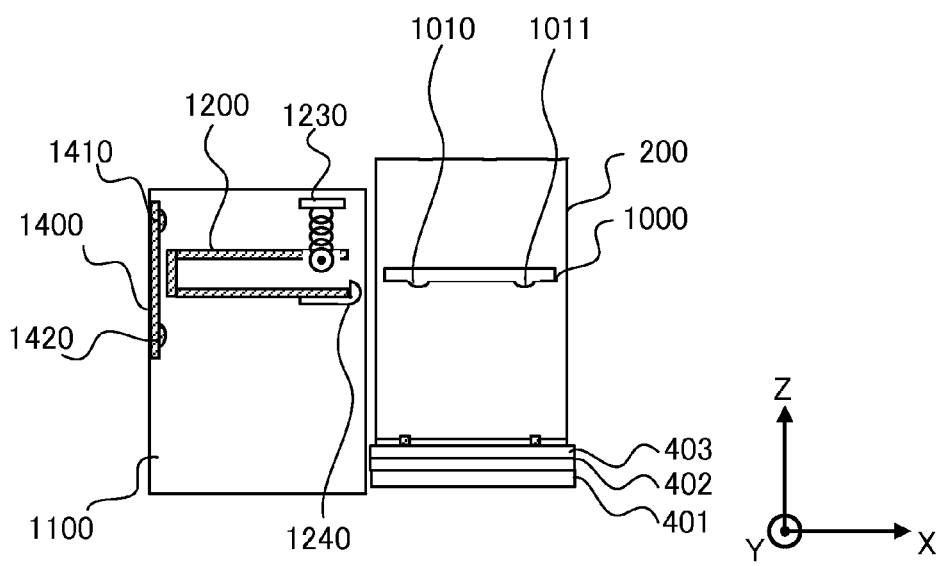
FIG. 22A is a schematic diagram for describing an operation of a stacker guide 1000 and a storing unit guide 1200.
Figure 22B:
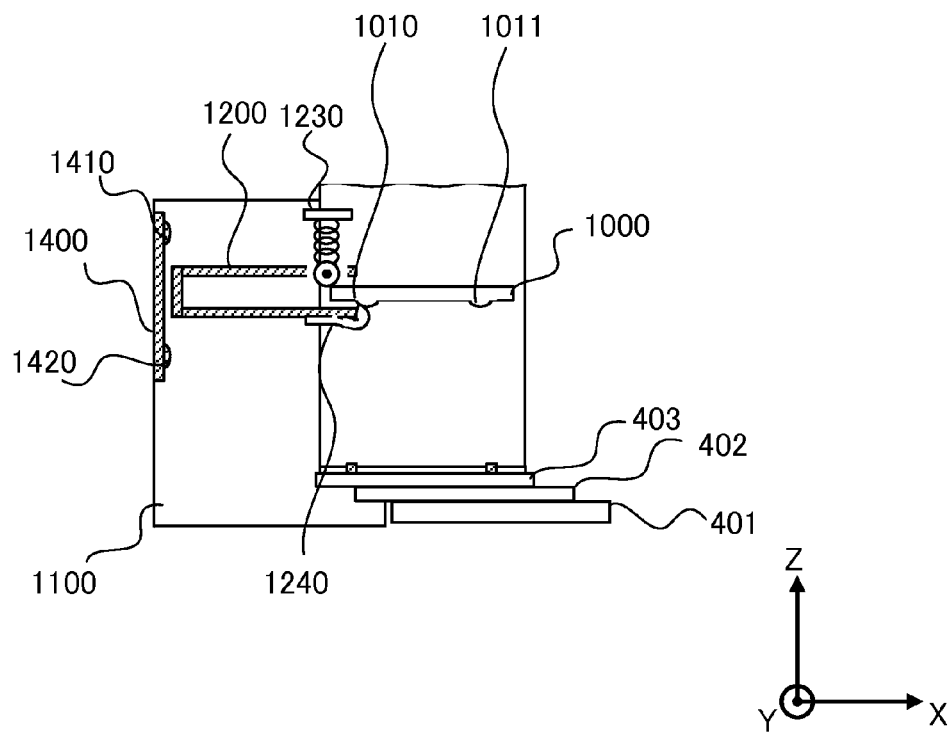
FIG. 22B is a schematic diagram for describing an operation of a stacker guide 1000 and a storing unit guide 1200.

At this time, when the stacker 200 is moved from the position depicted in FIG. 22A to that depicted in FIG. 22B, the stacker guide convex portion 1010 interferes with the protruding portion of the stopper 1240. However, due to the elasticity of the stopper 1240, the stacker guide convex portion 1010 pushes away the protruding portion of the stopper 1240, and thus the stacker guide 1000 is able to enter the inside of the storing unit guide 1200.

Figure 22C:
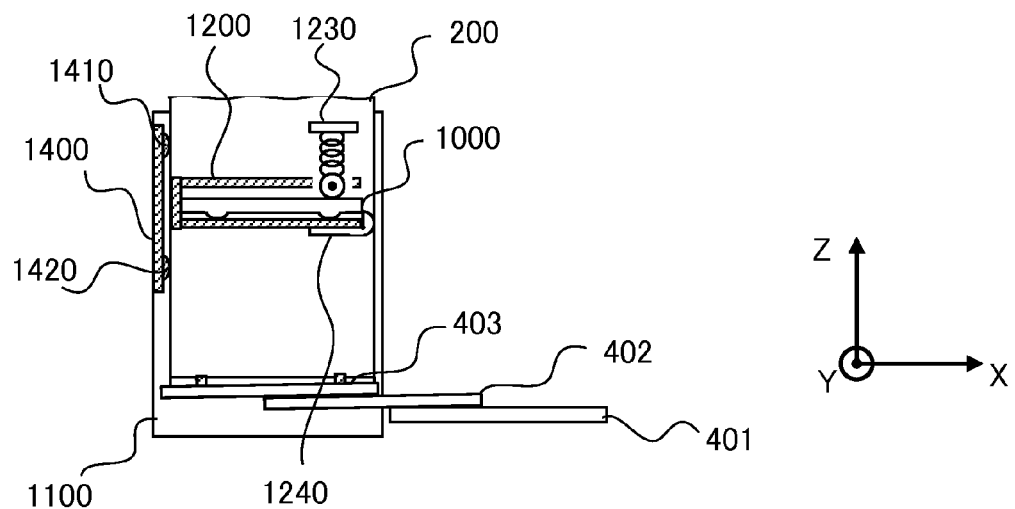
FIG. 22C is a schematic diagram of an operation of a stacker guide 1000 and a storing unit guide 1200.

The whole of the stacker guide 1000 enters the inside of the storing unit guide 1200 as it is, and when the tip of the stacker guide 1000 butts at the rear blocked part of the storing unit guide 1200, the state depicted in FIG. 22C is brought about.

Thereby, the stacker guide 1000 is unable to move forward nor backward from the storing unit guide 1200 due to the blocked part of the storing unit guide 1200 and the protruding portion of the stopper 1240, and is fixed in the storing unit guide 1200. Thereby, the stacker 200 is able to be fixed in the predetermined position in the storage rack 41 or 42.

As such, since the stacker 200 is fixed in the predetermined position using the stopper 1240, drilling process for the grooves 1220 and 1221 is unnecessary, thereby being able to simplify the manufacture of the storing unit guide 1200.

Figure 23A:
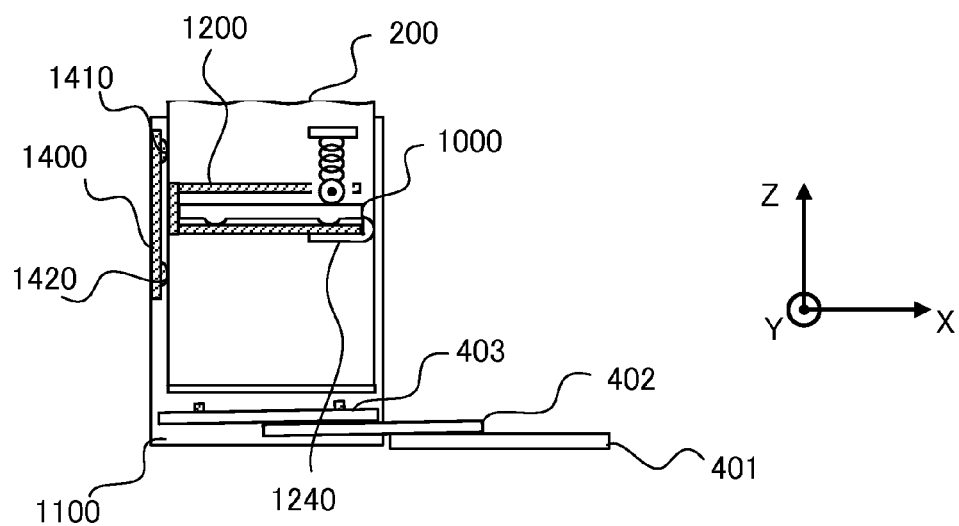
FIG. 23A is a schematic diagram of an operation of a stacker guide 1000 and a storing unit guide 1200.
Figure 23B:
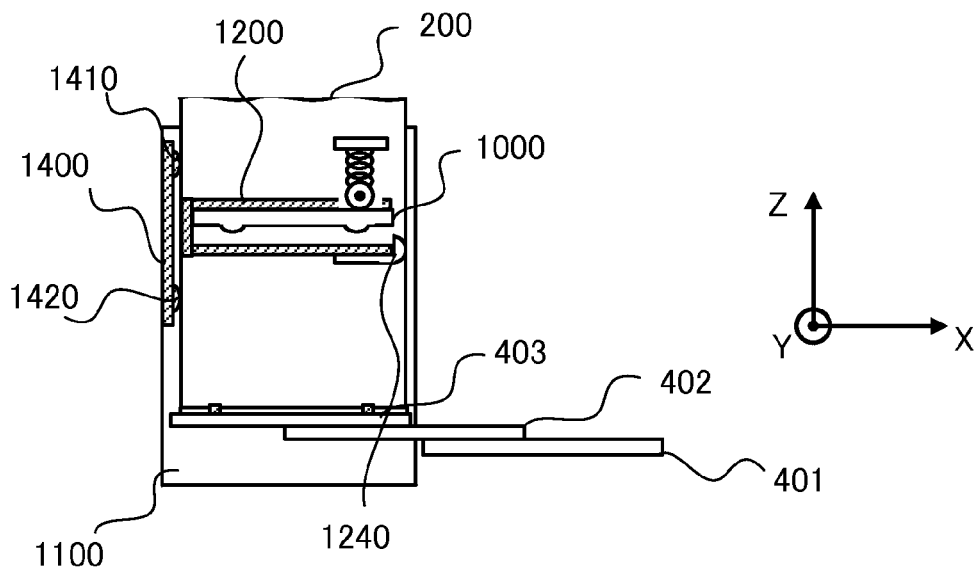
FIG. 23B is a schematic diagram of an operation of a stacker guide 1000 and a storing unit guide 1200.
Figure 23C:
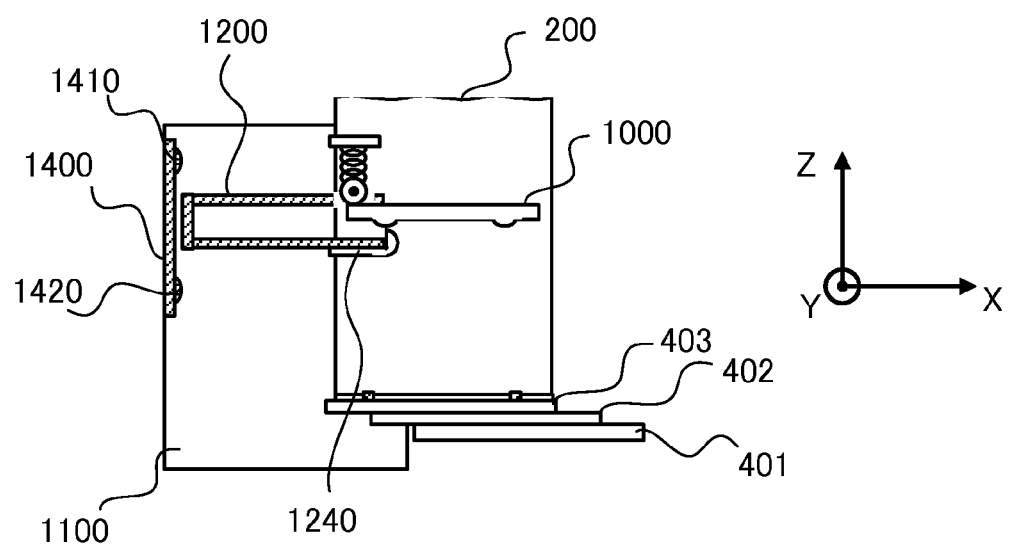
FIG. 23C is a schematic diagram of an operation of a stacker guide 1000 and a storing unit guide 1200.

As depicted in FIGS. 23A to 23C, when the stacker 200 is carried out from the storage rack 41 or 42, the carrier table 62 first lifts up the stacker 200 (FIG. 23B), so as to prevent interference between the stacker guide 1000 and the protruding portion of the stopper 1240. With the stacker 200 being lifted up, the slide plates 402 and 403 of the carrier table 62 are slid so as to be brought closer to the stand 401, thereby carrying the stacker 200 out.

When the stacker 200 is carried in, the carrier table 62 may also lift up the sacker 200, so that the stacker guide convex portions 1010 and 1011 will be moved over the protruding portion of the stopper 1240.

<Another Exemplary Storing Unit Guide>

As depicted in FIGS. 24A to 24D and 25A to 25D, the storing unit guide 1200 may be used together with a T-shaped stopper 1250 provided with a hook 1251 in the tip thereof.

Whereas, the stacker guide 1000 is provided with a stacker guide groove 1030 to be fitted with the hook 1251, and the tip of the stacker guide 1000 is processed into a tapered shape.

Figure 24A:
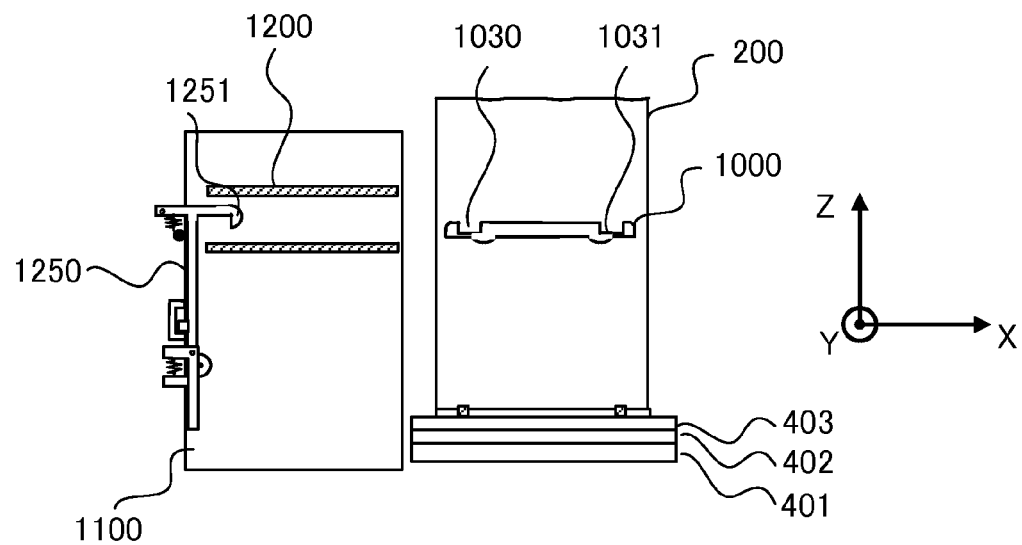
FIG. 24A is a schematic diagram of an operation of a stacker guide 1000 and a storing unit guide 1200.
Figure 24B:
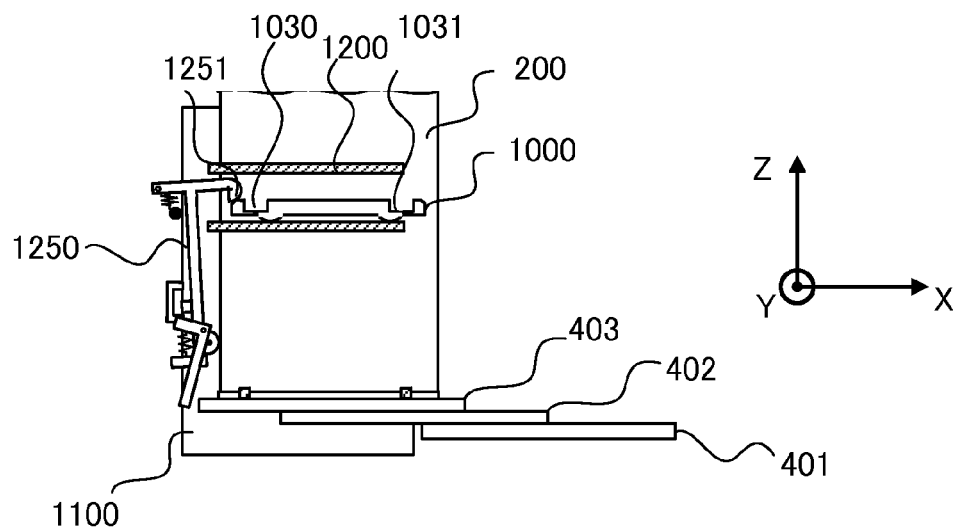
FIG. 24B is a schematic diagram of an operation of a stacker guide 1000 and a storing unit guide 1200.

In the case where the stacker 200 is carried into the storage rack 41 or 42, when the stacker 200 is moved from the position depicted in FIG. 24A to that depicted in FIG. 24B, the tip of the stacker guide 1000 interferes with the tip of the hook 1251. At this time, the tip of the stacker guide 1000 is processed into the tapered shape, thereby lifting up the hook 1251.

Figure 24C:
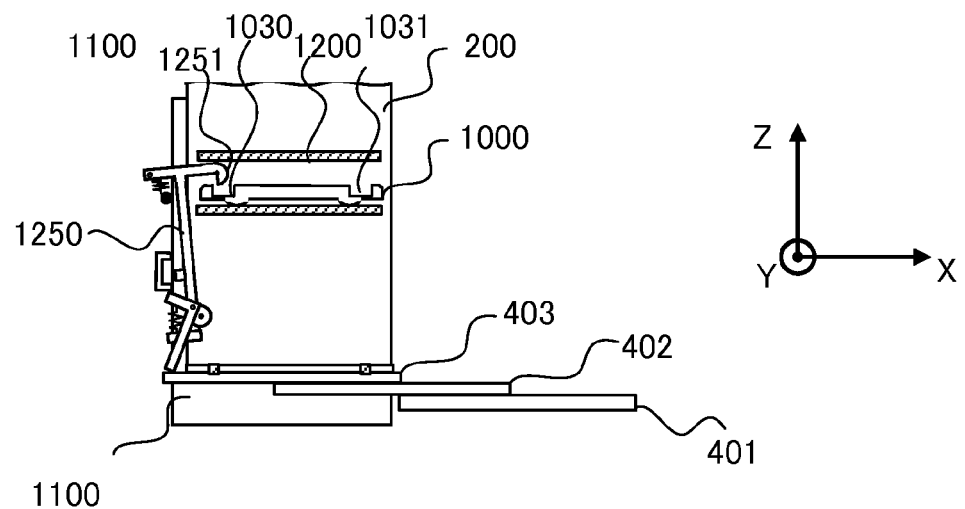
FIG. 24C is a schematic diagram of an operation of a stacker guide 1000 and a storing unit guide 1200.

Thereafter, as depicted in FIG. 24C, the tip of the slide plate 403 is brought into contact with the lower end of the T-shaped stopper 1250. Then, the slide plate 403 is moved pushing the lower end as it is, thereby causing the hook 1251 to be in a state of being lifted up.

Figure 24D:
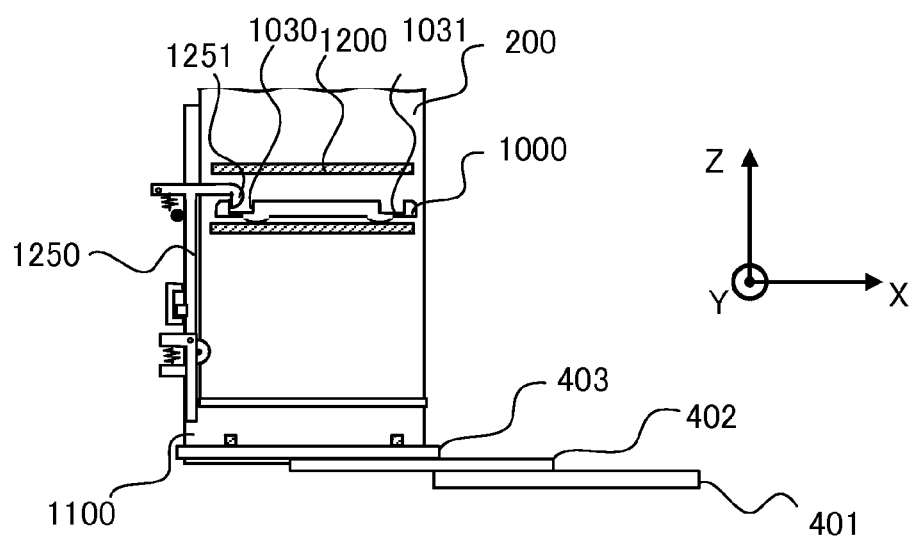
FIG. 24D is a schematic diagram of an operation of a stacker guide 1000 and a storing unit guide 1200.

When the hook 1250 reaches the position of the stacker guide groove 1030, the carrier table 62 is lowered downward (FIG. 24D). Thereby, the hook 1251 is engaged with the stacker guide groove 1030. Thereby, the stacker 200 is able to be fixed at the predetermined position in the storage rack 41 or 42.

Figure 25A:
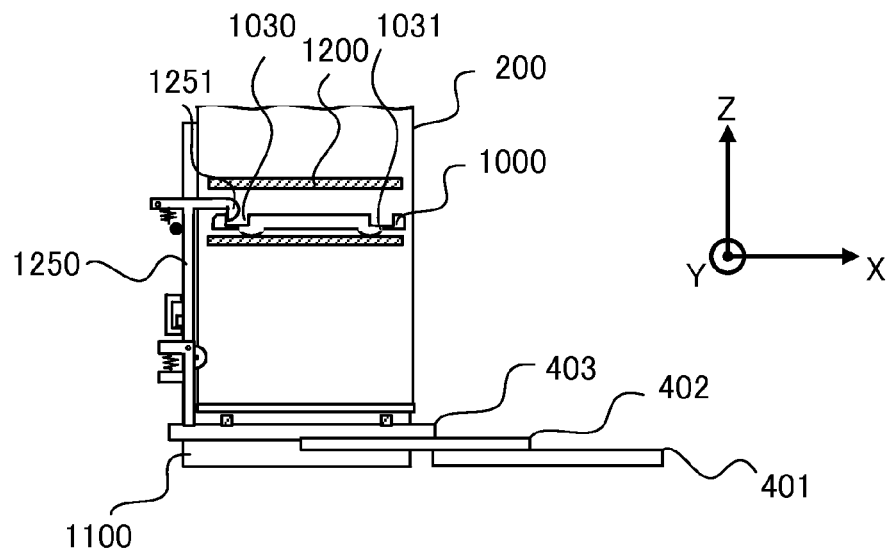
FIG. 25A is a schematic diagram of an operation of a stacker guide 1000 and a storing unit guide 1200.
Figure 25B:
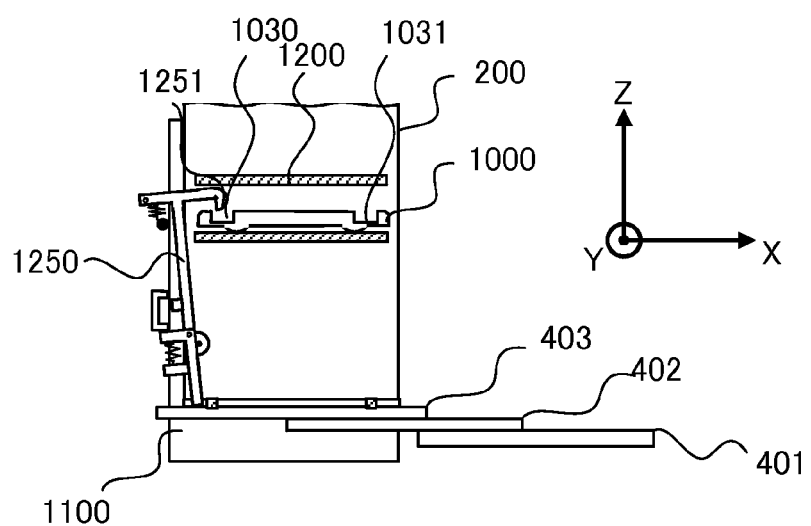
FIG. 25B is a schematic diagram of an operation of a stacker guide 1000 and a storing unit guide 1200.
Figure 25C:
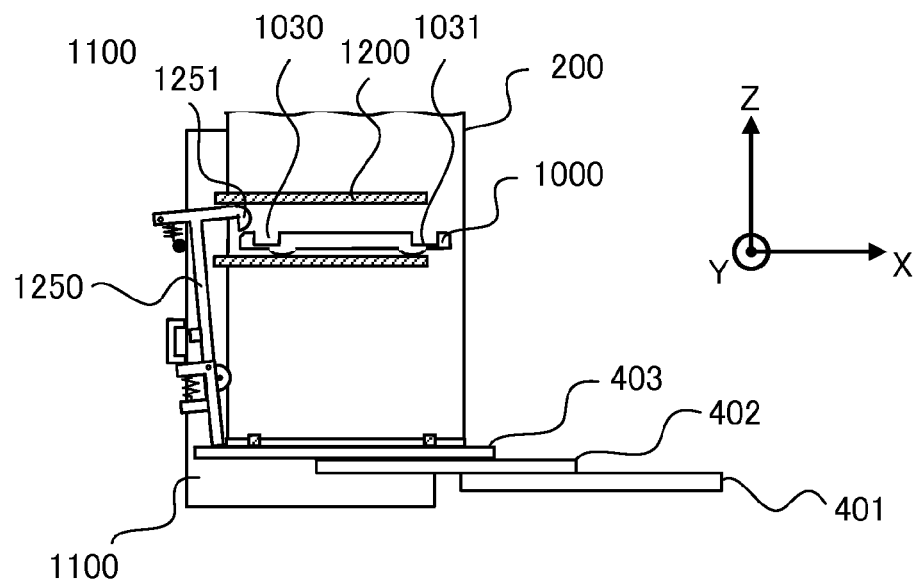
FIG. 25C is a schematic diagram of an operation of a stacker guide 1000 and a storing unit guide 1200.
Figure 25D:
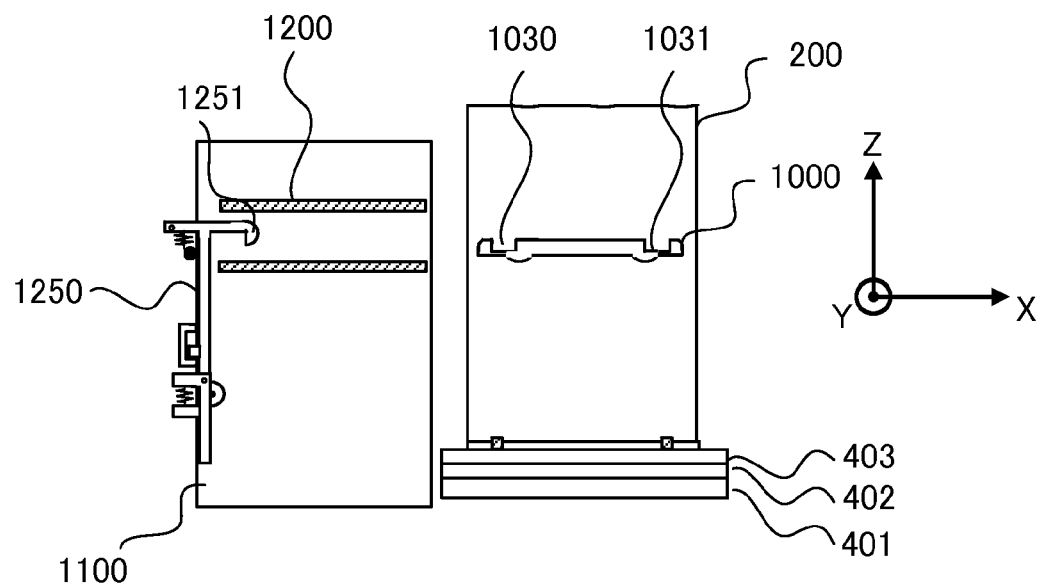
FIG. 25D is a schematic diagram of an operation of a stacker guide 1000 and a storing unit guide 1200.

Whereas, when the stacker 200 is carried out from the storage rack 41 or 42, as depicted in FIG. 25A, the carrier table 62 is lifted upward to push upward the lower end of the T-shaped stopper 1250. Then, with such a state being maintained, as depicted in FIG. 25B, the slide plate 403 of the carrier table 62 is slid toward the stand 401. As a result, as depicted in FIG. 25C, the engagement between the hook 1251 and the stacker guide groove 1030 is disengaged, and then, as depicted in FIG. 25D, the stacker 200 is able to be carried out from the storage rack 41 or 42.

Although not depicted, a roller may be provided at the lower end of the T-shaped stopper 1250, thereby being able to reduce the friction force generated when the tip of the slide plate 403 and the lower end of the T-shaped stopper 1250 are brought into contact with each other, which leads to enable a smooth operation.

<<Outline of Control Device 15 Controlling Operations of Incubator 10>>

Figure 26:
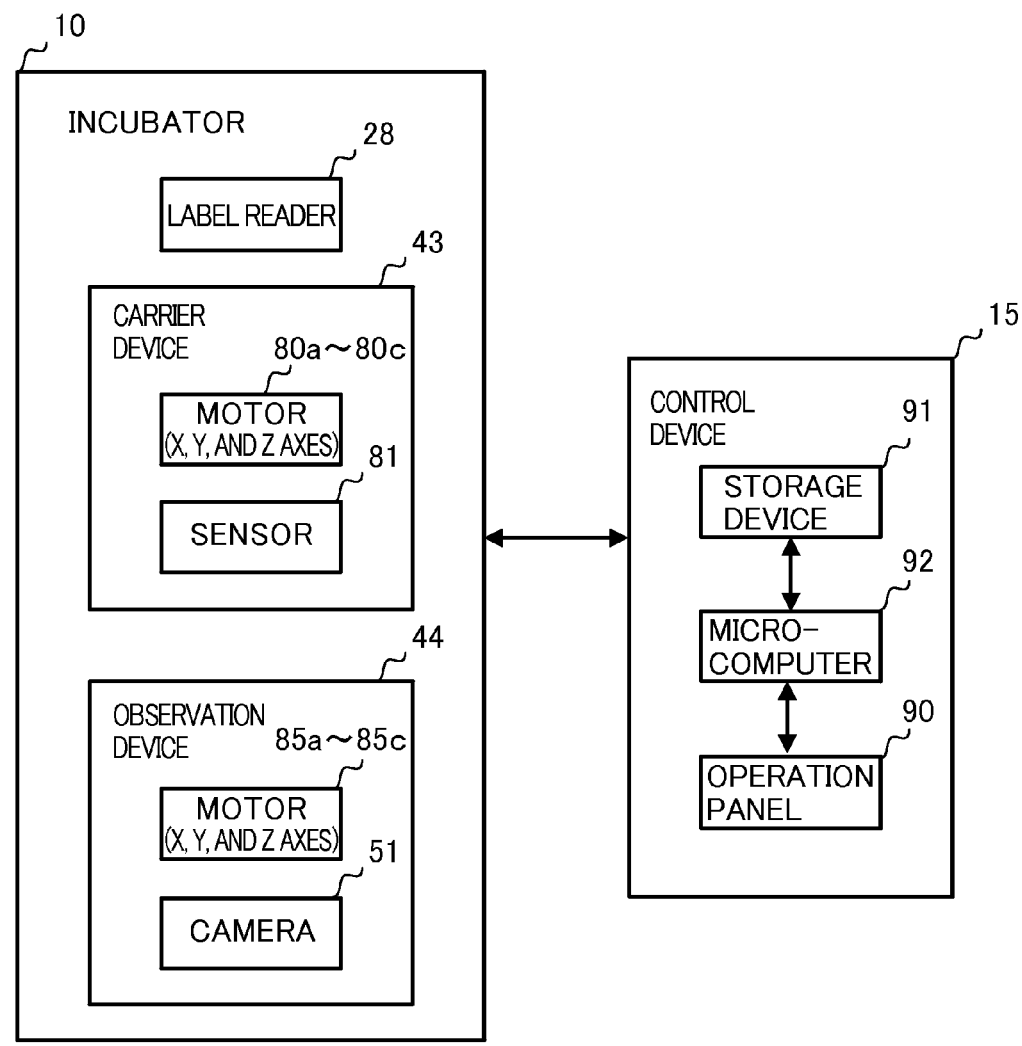
FIG. 26 is a diagram of an outline of a configuration of an incubator 10 and a control device 15.

A control device 15 configured to control the operation of the incubator 10 will be described with reference to FIG. 26. FIG. 26 is a diagram illustrating a configuration of the incubator 10 and the control device 15, and depicts blocks relating to a control system of the incubator 10. In FIG. 26, the blocks common between FIG. 26 and other drawings will be appropriately omitted in detail.

The incubator 10 includes the label reader 28, the carrier device 43, and the observation device 44.

The carrier device 43 includes: a motor 80a for the X-axis configured to move for example, e.g., the slide plate 403 in the X-axis direction; a motor 80b for the Y-axis configured to move the slide device 60 in the Y-axis direction; and a motor 80c for the Z-axis configured to move the slider 405 in the Z-axis direction. The carrier device 43 further includes a sensor 81 configured to output position information on the slide device 60 and the carrier table 62.

The observation device 44 includes motors 85a to 85c configured to move the observation stand 50 in the X-axis, the Y-axis, and the Z-axis directions, respectively, and the camera 51.

The control device 15 is a device configured to integrally control the incubator 10, and includes an operation panel 90, a storage device 91, and a microcomputer 92.

The operation panel 90 is a panel for a user to set an operation of the incubator 10. A result of the operation on the operation panel 90 is transmitted to the microcomputer 92. Based on the operation result, the control device 15 controls the blocks of the incubator 10. Further, the operation panel 90 displays thereon the operation result, the state of the incubator 10 (e.g., temperature and humidity), and various kinds of information.

The storage device 91 is configured to store program data to be executed by the microcomputer 92 and various kinds of data. The microcomputer 92 executes the program data stored in the storage device 91, thereby realizing various functions.

==Functional Blocks of Microcomputer 92==

Figure 27:
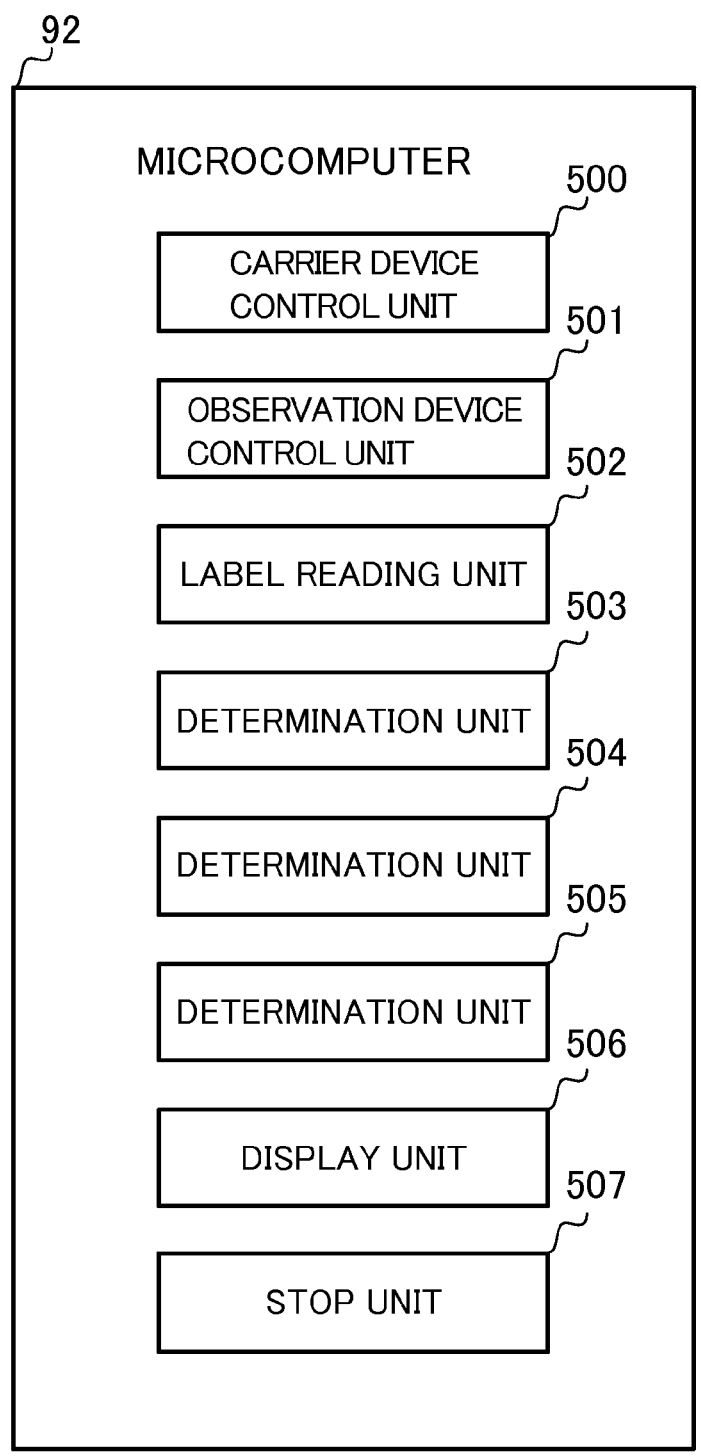
FIG. 27 is a diagram of functional blocks realized by a microcomputer 92.

FIG. 27 is a diagram of functional blocks to be realized by the microcomputer 92 by the execution of the program data by the microcomputer 92. In the microcomputer 92, a carrier device control unit 500, an observation device control unit 501, a label reading unit 502, determination units 503 to 505, a display unit 506, and a stop unit 507 are realized.

The carrier device control unit 500 is configured to control the motors 80a to 80c based on the operation result on the operation panel 90 (hereinafter, referred to as "operation result") and the output of the sensor 81.

The observation device control unit 501 is configured to control the camera 51 and the motors 85a to 85c based on the operation result.

The label reading unit 502 is configured to cause the label reader 28 to read a label such as an IC tag or a bar code attached to a target object (the container 100 or the stacker 200).

The determination unit 503 is configured to determine presence or absence of a currently running task (e.g., observation) when a carrying-in instruction or a carrying-out instruction is inputted thereto as an operation result.

The determination unit 504 is configured to, when the determination unit 503 determines that a currently running task is present, determine whether the currently running task is finished within the predetermined time period.

The determination unit 505 is configured to determine whether the observation device 44 has observed all the containers 100 stored in the designated stacker 200.

The display unit 506 is configured to display the operation result, for example, e.g., the currently running task, on the operation panel 90.

The stop unit 507 is configured to, when the determination unit 504 determines that the currently running task is not finished within the predetermined time period, stop the process that is based on a currently inputted instruction (carrying-in instruction or the carrying-out instruction).

==Example of Carrying-In Process==

Figure 28:
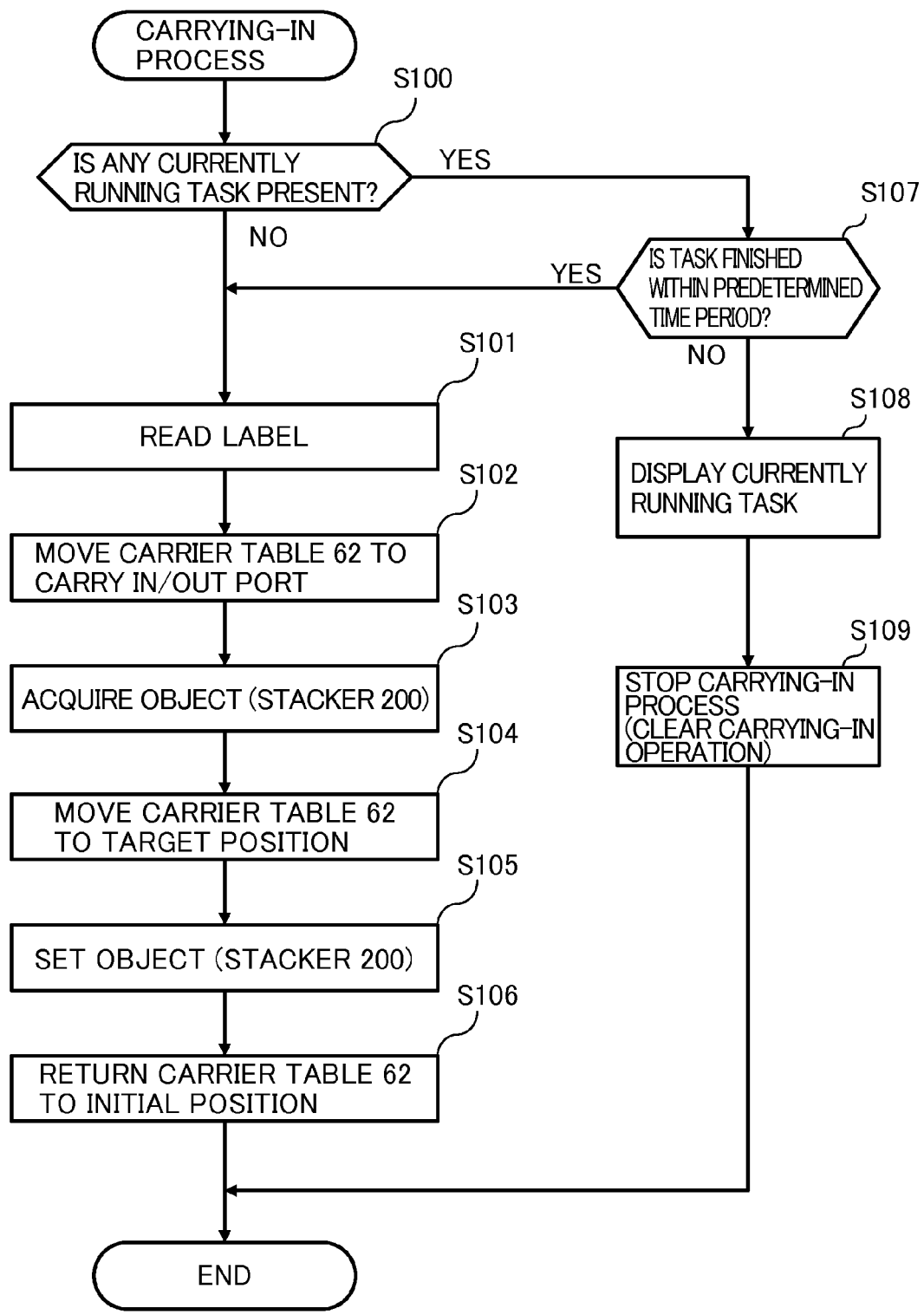

FIG. 28 is a flowchart of an example of a process to be executed when a target object (e.g., the stacker 200) is carried in. It is assumed that the control device 15 opens and closes the carrying in/out door 27 as appropriate. The carrying-in process is executed after the user sets the stacker 200 on an installation stand not depicted outside the culture chamber 22. When an object is set on the installation stand, the installation stand is disposed at a position at which the label reader 28 can read the label of the target object. The user designates a storage destination of the stacker 200 based on the compartments described above.

When the carrying-in instruction is inputted from the operation panel 90, the determination unit 502 determines whether any currently running task is present (S100). When the determination unit 502 determines that no currently running task is present (S100: NO), the label reading unit 502 causes the label reader 28 to read the label of the stacker 200 (S101). The label reading unit 502 stores information on the read label in the storage device 91. The carrier device control unit 500 moves the carrier table 62 to the carrying in/out port 26 (S102), and causes the carrier table 62 to acquire the stacker 200 (S103). Specifically, the carrier device control unit 500 moves the slide plate 403 and causes the stacker 200 to be placed on the slide plate 403. Then, the carrier device control unit 500 moves the carrier table 62 to a target position (S104) and causes the stacker 200 to be set in a designated compartment (S105). Further, the carrier device control unit 500 returns the carrier table 62 to the designated initial position (S106).

When having determined that a currently running task is present at step S100 (S100: YES), the determination unit 504 determines whether the currently running task is finished within the predetermined time period (S107). When the determination unit 504 determines that the currently running task is finished within the predetermined time period (S107: YES), the process at step S101 is executed. However, when the determination unit 504 determines that the currently running task is not finished within the predetermined time period (S107: NO), the display unit 506 displays the currently running task on the operation panel 90 (S108). Then, the stop unit 507 stops the carrying-in process based on the carrying-in instruction (S109).

By such processes being executed, the stacker 200 is carried in and then stored in a designated compartment of the culture chamber 22. In an embodiment of the present invention, the label reading unit 502 stores the label information in the storage device 91 associating the label information with the compartment designated by the user as the storage destination.

Therefore, for example, in the carrying-out process, the label information is designated, thereby being able to carry the desired stacker 200 out without designating the compartment.

==Example of Carrying-Out Process==

Figure 29:
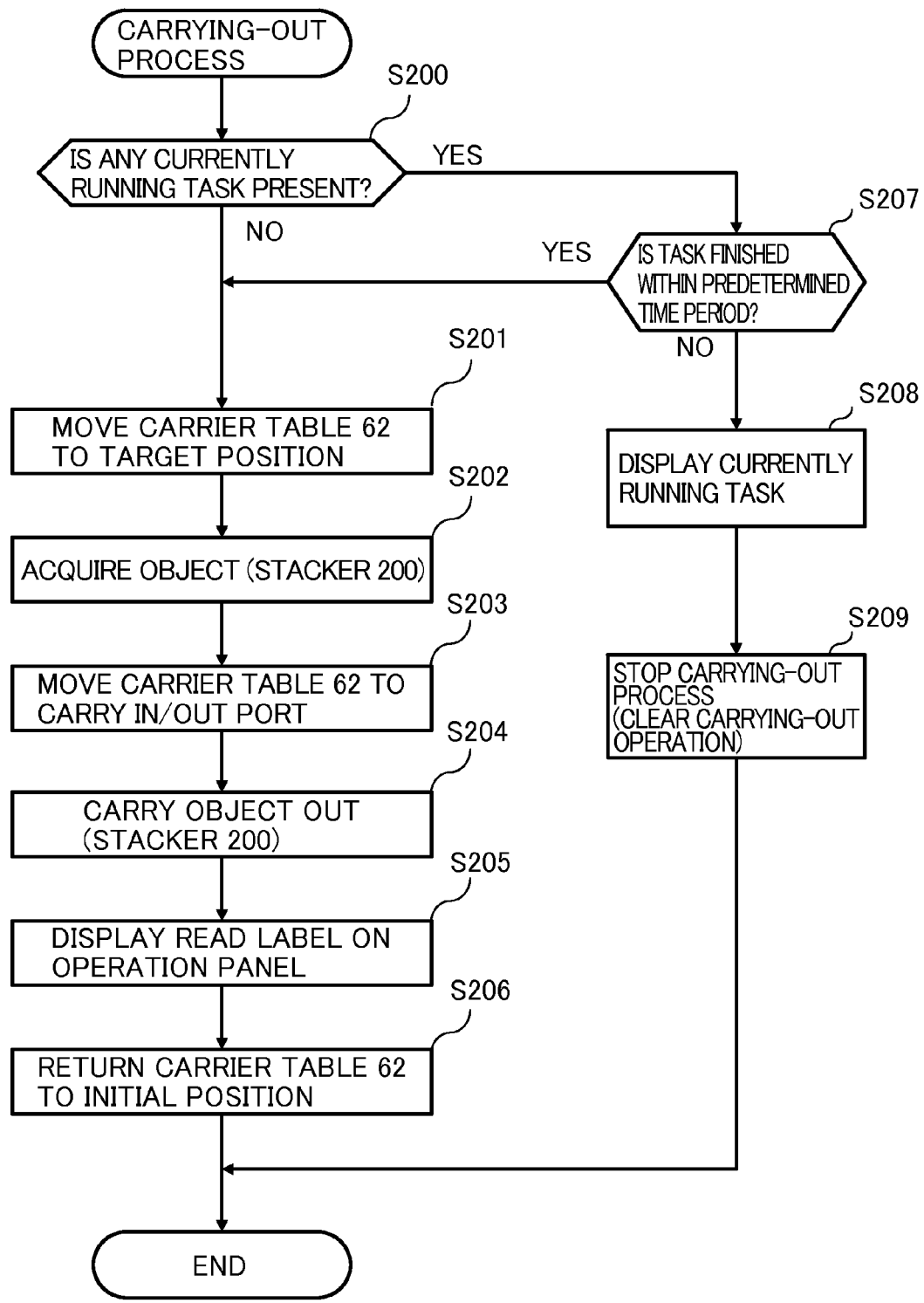
FIG. 29 is a flowchart illustrating an example of a process executed when a target object is carried out.

FIG. 29 is a flowchart of an example of a process to be executed when a target object (e.g., the stacker 200) is carried out. It is assumed that the control device 15 opens and closes the carrying in/out door 27 as appropriate. For example, the user designates the stacker 200 to be carried out based on the label information. That is to say, the user inputs the label information of the stacker 200 to be carried out, using the operation panel 90.

When the carrying-out instruction is inputted from the operation panel 90, the determination unit 502 determines whether any currently running task is present (S200). When the determination unit 502 determines that no currently running task is present (S200: NO), the carrier device control unit 500 moves the carrier table 62 to the target position based on the label information (S201). And, the carrier device control unit 500 moves the carrier table 62 to acquire the stacker 200 of the designated label (S202). Then, the carrier device control unit 500 moves the carrier table 62 to the carrying in/out port 26 (S203), and carries the stacker 200 out of the culture chamber 22 (S204). The label reading unit 502 causes the label reader 28 to read the label of the stacker 200 and simultaneously displays the information on the label on the operation panel 90 (S205). As a result, the user is able to determine whether the stacker 200 of the designated label is carried out. At step S205, the label reading unit 502 stores the information on the read label in the storage device 91. The carrier device control unit 500 returns the carrier table 62 to the designated initial position (S206).

When the determination unit 502 determines that a currently running task is present at step S200 (S200: YES), the determination unit 504 determines whether the currently running task is finished within the predetermined time period (S207). When the determination unit 504 determines that the currently running task is finished within the predetermined time period (S207: YES), the process at step S201 is executed. However, when the determination unit 504 determines that the currently running task is not finished within the predetermined time period (S207: NO), the display unit 506 displays the currently running task on the operation panel 90 (S208). Then, the stop unit 507 stops the carrying-out process executed based on the carrying-out instruction (S209).

By such processes being executed, the designated stacker 200 in the culture chamber 22 is carried out therefrom.

==Example of Observation Process==

Figure 30:
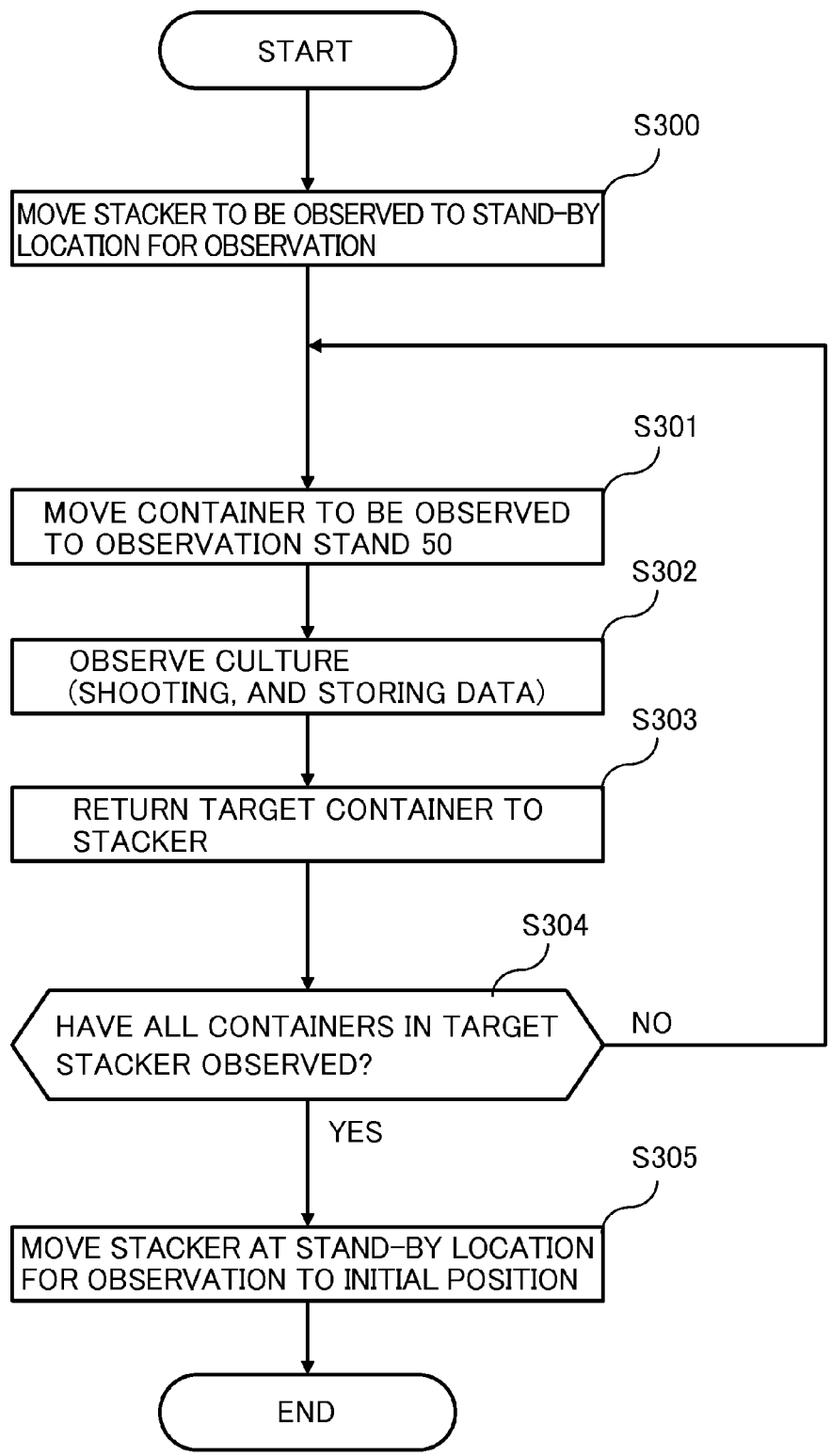
FIG. 30 is a flowchart illustrating an example of a process executed when a culture is observed.

FIG. 30 is a flowchart of an example of a process to be executed when a culture is observed. The user operates the operation panel 90 to designate the stacker 200 to be observed.

When an instruction to start the observation is inputted from the operation panel 90, the carrier device control unit 500 moves the designated stacker 200 to be observed to the compartment 7 where the stacker 200 stands by for observation (S300). Then, the carrier device control unit 500 moves the container 100 to be observed, from the stacker 200 to be observed to the observation stand 50 of the observation device 44 (S301). The observation device control unit 501 shoots an image and a video image of a culture in the container 100 to be observed that is placed on the observation stand 50, and stores the shot data (image data and video image data) in the storage device 91 (S302). Thereafter, the carrier device control unit 500 returns the target container 100 having been observed to the stacker 200 (S303). The determination unit 505 determines whether all the containers 100 of the designated target stacker 200 have already observed (S304). When the observation of all the containers 100 of the target stacker 200 is finished (S304: YES), the carrier device control unit 500 moves the stacker 200 from the compartment 7 where the stacker 200 stands by for observation to the initial position (initial compartment) (S305). Whereas, when the observation of all the containers 100 of the target stacker 200 is not yet finished (S304: NO), the process at step S301 is executed again.

By executing the above processes, all the cultures in the containers 100 stored in the designated stacker 200 are able to be observed. As such, the container 100 to be observed is carried together with the stacker 200 to the position for standing by, and each container (tray) 100 is carried between the position for standing by and the observation stand 50 and stored therein. Therefore, the conveyance only has to be executed for the shortest distance, thereby being able to reduce the necessary time period and also the influence on the target object to be observed (culture) in the container 100.

In the observation process depicted in FIG. 30, the observation process is immediately executed when the instruction to start the observation is inputted. However, it is not limited thereto. For example, e.g., the process at step S100 depicted in FIG. 28 may be executed. Further, the microcomputer 92 may be caused to determine whether any carrying-out process is currently being executed, and if a carrying-out process is currently being executed, the carrying-out process may be temporarily suspended and thereafter the observation process of FIG. 30 may be executed, or the carrying-out process may have been executed and thereafter the observation process may be executed.

Hereinabove, the incubator 10 according to an embodiment of the present invention has been described. According to the incubator 10 according to an embodiment of the present invention, the stacker 200 is stored in the storage rack 41 or 42, with the pair of stacker guides 1000 provided on both the sides of the stacker 200 being supported by the pair of storing unit guide 1200 provided on the storing unit 1100.

Therefore, the weight load is able to be reduced that is applied by the stacker 200 to the carrier table 62, thereby being able to prevent vibrations and swings of the stacker 200 even if the carrier table 62 to carry the stacker 200 is relatively simply structured.

Thus, the carrier table 62 can be reduced in size and thickness, thereby being able to reduce the working space that is necessary when the carrier table 62 carries the tray 110 into or out from the stacker 200. Therefore, the intervals between the trays 110 stored in the stacker 200 in a multi-story form can be reduced, thereby being able to improve the storage efficiency of the containers 100 in the stacker 200. Thus, more containers 100 can be stored in the incubator 10.

As such, according to the incubator 10 of an embodiment of the present invention, swings and vibrations generated when the stacker 200 stored in the storage rack 41 or 42 can be restrained without degrading the storage efficiency of the containers 100 in the stacker 200 capable of storing therein a plurality of containers 100 containing liquid.

Second Embodiment

Outline of Incubator 10

A description will be given of a second embodiment in the case where a storage apparatus according to an embodiment of the present invention is applied to an incubator 10. In the description of a second embodiment of the present invention, the components and the functions specific to the incubator 10 in a second embodiment of the present invention will mainly be described, and descriptions of the same components and functions as those in a first embodiment of the present invention and overlapping descriptions will be omitted as appropriate.

As depicted in FIG. 1, the incubator 10 (storage apparatus) according to an embodiment of the present invention is a device for use in cultivating a culture such as a cell (specimen) and a microorganism, and includes the outer case 20 and the inner case 21.

Figure 31:
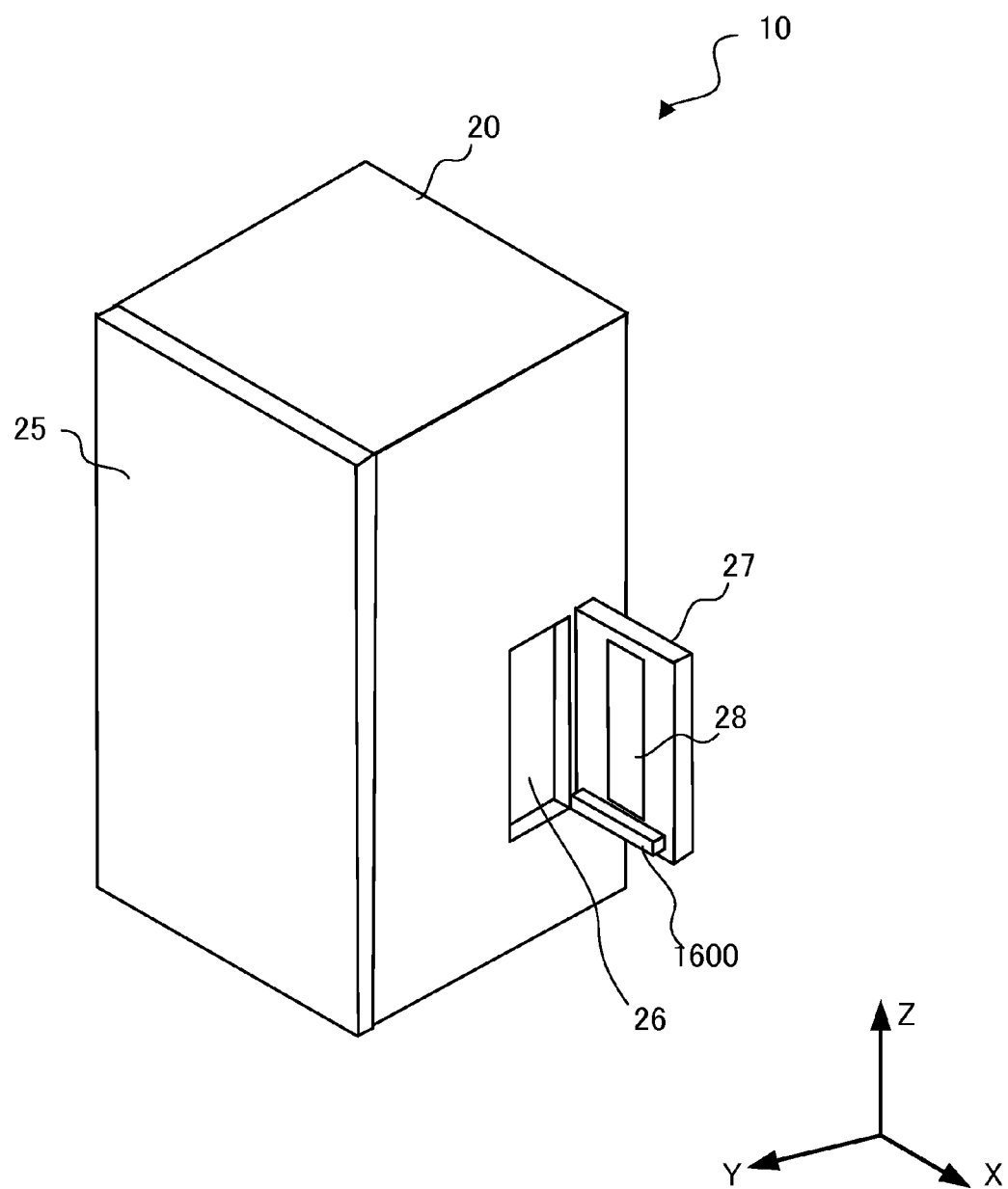
FIG. 31 is an external perspective view of an incubator 10.

As depicted in FIG. 31, the right side face of the outer case 20 of the incubator 10 according to an embodiment of the present invention is provided with the carrying in/out port 26 penetrating from the outside of the culture chamber 22 into the inside thereof. The carrying in/out port 26 is an opening portion formed to carry the stacker 200 storing the container 100 storing a culture therethrough into the culture chamber 22, and to carry such items out from the culture chamber 22. A carrying in/out door 27 configured to open outward is attached to the outer case 20 on the right side face thereof to enable the carrying in/out port 26 to be opened or closed. The carrying-in/out door 27 is provided with the label reader 28 configured to read a label such as an electronic tag or a bar code attached to for example, e.g., the culture container 100 when for example, e.g., the culture container 100 are carried into or out from the culture chamber 22. The carrying in/out door 27 is configured to pivot about a hinge (support shaft) provided in the vertical direction, and open outward at an angle within a range of 90±2 degrees, preferably, 90±0.5 degrees with respect to the face of the opening portion of the carrying in/out port 26.

Although the details will be described later, the carrying in/out door 27 is provided with a carrying in/out door guide (first rail member A') 1600 configured to support a carrying-in/out device 1500 that is used when the stacker 200 is carried out from or to the carrying in/out port 26. The carrying in/out door guide 1600 is disposed on the inner face of the carrying in/out door 27; is a rail extending in the horizontal direction with respect to a direction (X-axis direction) in which the carrying-in/out device 1500 provided on the inner side of the carrying in/out port 26 is pulled out to the exterior of the carrying in/out port 26 when the carrying in/out door 27 is opened at a right angle with respect to the carrying in/out port 26; and supports the carrying-in/out device 1500 pulled out from the carrying in/out port 26 to the exterior.

The carrying-in/out device 1500 is installed in the compartment 15 (see FIG. 11) closest to the carrying in/out port 26, and is installed so as to be capable of sliding between a first position inside the incubator 10 and a second position outside thereof that are opposed to each other sandwiching the carrying in/out port 26.

Therefore, the stacker 200 stored in the storage rack 41 or 42 in the incubator 10 is placed on the carrying-in/out device 1500 provided in the compartment 15 (first position) using the carrier device 43; and the carrying in/out door 27 is opened from the exterior of the incubator 10; the carrying-in/out device 1500 is pulled out to the exterior, thereby being able to carry the stacker 200 stored in the incubator 10 out to the second position in the exterior.

The stacker 200 is placed on the carrying-in/out device 1500 that is pulled out to the second position in the exterior of the incubator 10; the carrying-in/out device 1500 is pushed to the first position inside the incubator 10; the carrying in/out door 27 is closed; and thereafter the stacker 200 placed on the carrying-in/out device 1500 is moved into the storage rack 41 or 42 using the carrier device 43, thereby being able to carry the stacker 200 into the storage rack 41 or 42 from the exterior of the incubator 10.

==Carrying-In/Out Device 1500 and Carrying-In/Out Door 27==

Descriptions will be give of the constructions of the carrying-in/out device (carrying-in/out mechanism) 1500 and the carrying in/out door 27 that are used when the stacker 200 is carried into or out from the incubator 10, and operations that are executed when the stacker 200 is carried in/out, with reference to FIGS. 32A-32C to 39.

Figure 37:
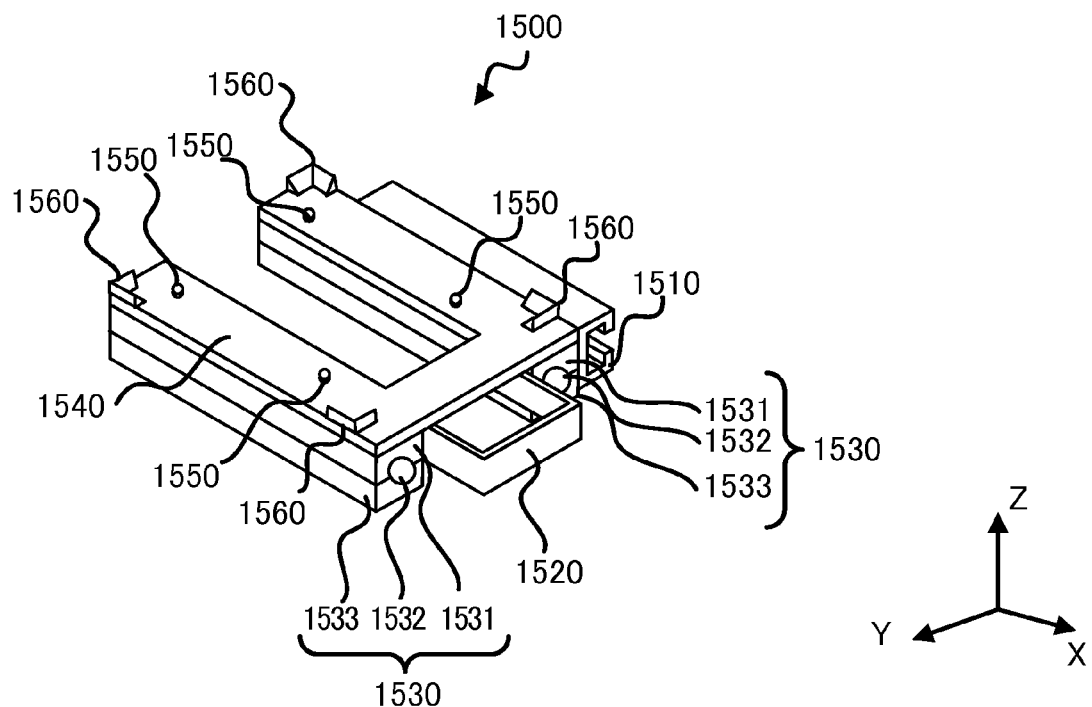
FIG. 37 is a schematic diagram illustrating a structure of a carrying-in/out device 1500.
Figure 38:
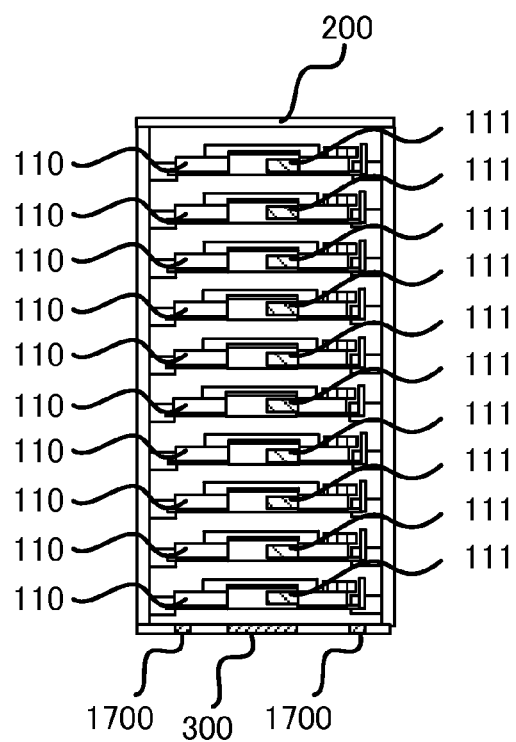
FIG. 38 is a schematic diagram illustrating a structure of a stacker 200.
Figure 39:
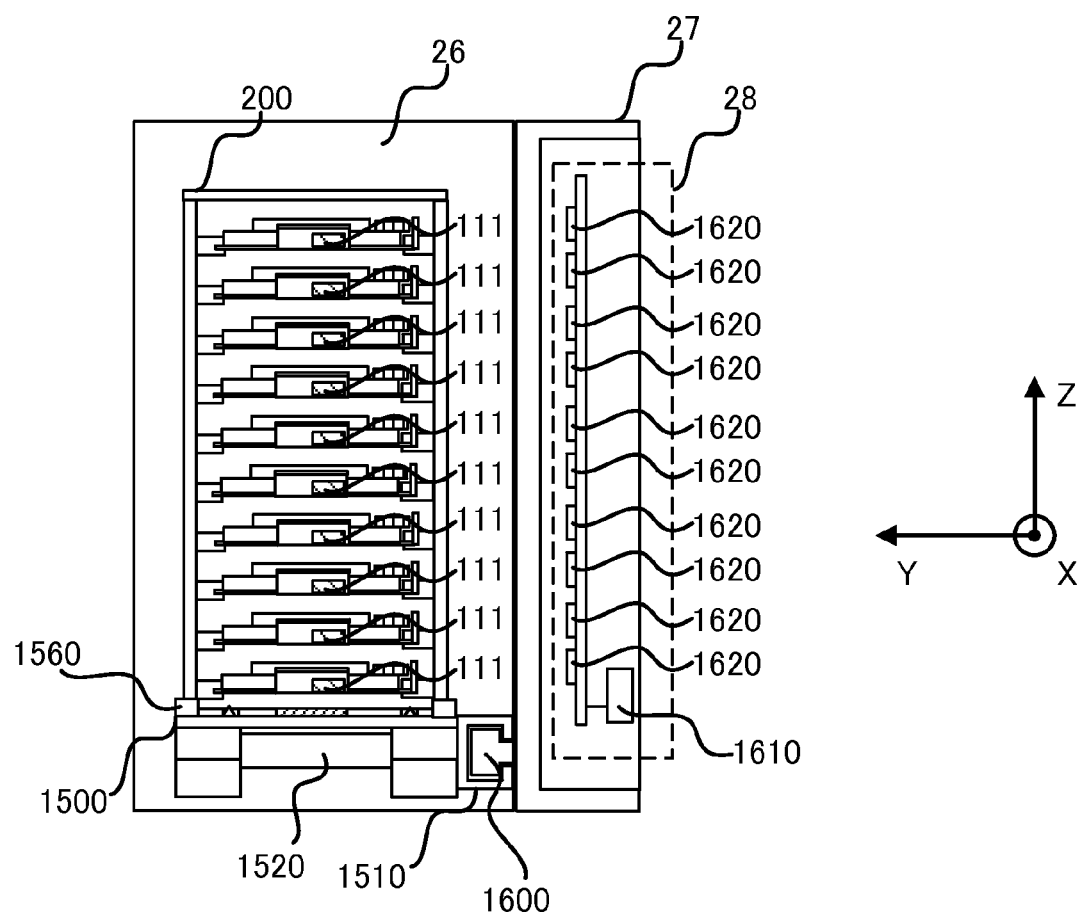
FIG. 39 is a schematic diagram illustrating a positional relationship between an electronic tag 111 of a container 100 stored in a stacker 200 and an antenna 1620 in a carrying in/out door 27.

FIGS. 32A-32C to 36 are diagrams illustrating the state where the stacker 200 is carried out from the carrying in/out port 26 and the structure of the carrying in/out door 27. FIG. 37 is a diagram illustrating the structure of the carrying-in/out device 1500. FIG. 38 is a diagram illustrating the structure of the stacker 200. FIG. 39 is a diagram illustrating the state where identification information recorded on a tag such as an electronic tag or a bar code attached to each container 100 in the stacker 200 is read using the label reader 28 provided on the carrying in/out door 27.

As described above, the carrying-in/out device 1500 is installed in the compartment 15 (first position) of the storage rack 42 closest to the carrying in/out port 26. The carrying-in/out device 1500 is installed so as to be capable of sliding between the first position inside the incubator 10 and the second position outside thereof that are opposed to each other sandwiching the carrying in/out port 26.

Figure 32A:
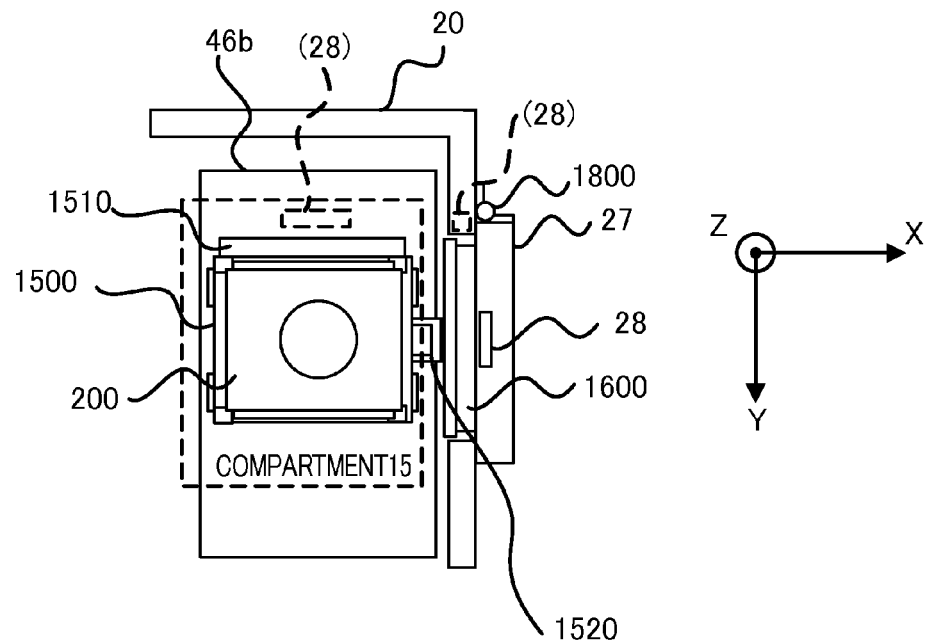
FIG. 32A is a schematic diagram for describing an operation of carrying a stacker 200 in/out through a carrying in/out port 26.

As depicted in FIG. 32A, in the case where the stacker 200 is carried out to the exterior of the incubator 10, the stacker 200 is placed, using the carrier device 43, on the carrying-in/out device 1500 installed in the compartment 15 (first position) closest to the carrying in/out door 27, with the carrying in/out door 27 being closed.

Figure 32B:
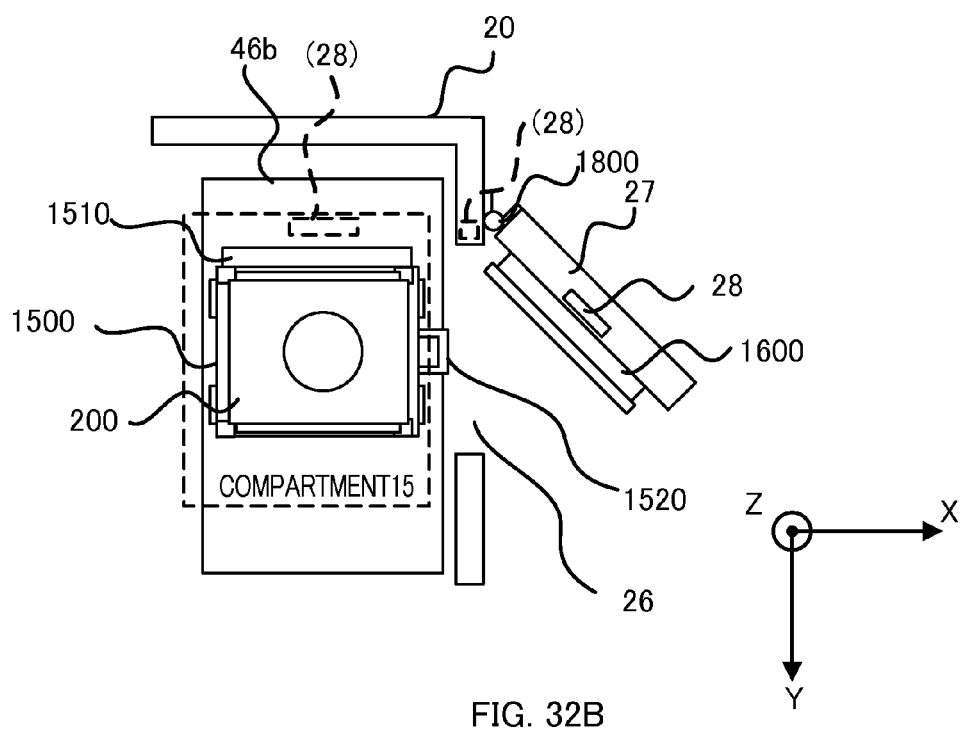
FIG. 32B is a schematic diagram for describing an operation of carrying a stacker 200 in/out through a carrying in/out port 26.
Figure 32C:
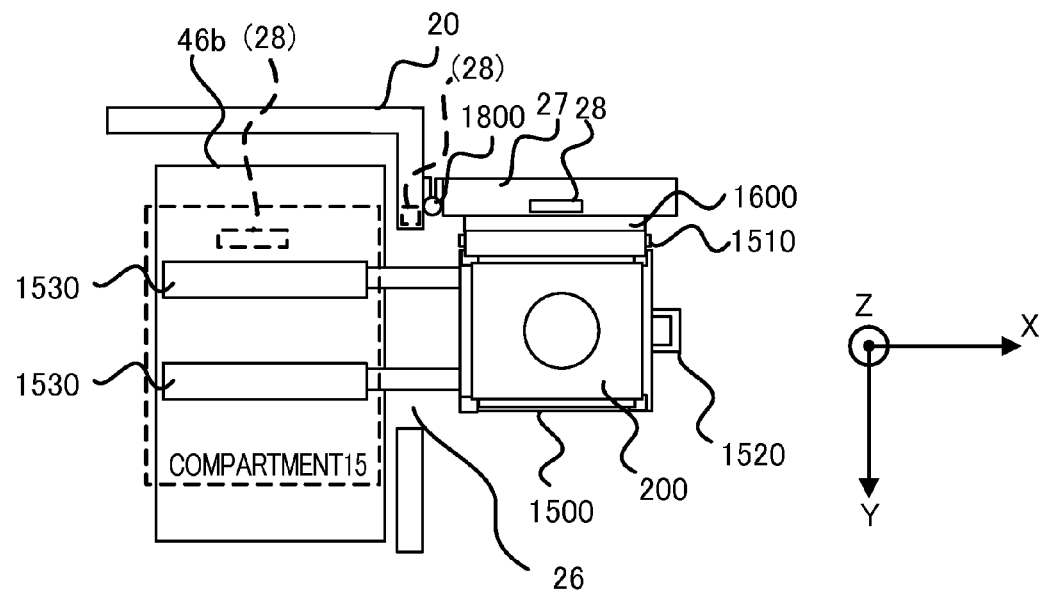
FIG. 32C is a schematic diagram for describing an operation of carrying a stacker 200 in/out through a carrying in/out port 26.

As depicted in FIG. 32B, the carrying in/out door 27 is opened. The carrying in/out door 27 is configured to pivot about the hinge (support shaft) 1800, and as depicted in FIG. 32C, is configured to open at a right angle with respect to the face of the opening portion of the carrying in/out port 26.

In this state, when the user holds a handle 1520 provided on the carrying-in/out device 1500 and pulls out the carrying-in/out device 1500 to the exterior (in the X-axis direction), the carrying-in/out device 1500 having the stacker 200 placed thereon is slid along slide rails 1530, and is carried out to the second position in the exterior of the incubator 10. As such, the stacker 200 is able to be carried out to the exterior of the incubator 10. An example has been described herein that the carrying-in/out device 1500 is manually moved. However, a carrier device configured to automatically carry the carrying-in/out device 1500 between the first and the second positions may be provided.

When the stacker 200 is carried into the incubator 10, a process reverse to the above carrying-out process can be performed.

A description will be given, with reference to FIGS. 33A and 33B, of the state where the carrying in/out door 27 according to an embodiment of the present invention is configured to open at a right angle with respect to the face of the opening portion of the carrying in/out port 26.

Figure 33A:
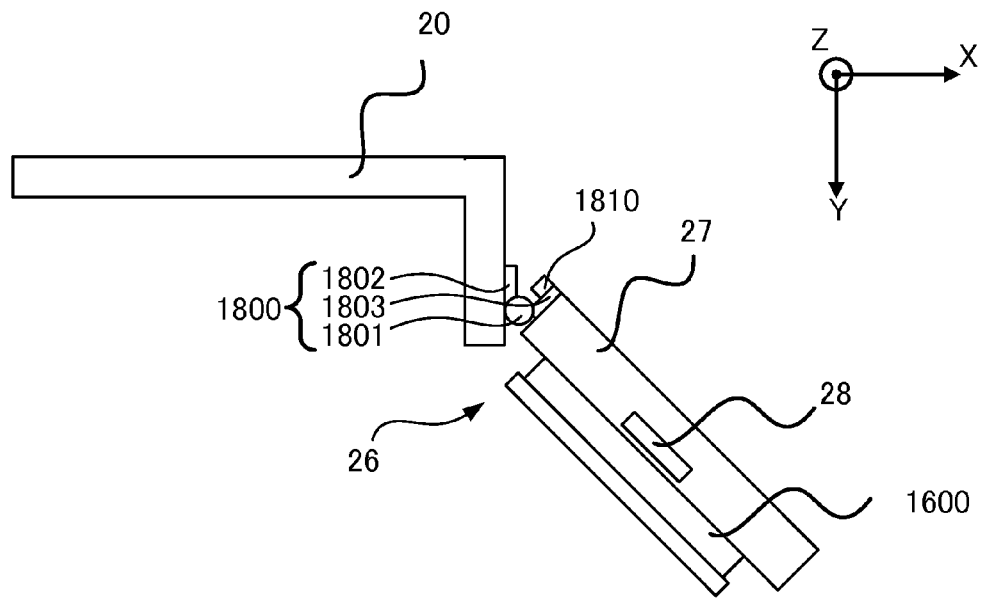
FIG. 33A is a schematic diagram for describing opening/closing of a carrying in/out door 27.
Figure 33B:
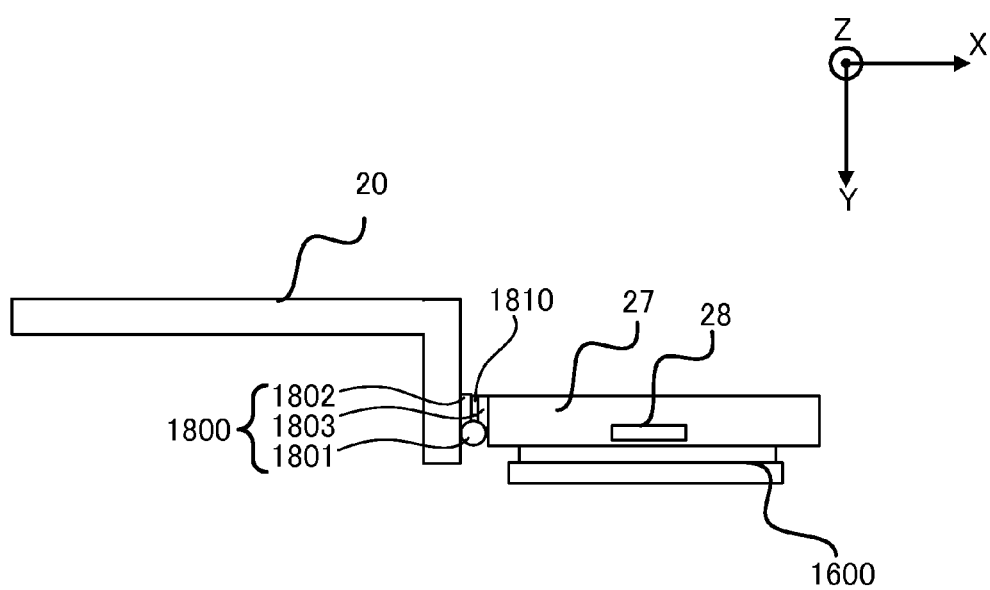
FIG. 33B is a schematic diagram for describing opening/closing of a carrying in/out door 27.

As depicted in FIG. 33A, the hinge 1800 includes: a first hinge plate 1802 made of a metal that is configured to pivot about a pivot axis 1801; and a second hinge plate 1803 made of a metal. The first hinge plate 1802 is fixed to the outer case 20 of the incubator 10, and the second hinge plate 1803 is fixed to the carrying in/out door 27.

Therefore, the carrying in/out door 27 pivots about the pivot axis 1801 of the hinge 1800 so as to be capable of opening/closing the carrying in/out port 26.

In an embodiment of the present invention, a first face of a magnet 1810 in a substantially rectangular parallelepiped shape is bonded to the second hinge plate 1803 using for example, e.g., an adhesive. The magnet 1810 has a thickness, with which a second face opposite to the first face abuts against the first hinge plate 1802 when the carrying in/out door 27 is opened at a right angle with respect to the face of the opening portion of the carrying in/out port 26.

Thus, when the carrying in/out door 27 is opened at an angle close to 90 degrees, which the carrying in/out door 27 forms with the face of the aperture of the carrying in/out port 26, the second face of the magnet 1810 and the first hinge plate 1802 stick to each other by the magnetic force, thereby being able to fix the carrying in/out door 27 to be kept opened at a right angle with respect to the face of the opening portion of the carrying in/out port 26.

Needless to say, the second face of the magnet 1810 may be bonded to the first hinge plate 1802 using for example, e.g., an adhesive. In this case, when the carrying in/out door 27 is opened at a right angle with respect to the face of the opening portion of the carrying in/out port 26, the first face opposite to the second face abuts against the second hinge plate 1803.

Therefore, when the carrying in/out door 27 is opened at an angle close to 90 degrees, which the carrying in/out door 27 forms by the face of the opening portion of the carrying in/out port 26, the first face of the magnet 1810 and the second hinge plate 1803 stick to each other by the magnetic force, thereby being able to fix the carrying in/out door 27 to be kept opened at a right angle with respect to the face of the opening portion of the carrying in/out port 26.

Figure 34A:
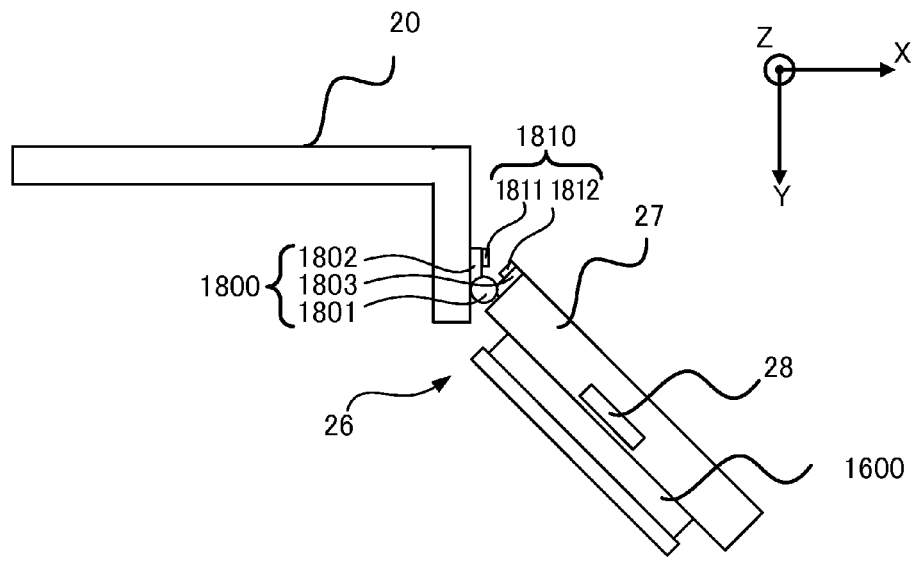
FIG. 34A is a schematic diagram for describing opening/closing of a carrying in/out door 27.
Figure 34B:
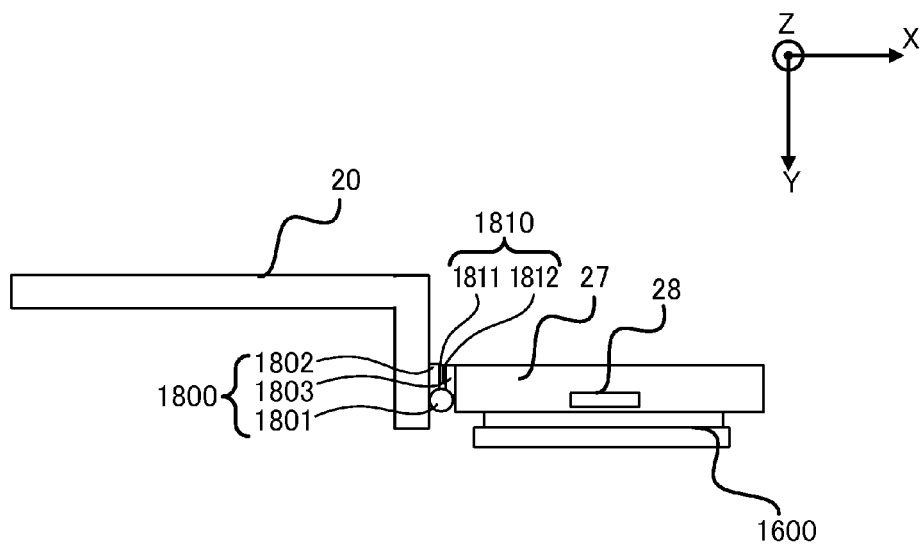
FIG. 34B is a schematic diagram for describing opening/closing of a carrying in/out door 27.

As depicted in FIGS. 34A and 34B, another structure may be employed in which a first magnet 1811 in a substantially rectangular parallelepiped shape is fixed to the first hinge plate 1802 using an adhesive and a second magnet 1812 in a rectangular parallelepiped shape is similarly fixed to the second hinge plate 1803 using an adhesive. In this case, the first and the second magnets 1811 and 1812 have thicknesses, with which the first and the second magnets 1811 and 1812 abut against each other when the carrying in/out door 27 is opened at a right angle with respect to the face of the opening portion of the carrying in/out port 26. The first and the second magnets 1811 and 1812 are fixed respectively to the first and the second hinge plates 1802 and 1803 with their directions matched so as to act their force of sticking to each other when the first and the second magnets 1811 and 1812 abut against each other.

Therefore, when the carrying in/out door 27 is opened at an angle close to 90 degrees, which the carrying in/out door 27 forms with the face of the opening portion of the carrying in/out port 26, the first and the second magnets 1811 and 1812 stick to each other by the magnetic force, thereby being able to fix the carrying in/out door 27 to be kept opened at a right angle with respect to the face of the opening portion of the carrying in/out port 26.

Figure 35:
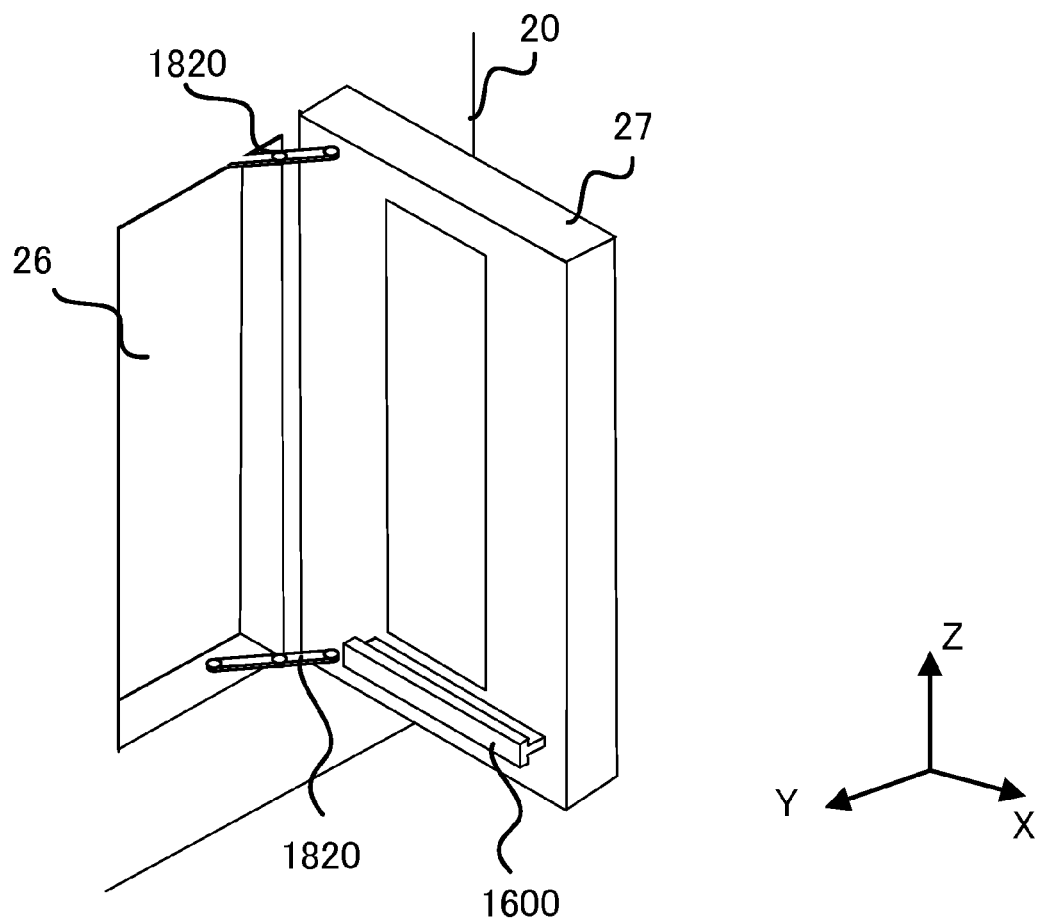
FIG. 35 is a schematic diagram for describing opening/closing of a carrying in/out door 27.

Otherwise, as depicted in FIG. 35, the outer case 20 and the carrying in/out door 27 can be configured to be coupled to each other using a stretchable door stay 1820 therebetween.

The door stay 1820 according to an embodiment of the present invention is configured to be stretchable in a range of the length from the minimal value to the maximal value, and is fixed to the outer case 20 and the carrying in/out door 27 so that the length becomes the maximal when the carrying in/out door 27 is opened at a right angle with respect to the face of the opening portion of the carrying in/out port 26.

Therefore, when the carrying in/out door 27 is opened at a right angle, which the carrying in/out door 27 forms with the face of the opening portion of the carrying in/out port 26, the length of the door stay 1820 is stretched to the maximal value, thereby being unable to open the carrying in/out door 27 any more. As such, the carrying in/out door 27 can be kept opened at a right angle with respect to the face of the opening portion of the carrying in/out port 26.

The door stay 1820 may be configured to be bent (folded) or stretched in accordance with closing/opening of the carrying in/out door 27. In this case, the door stay 1820 is fixed to the outer case 20 and the carrying in/out door 27 such that, when the angle which the carrying in/out door 27 forms with the face of the opening portion of the carrying in/out port 26 is an acute angle smaller than 90 degrees, the door stay 1820 is bent (folded), and when the carrying in/out door 27 is opened at a right angle with respect to the face of the opening portion of the carrying in/out port 26, the door stay 1820 is stretched in a straight state.

As described above, the carrying in/out door 27 according to an embodiment of the present invention can be kept opened at a right angle with respect to the face of the opening portion of the carrying in/out port 26.

In the incubator 10 according to an embodiment of the present invention, when the carrying-in/out device 1500 is pulled out to the second position, the carrying-in/out device 1500 is guided to the carrying in/out door 27, with the carrying-in/out device guide 1510 provided on the side face of the carrying-in/out device 1500 being supported by the carrying in/out door guide 1600 provided on the carrying in/out door 27. A description will be given, with reference to FIGS. 36A and 36B, of a state where the carrying-in/out device guide 1510 is supported by the carrying in/out door guide 1600.

The carrying in/out door guide (first rail member A') 1600 is provided on the inner side face of the carrying in/out door 27 so as to extend along the horizontal direction. Therefore, when the carrying in/out door 27 is opened at a right angle with respect to the face of the opening portion of the carrying in/out port 26, the carrying in/out door guide 1600 extends in a direction in which the carrying-in/out device 1500 is to be pulled out from the carrying in/out port 26 to the exterior (X-axis direction). When the carrying-in/out device 1500 is pulled out from the carrying in/out port 26, the carrying in/out door guide 1600 supports, from below, the carrying-in/out device guide (second rail member B') 1510 provided on the side face of the carrying-in/out device 1500.

Therefore, when the carrying-in/out device 1500 having the stacker 200 placed thereon is pulled out from the carrying in/out port 26 to the exterior, the carrying-in/out device guide 1510 is slid riding on the carrying in/out door guide 1600, and thus the carrying in/out door guide 1600 prevents the carrying-in/out device 1500 from bending downward due to the weight of the stacker 200.

Figure 36A:
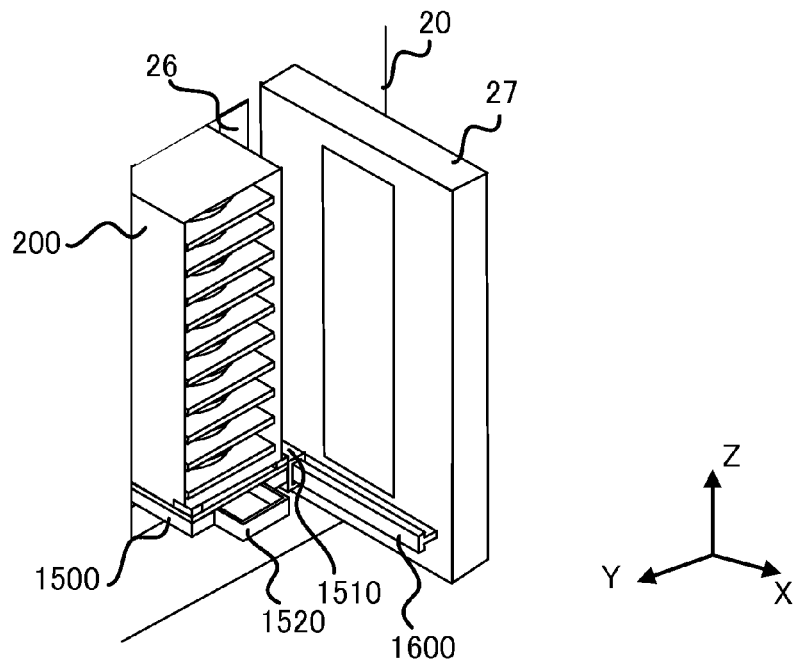
FIG. 36A is a schematic diagram for describing a state where a carrying in/out door guide 1600 and a carrying-in/out device guide 1510 are fitted with each other when a stacker 200 is carried in/out through a carrying in/out port 26.

As depicted in FIG. 36A, the carrying in/out door guide 1600 is configured with a rail having a cross-section in a T-shape, for example.

On the other hand, as depicted in FIG. 36A, the carrying-in/out device guide 1510 is configured with, for example, a rail having a cross-sectional in a C-shape. The carrying-in/out device guide 1510 is attached to a side face of the carrying-in/out device 1500 on the hinge 1800 side of the carrying in/out door 27 (on such a side that the carrying in/out door guide 1600 is positioned when the carrying in/out door 27 is opened at a right angle with respect to the carrying in/out port 26) out of the two side faces of the carrying-in/out device 1500 with respect to the movement direction thereof, so as to extend along the movement direction thereof (X-axis direction).

Figure 36B:
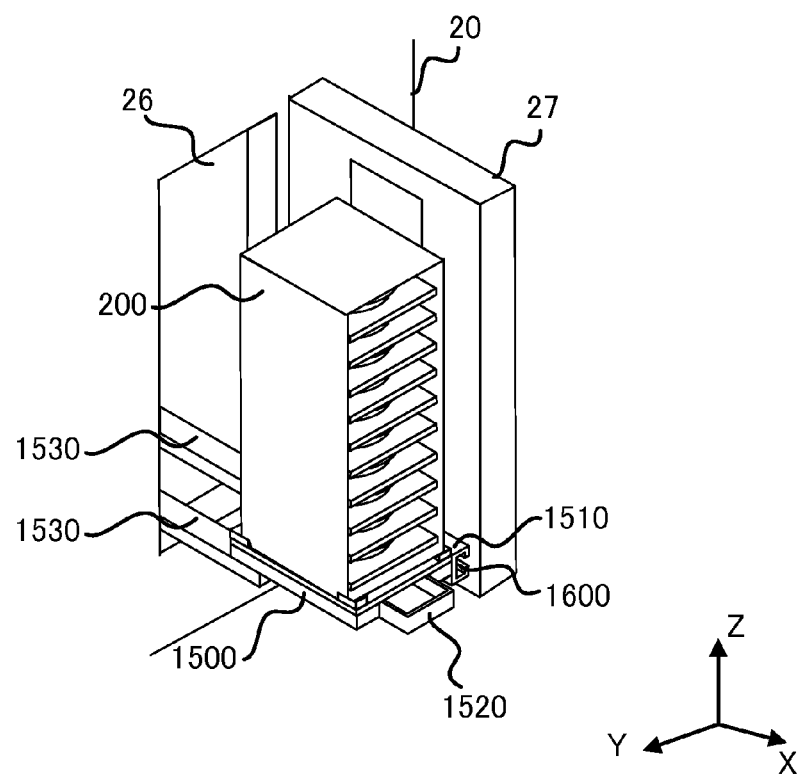
FIG. 36B is a schematic diagram for describing a state where a carrying in/out door guide 1600 and a carrying-in/out device guide 1510 are fitted with each other when a stacker 200 is carried in/out through a carrying in/out port 26.

Thereby, as depicted in FIGS. 36A and 36B, when the carrying-in/out device 1500 is pulled out from the carrying in/out port 26 to the exterior, the carrying-in/out device guide 1510 having a cross-section in a C-shape is fitted with the carrying in/out door guide 1600 having a cross-sectional in a T-shape and is slid in the pulling out direction.

As such, in the incubator 10 according to an embodiment of the present invention, the cross-sectional shapes of the carrying in/out door guide 1600 and the carrying-in/out device guide 1510 are formed such that the carrying-in/out device guide 1510 and the carrying in/out door guide 1600 are engaged with each other when the carrying-in/out device guide 1510 is moved in the direction, in which the carrying in/out door guide 1600 extends, in the case where the carrying in/out door 27 is opened at a right angle with respect to the carrying in/out port 26.

Therefore, the carrying in/out door guide 1600 prevents the carrying-in/out device 1500 from bending downward when the carrying-in/out device 1500 having the stacker 200 placed thereon is pulled out from the carrying in/out port 26 to the exterior. Further, the carrying in/out door 27 is prevented from being opened at an angle exceeding the range of 90±2 degrees when the carrying-in/out device 1500 is pulled out to the second position. Thereby, it becomes possible to prevent such an event that the carrying in/out door 27 is opened at an angle exceeding 90±2 degrees due to a certain cause; the carrying-in/out device guide 1510 loses the support by the carrying in/out door guide 1600; and the carrying-in/out device 1500 abruptly bends downward.

Further, the hinge 1800 jointing the carrying in/out door 27 and the outer case 20 may be provided with a restriction member configured to prevent the carrying in/out door 27 from being opened at an angle exceeding a range of 90±2 degrees with respect to the carrying in/out port 26, or a restriction member configured to stabilize the carrying in/out door 27 when the carrying in/out door 27 is opened at an angle within the range of 90±2 degrees with respect thereto. Thereby, when the carrying-in/out device 1500 is pulled out to the exterior, the carrying-in/out device guide 1510 smoothly engaged with the carrying in/out door guide 1600, as well as when the carrying-in/out device 1500 is pulled out to the second position, the carrying in/out door 27 is prevented from being opened at an angle exceeding the range of 90±2 degrees.

The restriction member can be realized by, for example, the magnet 1810, the first and the second magnet 1811 and 1812, or the door stay 1820.

FIG. 37 depicts the structure of the carrying-in/out device 1500. As depicted in FIG. 37, the carrying-in/out device 1500 includes a slide table 1540, slide rails 1530, the carrying-in/out device guide 1510, and the handle 1520. The slide table 1540 is formed with positioning pins (convex portions) 1550 and positioning guides 1560 at the predetermined positions.

The slide table 1540 is a stand to have the stacker 200 placed thereon; is fixed to the slide rails 1530 using for example, e.g., bolts; and has the handle 1520 and the carrying-in/out device guide 1510 fixed thereto.

The slide rails 1530 each include a base 1533, a rail 1532, and a slider 1531. The base 1533 is fixed to the compartment 15 (first position) of the shelf 46b. The rail 1532 is disposed on the base 1533 along the movement direction of the slider 1531 (X-axis direction). The slider 1531 is installed so as to be capable of moving on the rail 1532 in the X-axis direction. The slider 1531 has the slide table 1540 fixed thereto.

With such a structure, the slide table 1540 can be moved in the horizontal direction from the first position in the vicinity of the carrying in/out port 26 in the incubator 10 to the second position outside the incubator 10.

The positioning pins 1550 disposed on the slide table 1540 are fitted with positioning grooves (fitting portions) 1700 formed in the bottom face of the stacker 200 when the stacker 200 is placed on the slide table 1540. FIG. 38 depicts the state where the positioning grooves 1700 are formed in the bottom face of the stacker 200. Thereby, it becomes possible to prevent misalignment of the stacker 200 placed on the carrying-in/out device 1500.

For example, e.g., the bolts fixing the slide table 1540 to the slide rails 1530 may be utilized as the positioning pins 1550. Thereby, both of the functions of fixing the slide table 1540 and preventing the misalignment of the stacker 200 can be realized using the positioning pins 1550.

The positioning guides 1560 are provided in the four corners of the slide table 1540, respectively. The positioning guides 1560 each can be configured with, for example, a triangle member that is bent at a right angle with the slope thereof oriented inward and upward, and is provided on the face opposed to the bottom face of the stacker 200 at each of the four corners when the stacker 200 is placed on the slide table 1540.

By providing the positioning guides 1560 on the slide table 1540, the positioning grooves 1700 formed in the bottom face of the stacker 200 can be guided to be appropriately fitted with the positioning pins 1550 formed on the slide table 1540, when the stacker 200 is placed on the slide table 1540.

FIG. 39 depicts the state where the label reader 28 provided on the carrying in/out door 27 reads a tag such as an electronic tag or a bar code attached to each of the containers 100 in the stacker 200. In this tag, the identification information for uniquely identifying each container 100 is recorded.

As depicted in FIG. 39, the label reader 28 includes a reader/writer 1610 and a plurality of antennas (reading devices) 1620. The antennas 1620 are disposed at positions corresponding to the positions of electronic tags 111, respectively so as to read information of the electronic tags 111 respectively attached to the containers 100 that are stored in the stacker 200 in the multi-story manner, in the state where the stacker 200 is placed on the carrying-in/out device 1500. The reader/writer 1610 acquires the identification information of the containers read by the antennas 1620 from the electronic tags 111, and transmits the identification information to the control device 15.

When the stacker 200 is carried into or out from the incubator 10, the label reader 28 reads the identification information of the containers 100 in the stacker 200 from the electronic tags 111 according to an instruction from the control device 15.

As described above, the incubator 10 according to an embodiment of the present invention is configured such that, when the carrying-in/out device 1500 is pulled out to the second position, the carrying-in/out device guide 1510 provided on the carrying-in/out device 1500 is supported by the carrying in/out door guide 1600 provided on the carrying in/out door 27. Therefore, it become possible to prevent the carrying-in/out device 1500 whose weight load is increased by having the stacker 200 placed thereon from bending downward at the second position.

Thereby, vibrations and inclination of the stacker 200 can be restrained when the stacker 200 capable of storing therein a plurality of containers 100 including liquid is carried in and out.

Further, when the carrying-in/out device 1500 having the stacker 200 placed thereon is pulled out to the second position, misalignment does not occur between the positions of the electronic tags 111 of the containers 100 in the stacker 200 and those of the antennas 1620 in the carrying in/out door 27. Therefore, it becomes possible to improve the accuracy of reading the information from the electronic tags 111.

Thereby, the incubator 10 according to an embodiment of the present invention can execute the work of reading the information from the electronic tags 111 in a short time, and thus it becomes possible to handle a greater number of culture containers 100 more efficiently.

In the incubator 10 according to an embodiment of the present invention, the cross-sectional shapes of the carrying in/out door guide 1600 and the carrying-in/out device guide 1510 are formed such that the carrying-in/out device guide 1510 and the carrying in/out door guide 1600 are engaged with each other when the carrying-in/out device 1500 is pulled out from the first position to the second position.

Thereby, the carrying in/out door 27 can be fixed at a right angle with respect to the carrying in/out port 26 in the state where the carrying-in/out device 1500 has been pulled out to the second position. Thus, the distance can be maintained constant between the antennas 1620 provided in the carrying in/out door 27 and the electronic tags 111 attached to the containers 100 stored in the stacker 200 in the multi-story state. Therefore, it becomes possible to improve the accuracy of reading the information from the electronic tags 111.

With the incubator 10 according to an embodiment of the present invention, vibrations and inclination of the stacker 200 can be restrained when the stacker 200 capable of storing therein a plurality of containers 100 including liquid is carried in and out. Thus, spill of the liquid in the container 100 can be prevented. Thereby, the incubator 10 according to an embodiment of the present invention can handle a greater number of containers 100 more efficiently. Further, when the container 100 contains a culture such as a cell, influence on the culture due to vibrations can be avoided.

In the case where the incubator 10 is configured such that the electronic tags 111 having the identification information of the containers 100 recorded therein are attached to the containers 100, respectively; such a plurality of containers 100 are stored in the stacker 200 in the multi-story state; and the identification information of the containers 100 recorded in the electronic tags 111 in the stacker 200 is read using the antennas 1620 provided on the side face of the carrying in/out door 27, when the carrying-in/out device 1500 having the stacker 200 placed thereon has been pulled out to the second position in the exterior of the incubator 10, misalignment does not occur between the positions of the electronic tags 111 of the containers 100 in the stacker 200 and those of the antennas 1620 in the carrying in/out door 27. Therefore, it becomes possible to improve the accuracy of reading the information from the electronic tags 111.

Thereby, the incubator 10 according to an embodiment of the present invention can execute the work of reading the information from the electronic tags 111 in a short time, thereby being able to handle a greater number of culture containers 100 more efficiently.

The above embodiments of the present invention are simply for facilitating the understanding of the present invention and are not in any way to be construed as limiting the present invention. The present invention may variously be changed or altered without departing from its spirit and encompass equivalents thereof.

For example, although the carrying in/out door guide 1600 provided on the carrying in/out door 27 is only one in an embodiment of the present invention, a plurality of carrying in/out door guides 1600 may be provided to be parallel to each other on the carrying in/out door 27. In this case, the carrying-in/out device 1500 is provided with a plurality of carrying-in/out device guides 1510 corresponding to the carrying in/out door guides 1600. With such a structure, it becomes possible to more effectively reduce the amount of bending of the carrying-in/out device 1500 caused by the weight of the stacker 200.

Further, the shapes of the carrying in/out door guide 1600 and the carrying-in/out device guide 1510 are not limited to the T-shape and the C-shape in cross-sections, respectively, and may be various shapes with which they are engaged with each other.

The purpose of the present invention can be also achieved by inserting a roller between the carrying in/out door guide 1600 and the carrying-in/out device guide 1510.

The label reader 28 configured to read the identification information of the electronic tag 111 may be provided at a position other than that on the side face of the carrying in/out door 27. For example, as depicted in FIG. 32 by a dotted line, the label reader 28 may be provided at a position at which the label reader 28 is able to read the information of the electric tag when the stacker 200 is placed on the carrying-in/out device 1500, that is, may be provided on the edge portion of the carrying in/out port 26 in the outer case 20 or in the compartment 15 of the shelf 46b. By providing the label reader 28 at this position, for example, a cable connecting the label reader 28 and the control device 15 to each other is not required to pass through the hinge portion that couples the outer case 20 with the carrying in/out door 27 in a pivotable manner. Therefore, the attachment of the carrying in/out door 27 to the outer case 20 can be simplified.

What is claimed is:

1. A storage apparatus comprising:
   a storage member configured to store a plurality of containers including liquid, the storage member provided with a pair of first rail members on side faces thereof, the pair of first rail members extending along a horizontal direction;
   a storage rack configured to store the storage member;
   a carrying mechanism configured to carry the storage member placed thereon in the horizontal direction to a storage location of the storage rack so that the storage member will be stored in the storage rack; and
   a pair of walls, provided so as to be opposed to the side faces of the storage member, respectively, having a pair of second rail members provided on side faces thereof opposed to the pair of first rail members, respectively, in a state where the storage member is stored in the storage rack, the pair of second rail members extending in the horizontal direction,
   the storage member being guided to the storage rack with the pair of first rail members being supported by the pair of second rail members, when the carrying mechanism is moved in the horizontal direction toward the storage rack;
   wherein each of the pair of first rail members is provided with first and second convex portions at first and second predetermined positions on a face thereof in contact with each of the pair of second rail members,
   each of the pair of second rail members is provided with first and second fitting portions to be respectively fitted with the first and the second convex portions, at positions opposed to the first and the second predetermined positions of each of the pair of first rail members, in a state where the storage member is stored in the storage rack,
   the second predetermined position is a position spaced apart from both of a straight line passing through the first predetermined position and extending in a storage direction of the storage member and another straight line, orthogonal to the straight line, passing through the first predetermined position, and
   the first fitting portion is displaced from the second fitting portion in a direction orthogonal to the storage direction of the storage member.

2. The storage apparatus of claim 1, wherein
   each of the pair of first rail members is provided with a convex portion at a predetermined position on a face thereof in contact with each of the pair of second rail members, and wherein
   each of the pair of second rail members is formed with a fitting portion to be fitted with the convex portion of each of the pair of first rail members, at a position opposed to the predetermined position of each of the pair of first rail members, in a state where the storage member is stored in the storage rack.

3. The storage apparatus of claim 2, wherein
   the storage rack includes a wall face opposed to a front face of the storage member, which the front face is in the storage direction of the storage member, in a state where the storage member is stored in the storage rack, wherein
   the wall face is formed with first and second protruding portions arranged in line in a vertical direction, and wherein
   the first and the second protruding portions are formed such that the first and the second protruding portions are brought into contact with the front face of the storage member when the convex portions of the pair of first rail members are fitted with the fitting portions of the pair of second rail members, respectively.

4. The storage apparatus of claim 1, wherein
   each second rail member includes:
   a support rail configured to support each first rail member when said each first rail member is moved in the storage direction of the storage member; and
   a guide rail provided above the support rail and arranged in parallel with the support rail, the guide rail configured to guide the first rail member so as not to be derailed from the support rail.

5. The storage apparatus of claim 4, wherein
   the guide rail of each second rail member is provided with a rotatable roller configured to elastically bias each first rail member toward the support rail.

6. The storage apparatus of claim 1, wherein
   each first rail member is formed at a height substantially equal to a height at which the storage member has a center of gravity.

* * * * *